US007658891B1

(12) United States Patent
Barnes

(10) Patent No.: US 7,658,891 B1
(45) Date of Patent: Feb. 9, 2010

(54) AIR PURIFICATION AND DECONTAMINATION FOR HAZMAT SUITS

(76) Inventor: Ronald L. Barnes, 2823 Castle Pines Cir., Owens Crossroads, AL (US) 35763

( * ) Notice: Subject to any disclaimer, the term of this patent is extended or adjusted under 35 U.S.C. 154(b) by 618 days.

(21) Appl. No.: 10/923,906

(22) Filed: Aug. 23, 2004

Related U.S. Application Data

(63) Continuation-in-part of application No. 10/176,299, filed on Jun. 20, 2002, now Pat. No. 6,967,008, which is a continuation-in-part of application No. 09/717,903, filed on Nov. 20, 2000, now Pat. No. 6,428,756, said application No. 10/176,299 is a continuation-in-part of application No. 09/794,601, filed on Feb. 27, 2001, now abandoned, which is a continuation-in-part of application No. 09/752,982, filed on Dec. 31, 2000, now Pat. No. 6,623,635, and a continuation-in-part of application No. 09/393,437, filed on Sep. 10, 1999, now Pat. No. 6,192,911, said application No. 10/176,299 is a continuation-in-part of application No. 10/061,752, filed on Feb. 1, 2002, now Pat. No. 6,723,233, which is a continuation-in-part of application No. 09/752,982, which is a continuation-in-part of application No. 09/418,915, filed on Oct. 15, 1999, now Pat. No. 6,342,154, said application No. 10/176,299 is a continuation-in-part of application No. 09/794,601, which is a continuation-in-part of application No. 09/752,982, said application No. 10/176,299 is a continuation-in-part of application No. 09/393,437, and a continuation-in-part of application No. 09/520,504, (Continued)

(51) Int. Cl.
*B01J 19/08* (2006.01)
*A62B 25/00* (2006.01)

(52) U.S. Cl. .............................. 422/186.03; 128/205.28
(58) Field of Classification Search .............. 422/186.3;
128/205.28
See application file for complete search history.

(56) References Cited

U.S. PATENT DOCUMENTS 3,957,949 A 5/1976 Senjo et al.
3,977,831 A 8/1976 Fletcher et al.

(Continued)

FOREIGN PATENT DOCUMENTS

JP 11206316 A 8/1999

OTHER PUBLICATIONS

U.S. Appl. No. 11/980,019, Ronald L. Barnes.
U.S. Appl. No. 11/284,290, Ronald L. Barnes.
U.S. Appl. No. 11/305,975, Ronald L. Barnes.
U.S. Appl. No. 11/034,115, Ronald L. Barnes.

*Primary Examiner*—Kishor Mayekar
(74) *Attorney, Agent, or Firm*—Mark Clodfelter

(57) ABSTRACT

This application relates to innovative apparatus and methods for efficient use of vacuum ultraviolet light and ozone to break down biological and chemical contaminants in air that flows through such apparatus, and to generate additional ozone and ozonites that further contribute to destruction of contaminants in air in a generally enclosed contaminated volume communicating with such apparatus, as well as contaminants on surfaces and within porous materials such as clothing in a generally enclosed volume, and including contaminants on the hair or skin of an individual, or on the hide or fur of an animal. A generally enclosed contaminated volume may include an interior of a hazardous materials (HAZMAT) protective suit donned by an individual, or in an environment, that was already contaminated, or a passenger compartment of a vehicle operated or parked in a contaminated area.

26 Claims, 18 Drawing Sheets

Related U.S. Application Data filed on Mar. 8, 2000, now Pat. No. 6,405,387, and a continuation-in-part of application No. 09/717,904, filed on Nov. 20, 2000, now Pat. No. 6,426,053, application No. 10/923,906, which is a continuation-in-part of application No. 10/208,897, filed on Jul. 30, 2002, now Pat. No. 6,951,633, which is a continuation-in-part of application No. 09/717,904, filed on Nov. 20, 2000, now Pat. No. 6,426,053, application No. 10/923,906, which is a continuation-in-part of application No. 10/867,860, filed on Jun. 15, 2004, which is a continuation-in-part of application No. 09/197,036, filed on Nov. 21, 1998, now Pat. No. 6,689,610, said application No. 10/867,860 is a continuation-in-part of application No. 10/827,708, filed on Apr. 20, 2004, now Pat. No. 7,060,180, which is a continuation-in-part of application No. 10/061,752, which is a continuation-in-part of application No. 09/752,982, which is a continuation-in-part of application No. 09/418,915, said application No. 10/827,708 is a continuation-in-part of application No. 09/794,601, which is a continuation-in-part of application No. 09/752,982, said application No. 10/827,708 is a continuation-in-part of application No. 09/717,904, and a continuation-in-part of application No. 09/520,504, said application No. 10/867,860 is a continuation-in-part of application No. 10/176,299, which is a continuation-in-part of application No. 09/717,903, said application No. 10/176,299 is a continuation-in-part of application No. 09/794,601, which is a continuation-in-part of application No. 09/752,982, which is a continuation-in-part of application No. 09/393,437, said application No. 10/176,299 is a continuation-in-part of application No. 10/061,752, which is a continuation-in-part of application No. 09/752,982, which is a continuation-in-part of application No.09/418,915, said application No. 10/176,299 is a continuation-in-part of application No. 09/794,601, which is a continuation-in-part of application No. 09/752,982, and a continuation-in-part of application No. 09/717,904, and a continuation-in-part of application No. 09/520,504, and a continuation-in-part of application No. 09/393,437, application No. 10/923,096, which is a continuation-in-part of application No. 10/611,146, filed on Jul. 1, 2003, now abandoned.

(60) Provisional application No. 60/392,863, filed on Jul. 1, 2002, provisional application No. 60/166,254, filed on Nov. 18, 1999, provisional application No. 60/166,255, filed on Nov. 18, 1999, provisional application No. 60/066,119, filed on Nov. 21, 1997.

(56) References Cited

U.S. PATENT DOCUMENTS

| | | |
|---|---|---|
| 4,035,296 A | 7/1977 | Armstrong |
| 4,361,486 A | 11/1982 | Hou et al. |
| 4,596,648 A | 6/1986 | Sweeney |
| 5,008,087 A | 4/1991 | Batchelor |
| D351,649 S | 10/1994 | Lin |
| 5,572,991 A | 11/1996 | Grilliot |
| 5,635,059 A | 6/1997 | Johnson |
| 5,879,641 A | 3/1999 | Conrad et al. |
| 6,060,027 A | 5/2000 | Conrad et al. |
| 6,190,622 B1 | 2/2001 | Conrad et al. |
| 6,207,064 B1 | 3/2001 | Gargas |
| 6,491,879 B2 | 12/2002 | Conrad |
| 6,537,494 B2 | 3/2003 | Garlick |
| 6,589,489 B2 | 7/2003 | Morrow et al. |
| 6,620,379 B1 | 9/2003 | Piuk et al. |
| 6,630,105 B1 | 10/2003 | O'Neill et al. |
| 6,974,562 B2 | 12/2005 | Ciampi et al. |

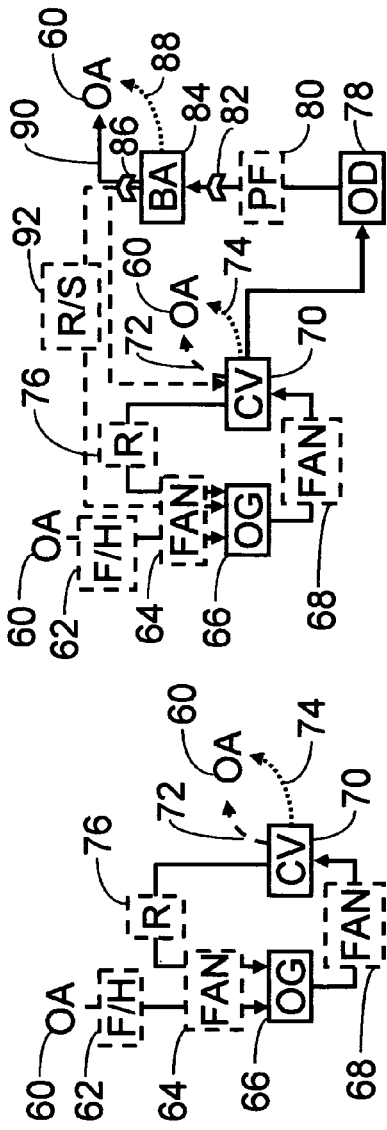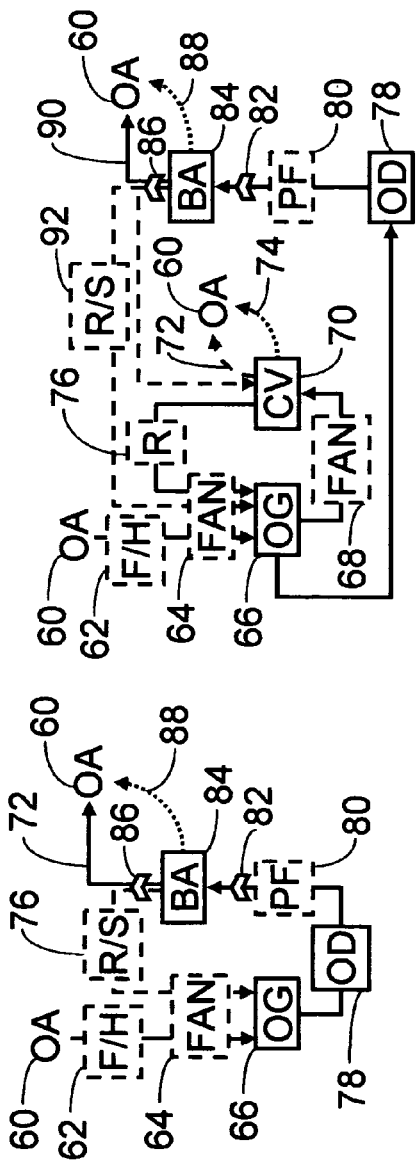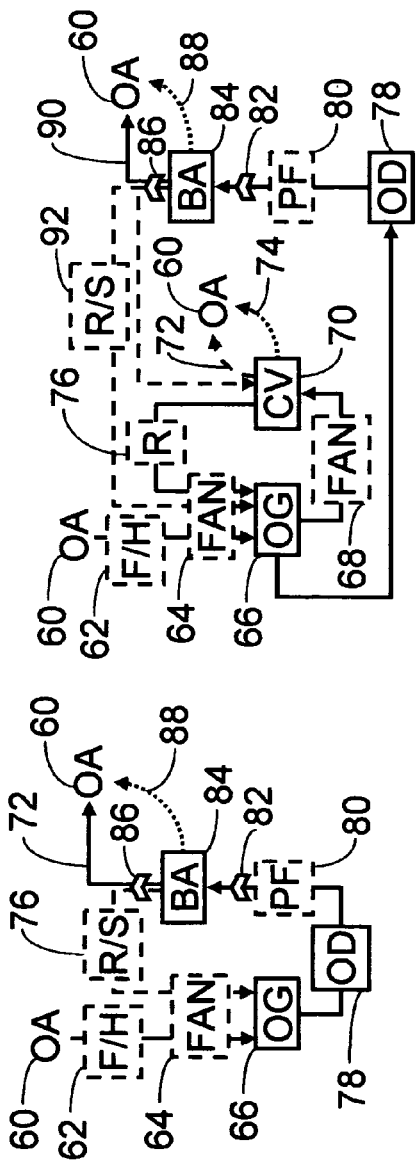

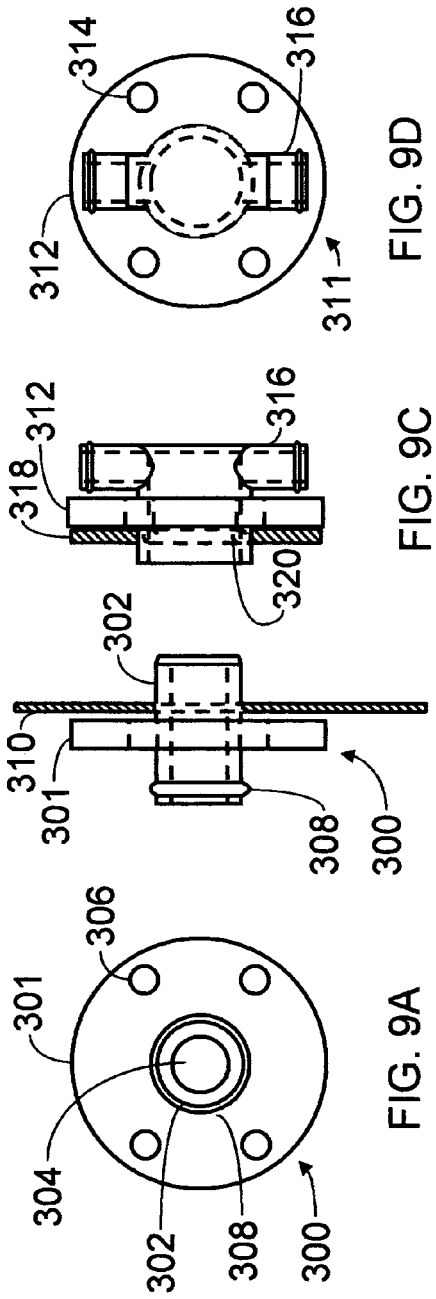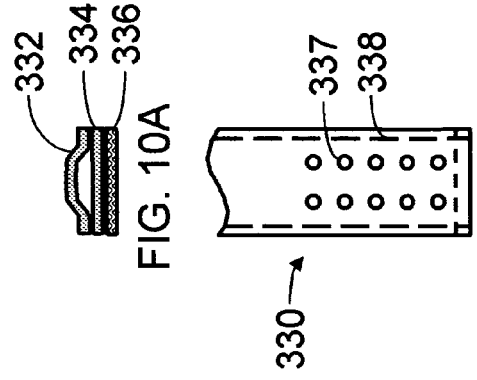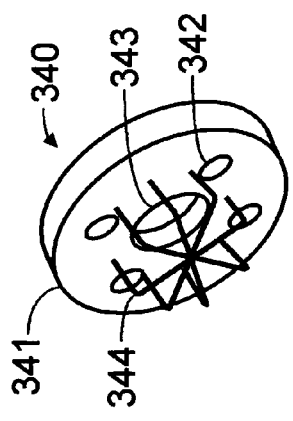

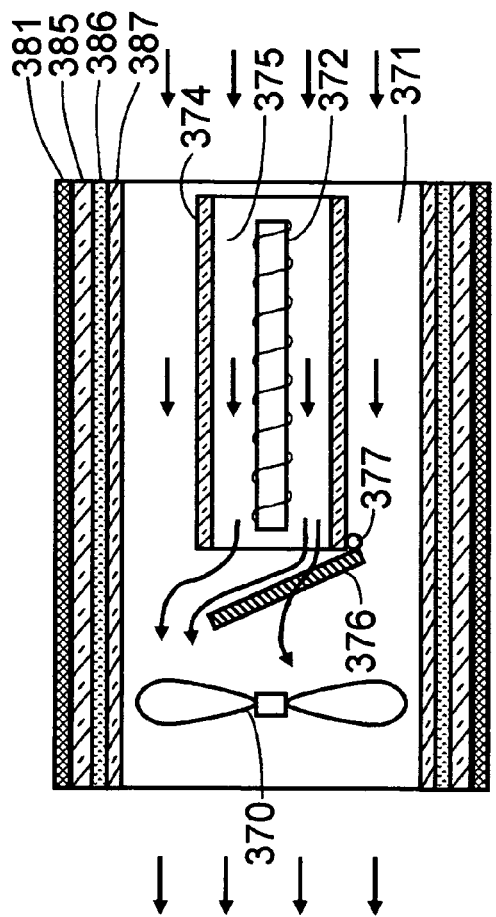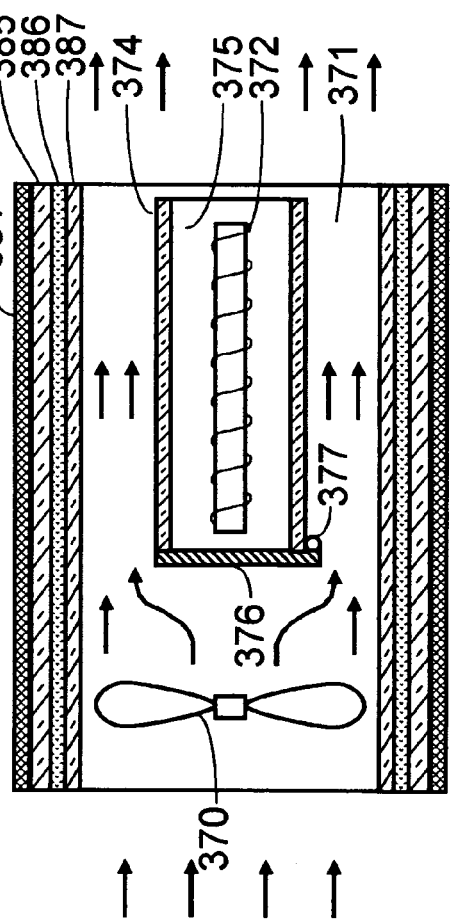

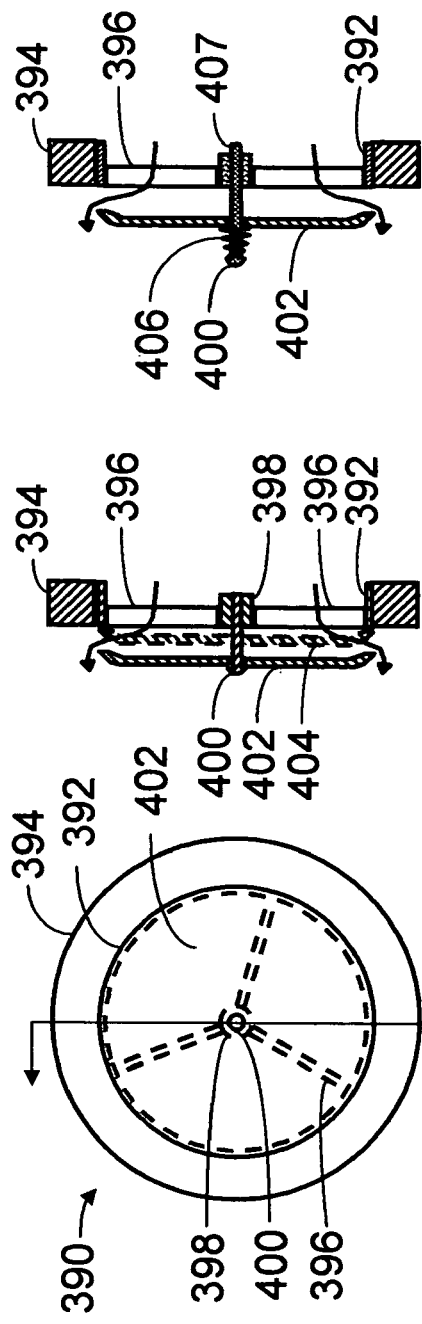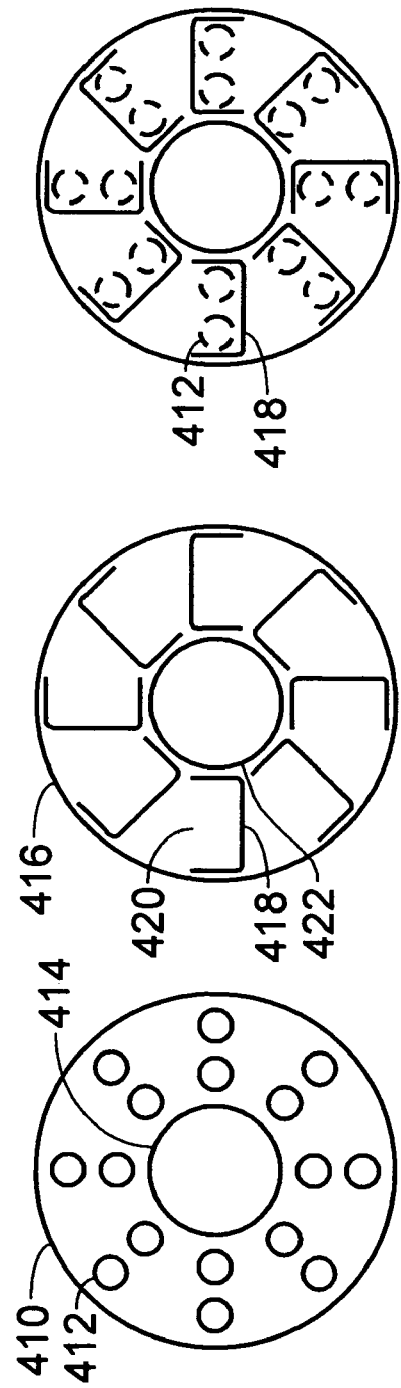

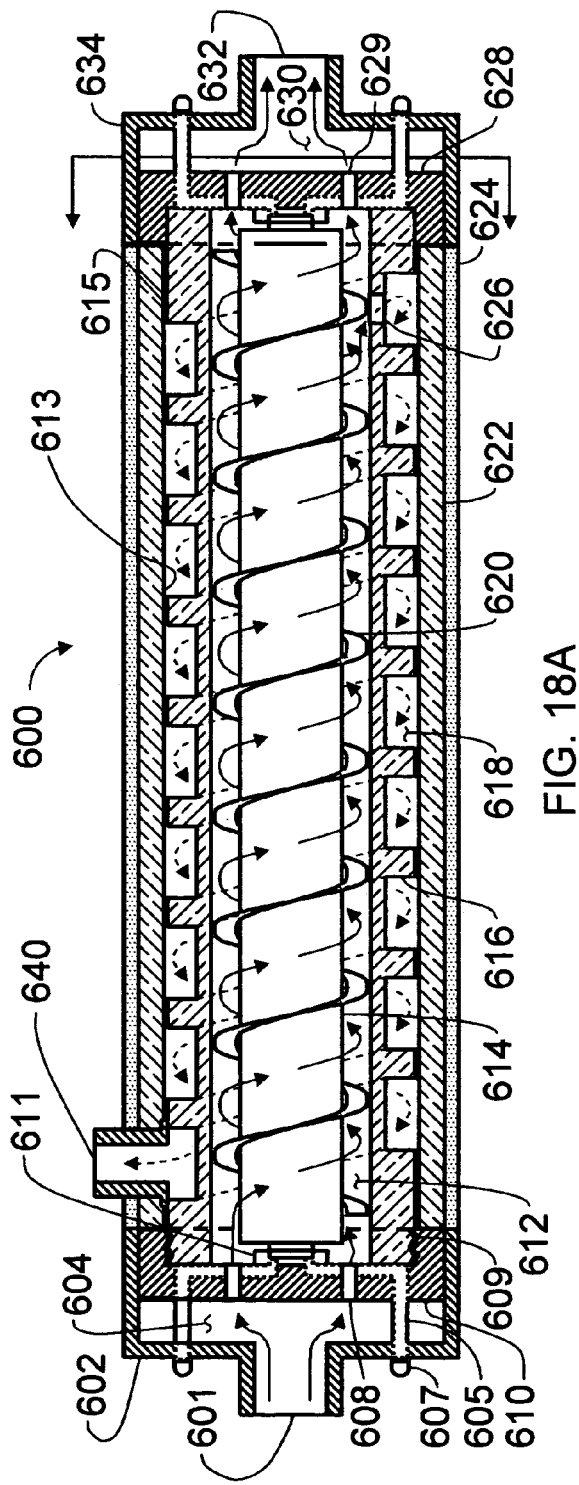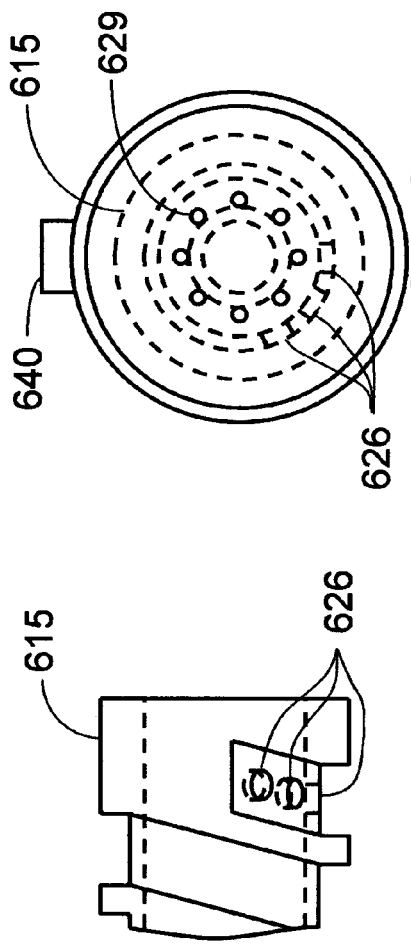
FIG. 18A
FIG. 18B
FIG. 18C

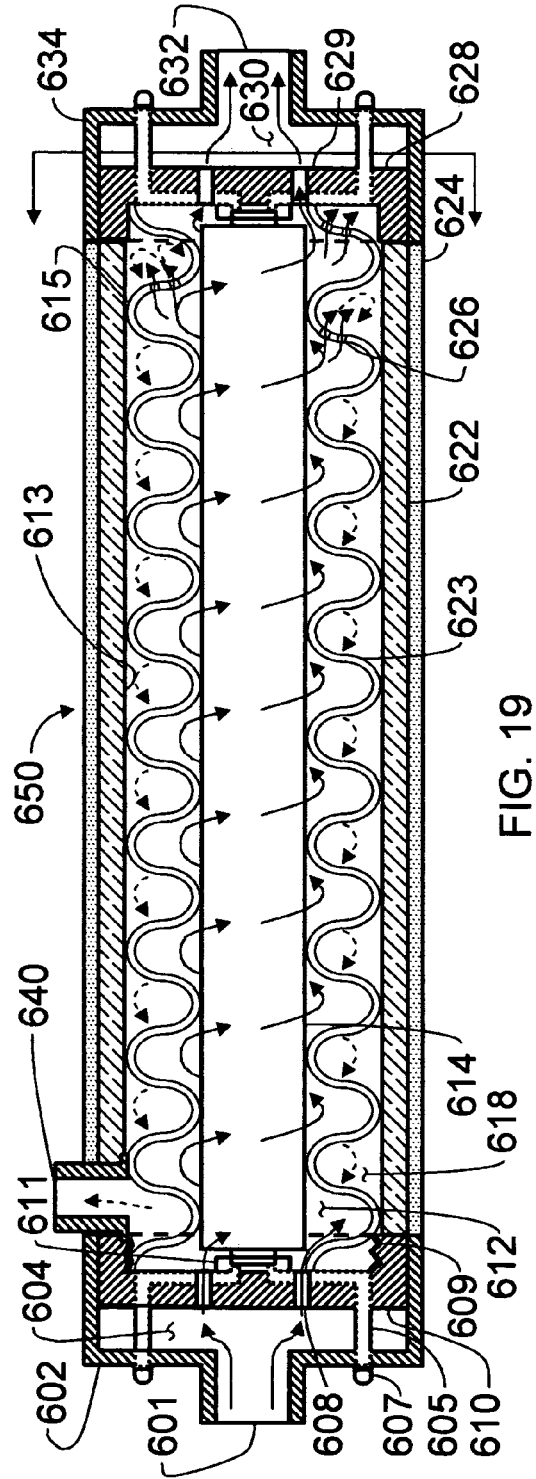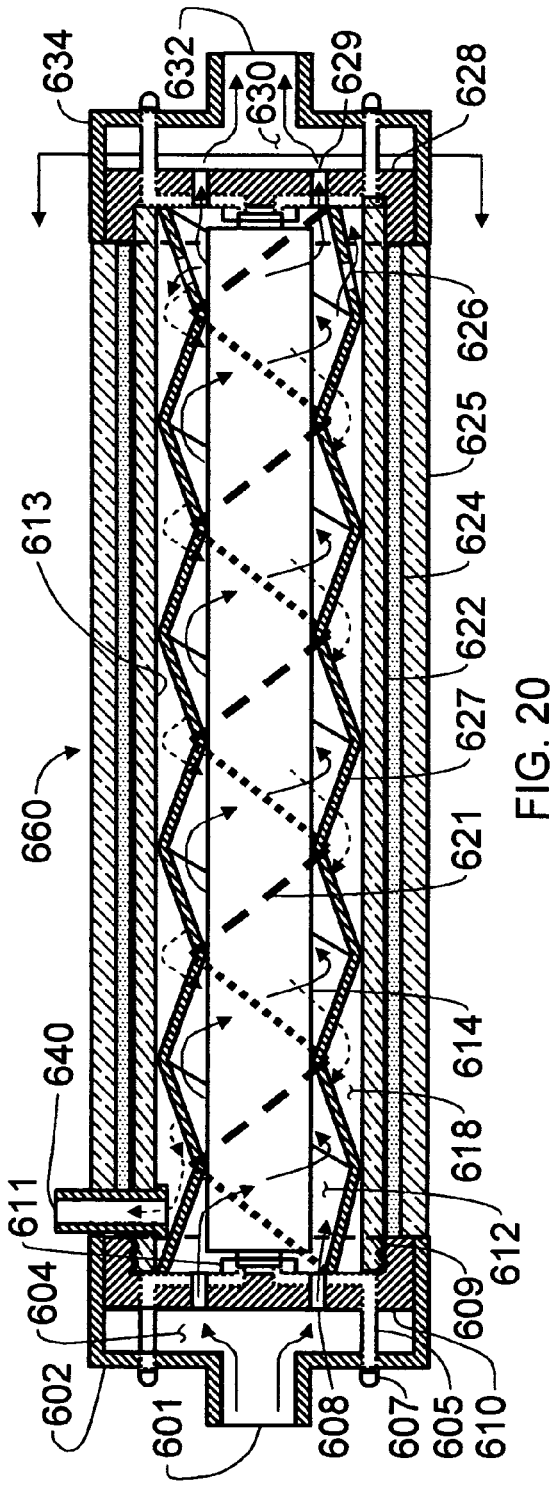

ated Jan. 29, 2002. In addition, the
AIR PURIFICATION AND DECONTAMINATION FOR HAZMAT SUITS

CROSS REFERENCE TO RELATED APPLICATIONS

The instant application is a continuation-in-part application of Applicant's U.S. application Ser. No. 10/176,299, filed Jun. 20, 2002, now U.S. Pat. No. 6,967,008, issued Nov. 22, 2005, which is a continuation-in-part application of Applicant's U.S. application Ser. No. 09/717,903, filed Nov. 20, 2000, now U.S. Pat. No. 6,428,756, issued Aug. 6, 2002, which claims the benefit of U.S. provisional application No. 60/166,254, filed Nov. 18, 1999. The U.S. application Ser. No. 10/176,299, now U.S. Pat. No. 6,967,008, is also a continuation-in-part of U.S. patent application Ser. No. 09/794,601, filed Feb. 27, 2001, now abandoned, which is a continuation-in-part of U.S. patent application Ser. No. 09/752,982, filed Dec. 31, 2000, now U.S. Pat. No. 6,623,635, issued Sep. 23, 2003, and a continuation-in-part of U.S. patent application Ser. No. 09/393,437, filed Sep. 10, 1999, now U.S. Pat. No. 6,192,911, issued Feb. 27, 2001. The U.S. application Ser. No. 10/176,299, now U.S. Pat. No. 6,967,008, is also a continuation-in-part of U.S. patent application Ser. No. 10/061,752, filed Feb. 1, 2002, now U.S. Pat. No. 6,723,233, issued Apr. 20, 2004, which is a continuation-in-part of U.S. patent application Ser. No. 09/752,982, filed Dec. 31, 2000, now U.S. Pat. No. 6,623,635, which is a continuation-in-part of U.S. patent application Ser. No. 09/418,915, filed Oct. 15, 1999, now U.S. Pat. No. 6,342,154, issued Jan. 29, 2002. The U.S. application Ser. No. 10/176,299 is also a continuation-in-part of abandoned U.S. patent application Ser. No. 09/794,601, filed Feb. 27, 2001, which is a continuation-in-part of U.S. patent application Ser. No. 09/752,982, filed Dec. 31, 2000, now U.S. Pat. No. 6,623,635. The U.S. application Ser. No. 10/176,299, now U.S. Pat. No. 6,967,008, is also a continuation-in-part of U.S. patent application Ser. No. 09/393,437, filed Sep. 10, 1999, now U.S. Pat. No. 6,192,911, issued Feb. 27, 2001, and is also a continuation-in-part of U.S. patent application Ser. No. 09/520,504, filed Mar. 8, 2000, now U.S. Pat. No. 6,405,387, issued Jun. 18, 2002, and is also a continuation-in-part of U.S. patent application Ser. No. 09/717,904, filed Nov. 20, 2000, now U.S. Pat. No. 6,426,053, issued Jul. 30, 2002.

The instant application is also a continuation-in-part of Applicant's U.S. application Ser. No. 10/208,897, filed Jul. 30, 2002, now U.S. Pat. No. 6,951,633, issued Oct. 4, 2005, which is a continuation-in-part of U.S. patent application Ser. No. 09/717,904, filed Nov. 20, 2000, now U.S. Pat. No. 6,426,053, issued Jul. 30, 2002, and which claims the benefit of U.S. provisional application No. 60/166,255, filed Nov. 18, 1999.

The instant application is also a continuation-in-part of Applicant's copending U.S. patent application Ser. No. 10/867,860, filed Jun. 15, 2004, which is a continuation-in-part of Applicant's U.S. patent application Ser. No. 09/197,036, filed Nov. 21, 1998, now U.S. Pat. No. 6,689,610, issued Oct. 4, 2005, which claims the benefit of U.S. provisional patent application Ser. No. 60/066,119, filed Nov. 21, 1997. The copending U.S. application Ser. No. 10/867,860 is also a continuation-in-part of Applicant's U.S. patent application Ser. No. 10/827,708, filed Apr. 20, 2004, now U.S. Pat. No. 7,060,180, issued Jun. 13, 2006, which is a continuation-in-part of Applicant's U.S. patent application Ser. No. 10/061,752, filed Feb. 1, 2002, now U.S. Pat. No. 6,723,233, issued Apr. 20, 2004, which is a continuation-in-part of Applicant's U.S. patent application Ser. No. 09/752,982, filed Dec. 31, 2000, now U.S. Pat. No. 6,623,635, issued Sep. 23, 2003, which is a continuation-in-part of Applicant's U.S. patent application Ser. No. 09/418,915, filed Oct. 15, 1999, now U.S. Pat. No. 6,342,154, issued Jan. 29, 2002. In addition, the U.S. application Ser. No. 10/827,708, filed Apr. 20, 2004, now U.S. Pat. No. 7,060,180, is a continuation-in-part of Applicant's abandoned U.S. application Ser. No. 09/794,601, filed Feb. 27, 2001, which is a continuation-in-part of U.S. patent application Ser. No. 09/752,982, filed Dec. 31, 2000, now U.S. Pat. No. 6,623,635, issued Sep. 23, 2003. In addition, the U.S. application Ser. No. 10/827,708 filed Apr. 20, 2004, now U.S. Pat. No. 7,060,180, is a continuation-in-part of U.S. patent application Ser. No. 09/520,504, filed Mar. 8, 2000, now U.S. Pat. No. 6,405,387, issued Jun. 18, 2002, and a continuation-in-part of Applicant's U.S. patent application Ser. No. 09/717,904, filed Nov. 20, 2000, now U.S. Pat. No. 6,426,053, issued Jul. 30, 2002. In addition, the copending U.S. application Ser. No. 10/867,860 is a continuation-in-part application of Applicant's U.S. patent application Ser. No. 10/176,299, filed Jun. 20, 2002, now U.S. Pat. No. 6,967,008, which is a continuation-in-part application of U.S. application Ser. No. 09/717,903, filed Nov. 20, 2000, now U.S. Pat. No. 6,428,756, which claims the benefit of U.S. provisional application No. 60/166,254, filed Nov. 18, 1999. The U.S. application Ser. No. 10/176,299, now U.S. Pat. No. 6,967,008, is also a continuation-in-part of abandoned U.S. patent application Ser. No. 09/794,601, filed Feb. 27, 2001, which is a continuation-in-part of U.S. patent application Ser. No. 09/752,982, filed Dec. 31, 2000, now U.S. Pat. No. 6,623,635, issued Sep. 23, 2003, which is a continuation-in-part of U.S. patent application Ser. No. 09/393,437, filed Sep. 10, 1999, now U.S. Pat. No. 6,192,911, issued Feb. 27, 2001. The U.S. application Ser. No. 10/176,299, now U.S. Pat. No. 6,967,008, is also a continuation-in-part of U.S. patent application Ser. No. 10/061,752, filed Feb. 1, 2002, now U.S. Pat. No. 6,723,233, issued Apr. 20, 2004, which is a continuation-in-part of U.S. patent application Ser. No. 09/752,982, filed Dec. 31, 2000, now U.S. Pat. No. 6,623,635, which is a continuation-in-part of U.S. patent application Ser. No. 09/418,915, filed Oct. 15, 1999, now U.S. Pat. No. 6,342,154, issued Jan. 29, 2002, and which is a continuation-in-part of abandoned U.S. patent application Ser. No. 09/794,601, filed Feb. 27, 2001, which is a continuation-in-part of U.S. patent application Ser. No. 09/752,982, filed Dec. 31, 2000, now U.S. Pat. No. 6,623,635, and a continuation-in-part of U.S. patent application Ser. No. 09/393,437, filed Sep. 10, 1999, now U.S. Pat. No. 6,192,911, issued Feb. 27, 2001, and a continuation-in-part of U.S. patent application Ser. No. 09/520,504, filed Mar. 8, 2000, now U.S. Pat. No. 6,405,387, issued Jun. 18, 2002, and a continuation-in-part of U.S. patent application Ser. No. 09/717,904, filed Nov. 20, 2000, now U.S. Pat. No. 6,426,053.

The instant application is also a continuation-in-part of Applicant's U.S. patent application Ser. No. 10/611,146, filed Jul. 1, 2003, now abandoned, which claims priority from U.S. provisional application No. 60/392,863, filed Jul. 1, 2002.

FIELD OF THE INVENTION

This application relates generally to ozone and ultraviolet light for sanitizing and decontaminating purposes, and particularly for decontamination from hazardous chemicals and biological agents for hazardous materials (HAZMAT) protective suits, vehicle passenger compartments, and other enclosed volumes, and also ultraviolet radiation for decomposing ozone and providing decontaminated air for breathing.

BACKGROUND OF THE INVENTION

Increasing use of hazardous chemicals to make various plastics, pesticides, and numerous other household and industrial products in use today has led to increased risk of contamination of large areas for extended periods due to accidents during transport or manufacturing processes using such chemicals. Industrial environments also require continuous protection for workers in some areas due to risks of exposure to chemical or biological agents in their day-to-day work environment. Unfortunately, there is also an increased risk in modern society for contamination of large areas for extended periods by persistent biological or chemical warfare agents (or other hazardous materials) spread intentionally by terrorists or other individuals or groups.

Risks from accidental spills, terrorist acts, or other potential exposures to biological agents and hazardous chemicals have led to creation of hazardous materials (HAZMAT) response teams equipped with protective suits and protected or self-contained breathing air supplies. Possible use of chemical and biological weapons in modern warfare has also led to development of chemical and biological protective suits and breathing air filters for military and other defense applications. Different types of protective suits are available for use in different environments involving different types of chemical or biological agents. Such suits may be seen, for example, at Internet website www.approvedgasmasks.com.

In the current art, protected breathing air is generally furnished by either a compressed gas cylinder containing a breathable air mixture, or by powered or unpowered air filter units. In some cases, units capable of releasing breathable oxygen via a chemical oxygen generation reaction are used. Compressed gas cylinders, such as those manufactured and marketed as Scott Air Paks™ by Scott Health and Safety, Monroe, N.C. (www.scotthealthsafety.com), support operations in areas or conditions where oxygen may be depleted, as in burning buildings, or in unknown conditions where there is not high confidence that filtration alone can provide non-toxic breathable air. Air filter units typically employ activated carbon filter cartridges, such as those available in various models from the 3M Corporation, Maplewood, Minn., that are capable of filtering and removing numerous chemical compounds from filtered air by adsorption to surfaces of carbon particles, including some called activated carbon or activated charcoal. Some filter cartridges also employ catalysts or other compounds to help neutralize specific contaminants. Generally, air filter units are also capable of removing particulates from air passing through the filter units, including potentially hazardous dust, powder, or smoke particles and many airborne biological agents, such as anthrax spores, airborne bacteria, and the like. Air filter cartridges may be attached directly to the front or sides of air masks, or an air filter unit may be worn on a belt, back, or chest pack and connected to an air mask via a flexible hose. In unpowered filter units, air is typically pulled through filter units in a cyclic manner by pressure differentials created in a mask or mouthpiece by normal inhalation and exhalation respiration pressures of a wearer. In some cases, one-way intake air valves and one-way exit valves on masks provide for one-way air flow through air filter units and prevent contamination or loading of filter units by moisture and other components in a wearer's exhaled breath. Powered air purifying respirator units employ a powered fan or blower to draw or push air through one or more air filter cartridges or other types of filters into a sealed system, and then provide filtered air from the sealed system to a user via a hose, pipe, or other apparatus connected to a mask, mouthpiece, faceplate, helmet, hood, or other device through which protected breathing air is provided to a wearer. Advantages of powered air purifying respirator units include being able to provide filtered air to a wearer at a nominal pressure slightly above atmospheric pressure, which makes it easier for a wearer to breathe without having to overcome air flow resistance of an air filtering cartridge. Slight positive pressure, with respect to atmospheric pressure, provided by a powered respiratory unit also helps maintain positive pressurization within a mask, faceplate, or hood so that any seal deficiencies or other leaks result in an outflow of clean air instead of an inflow of contaminated air. Powered respiratory units are typically powered by one-time use batteries or by rechargeable batteries. Batteries and filter cartridges typically last approximately eight to twelve hours before they must be replaced or recharged.

In case of an accidental or intentional release of hazardous chemicals or biological agents, a general procedure is for HAZMAT teams to respond to a safe area near the release site, generally upwind of any contaminated area, and then don protective gear in the safe region before entering a contaminated area to rescue or recover victims or take actions to reduce or eliminate the hazard or reduce its effects. Such actions, for example, may involve stopping a leak or cleaning up spilled materials. However, the potential widespread nature of some accidents or intentional releases of hazardous materials may make complete cleanup impractical, requiring resumption of critical activities in a partially contaminated region, and the critical nature of some facilities may make it necessary to continue or resume operation even in an environment that still contains significant contaminants. Typically, after an initial response to a scene of a contamination event, testing and analyses of contaminating chemicals or biological agents are performed to characterize such contaminants and permit tailoring of protective measures to be effective against identified contaminants without additional burdens of maintaining protective measures that are not necessary.

Protective gear in current art is generally designed to provide only relatively short term protection while an individual is in a contaminated area. Protection timelines typically range from an hour or so for individuals using self contained breathing apparatus, such as Scott Air Paks™, or up to eight to twelve hours for individuals using powered breathing apparatus, such as the Breathe Easy™ system made by 3M Corporation. Current technologies for providing protected breathing air supplies do not also provide a capability for decontamination of interior surfaces of a protective suit or vehicle compartments, or for decontamination of contaminated clothes or skin of a wearer.

Increasing possibilities of accidents or terrorist acts creating contamination for extended periods over widespread areas by persistent biological or chemical agents make it desirable to have technologies and methods that can support long term operations in contaminated areas and also provide for decontamination of interiors of protected suits and vehicles used in such contaminated areas. In a widespread accident or attack, it may be difficult to find known clean areas within which to don protective suits and other protective equipment. In an accident or surprise attack, victims' clothing or skin may become contaminated before they can escape or don protective equipment. It is thus desirable to have a capability to sterilize or decontaminate interior surfaces of protective suits, as well as a wearer's clothing and skin, after a protective suit has been donned and while it is being worn by an individual. Similarly, since vehicles, including trucks, cars, aircraft, train cars, and the like, already present near a site where hazardous chemicals or biological agents are released, or responding to such a site, may be needed to provide shelter from inclement weather or a contaminating environment, it is desirable to have a capability to decontaminate passenger compartments or other compartments of vehicles used to respond to, operate within, or provide protection from, contaminated areas, as well as a capability to provide breathable air to victims or rescue and cleanup personnel who may need to use vehicles for shelter and transportation. In some situations, there may also be a need to protect pets, food animals such as cattle, pigs, chickens and the like, and other assets and resources requiring decontamination and breathable air during and after releases of chemical and biological agents. Furthermore, since releases of chemical and biological agents may occur at night, or require operations into the night, or in locations that are not well lighted, and may require operations using battery power or other limited power sources, it would also be desirable to be able to generate light in a visible portion of the electromagnetic spectrum using energy from the decontamination and breathable air supply apparatus that might otherwise be wasted. It is further desirable that such capabilities avoid a need for expensive special purpose equipment such as compressors to refill compressed air cylinders, or a need for a massive supply of filter cartridges which must be replaced after only a few hours of use.

The present invention provides innovative designs and methods for decontaminating interiors of protective suits, vehicles, and other enclosures, as well as clothing, skin, and hair of humans and other animals, and for providing purified breathing air to occupants of protected suits or enclosures, or to other humans or animals using embodiments designed just for breathing air, by employing proven germicidal capabilities of ultraviolet radiation as well as proven air purification and germicidal capabilities of ozone and ozonites produced by use of vacuum ultraviolet radiation and Corona discharge techniques. In some embodiments, ultraviolet radiation is also used to break down ozone to make air sterilized by use of ozone, ozonites, and ultraviolet radiation safe to breathe. Additional innovations in the present invention allow realization of benefits noted above with less power and weight than has been required previously in the ozone air purification art, and at lower costs. Other innovations enhance overall efficiency of emergency operations by also generating light in visible portions of the electromagnetic spectrum using ultraviolet light that would otherwise be wasted and contribute to heat generation in a process of generating or destroying ozone.

Past disclosures by Applicant have described generation of ozone and ozonites by use of ultraviolet mercury vapor lamps. Mercury vapor lamps create, within a plasma of an arc discharge, ultraviolet radiation over a range of wavelengths that includes both 185 nm and 254 nm. Mercury vapor lamps having containment tubes made of purified quartz allow passage, with only moderate attenuation, of ultraviolet radiation with wavelengths as short as 185 nm or somewhat less (also referred to as vacuum ultraviolet, or VUV, radiation). A degree of transmission through quartz of radiation having wavelengths near 185 nm through is generally dependent on purity of the quartz. VUV radiation that includes radiation having wavelengths shorter than approximately 200 nm is capable of breaking molecular bonds within diatomic oxygen molecules, freeing mono-atomic oxygen atoms, some of which then recombine with other diatomic oxygen molecules to create ozone molecules, which contain three oxygen atoms. However, it should be noted that, in some contexts, the term vacuum ultraviolet radiation includes wavelengths significantly shorter that 185 nm, and could include wavelengths shorter than approximately 160 nm that cause undesirable, for air purification applications, breaking of bonds and disassociation of diatomic nitrogen molecules in exposed air. Thus, for purposes of this Application, the term "VUV" radiation is hereby defined to include ultraviolet radiation containing wavelengths near 185 nm capable of breaking bonds of diatomic oxygen molecules and promoting production of ozone, but excluding wavelengths short enough to cause undesirable ionization of nitrogen molecules in exposed air. This is a useful operating definition of VUV radiation for purposes herein since wavelengths sufficiently short to cause disassociation of nitrogen molecules are not transmitted significantly even by purified quartz, which is a material used for containment tubes of ultraviolet lamps intended to permit transmission of 185 nm radiation from a mercury plasma discharge. (Other materials, that may be available or that may become available, that transmit both VUV and UV-C radiation and also tolerate exposure to VUV and UV-C radiation, and to temperatures and pressures associated with containment of mercury vapor plasma discharge, could be used in lieu of quartz in various embodiments of VUV lamps of the instant invention.) Ozone molecules, mono-atomic oxygen atoms, and some other compounds and free radicals including hydroxyl radicals, collectively called ozonites, formed during exposure of air, especially air containing normal to high levels of humidity, to VUV radiation, are highly reactive and are capable of breaking down, via oxidation or advanced oxidation processes (AOP), many hazardous chemicals and biological agents flowing in an air stream exposed to VUV radiation. The energetic nature of VUV radiation can also contribute directly to other reactions or breaking of chemical bonds within chemicals or biological agents exposed to such radiation, thereby providing a germicidal action for biological agents and contributing to breakdown of hazardous chemicals into non-toxic or less hazardous compounds. Beneficial decontaminating oxidation reactions of ozone and ozonites continue within an ozonated air stream after exiting a VUV exposure chamber, and in a volume within which a thus ozonated air stream is allowed to flow, and include reactions with contaminants on surfaces and within porous materials. Ozone and ozonites in an ozonated air stream also react with contaminants in air that did not flow through a VUV radiation chamber but which is mixed with ozonated air.

Since it is undesirable for humans and other animals to breathe air containing a high concentration of ozone, Applicant's invention utilizes mercury vapor plasma tubes that emit a spectral line at 254 nm to destroy ozone molecules. However, it should be noted that other sources of ultraviolet radiation, such as lasers and solid state light emitting diodes, having wavelengths shorter than about 300 nm, may also be used to destroy ozone. As such, for purposes of this application, the term "UV-C" radiation is defined as ultraviolet radiation generally between about 200 nm and 300 nm to cause breaking of bonds within, and disassociation of, ozone molecules. As noted earlier, such radiation within this range is also produced within a discharge region of a mercury vapor lamp. When a tube used as a containment tube for a mercury vapor lamp is made of ordinary silicate glass, or doped quartz containing impurities that prevent transmission of VUV radiation, rather than purified quartz, ultraviolet radiation having wavelengths shorter than 240 nm to 250 nm is attenuated strongly within the glass or doped quartz tube while radiation having wavelengths near 254 nm or greater is passed with much less attenuation. Thus, previous disclosures by Applicant have shown how a mercury vapor discharge lamp made with ordinary glass or doped quartz, referred to as a UV-C lamp, may be used in an apparatus to expose air containing ozone to UV-C radiation to reduce ozone concentrations to levels safe for breathing by humans and other animals. In different applications and embodiments described earlier by Applicant, separate VUV and UV-C lamps are operated simultaneously, or separately at different times, in order to produce different effects and concentrations of ozone and ozonites.

Some embodiments of the instant invention may similarly employ separate VUV and UV-C lamps in novel ways to provide for decontamination of interiors of protective suits, vehicles, and other enclosures. Some embodiments may also provide a source of purified and de-ozonated air for breathing by humans or animals. However, as a further innovation that may reduce weight and power needs, or reduce costs, of some embodiments, Applicant also reveals an innovation whereby both creation and destruction of ozone may be accomplished using a single mercury vapor discharge lamp, and additional innovations for some embodiments that will allow light to be generated as a source of illumination, similar to illumination provided by a flashlight or a miner's head lamp, to support operations at night or in dark areas, using energy that would otherwise be wasted in heat generation. For operations at night or in dark locations, an ability to also generate light in the visible or near-infrared portions of the electromagnetic spectrum will help make maximum use of available power, such as batteries carried by an individual.

It is thus one object of the instant invention to provide apparatus and methods for decontaminating interiors of protective suits and vehicles, clothing and skin of personnel, and other assets of at least some categories of hazardous biological and chemical agents. It is another object of the invention to provide purified air for breathing to support short or long term operations in contaminated areas as well as other applications. It is yet another object of the instant invention to provide apparatus and methods whereby humans or other animals contaminated by exposure to biological or chemical agents may be decontaminated before entering a clean zone for habitation or treatment, and whereby humans or other animals infected with biological agents may be maintained in isolation during a period of contagiousness when they might expose others. It is yet a further object of the invention, in some embodiments, to provide a source of visible light. Other objects of the invention will become clear upon a reading of the following specification.

BRIEF DESCRIPTION OF DRAWINGS

FIGS. 5A, 5B, 5C, and 5D are schematic diagrams illustrating alternative embodiments of the instant invention.

FIGS. 9A, 9B, 9C, and 9D are illustrations showing characteristics of fittings that may be used to connect an air hose to a protective suit and to interior air ducts.

FIGS. 10A and 10B are illustrations of end-on and top-down views of a small air duct that may be used to route air within a protective suit.

FIG. 11 is an illustration showing representative characteristics of a fitting that may be used to exhaust air from a protective suit.

FIGS. 13A and 13B are diagrammatic views showing an alternative embodiment wherein both ozone creation and ozone destruction functions may be accomplished with a single ultraviolet tube, with optional features for generation of visible light.

FIGS. 15A and 15B are end-on and sectional views showing one of many types of one-way check valves that could be used with various embodiments of the instant invention.

FIG. 15C is an additional sectional view showing features of an air-flow restrictor based on a check valve as illustrated in FIGS. 15A and 15B.

FIGS. 16A and 16B are illustrations of separate components that may be joined together as illustrated in FIG. 16C to create a one-way valve that could be used with an apparatus as illustrated in FIGS. 14A and 14B.

FIGS. 18A, 18B, and 18C are diagrammatic illustrations of an embodiment of an ultraviolet radiation exposure assembly of the instant invention.

FIG. 19 is a diagrammatic illustration of an alternate embodiment of an ultraviolet radiation exposure assembly of the instant invention.

FIG. 20 is a diagrammatic illustration of an alternate embodiment of an ultraviolet radiation exposure assembly of the instant invention.

DETAILED DESCRIPTION OF THE DRAWINGS

Since some embodiments of the instant invention deal with use of ozonated air circulated within protective suits and vehicles for decontamination, and concurrent or subsequent de-ozonation of ozonated air to provide safe breathing air, Applicant begins explanation of his invention with a review of features of prior art in protective suits and breathing air supplies, and in vehicles, which may be relevant to the practice of some embodiments of the instant invention.

Figure 1B:
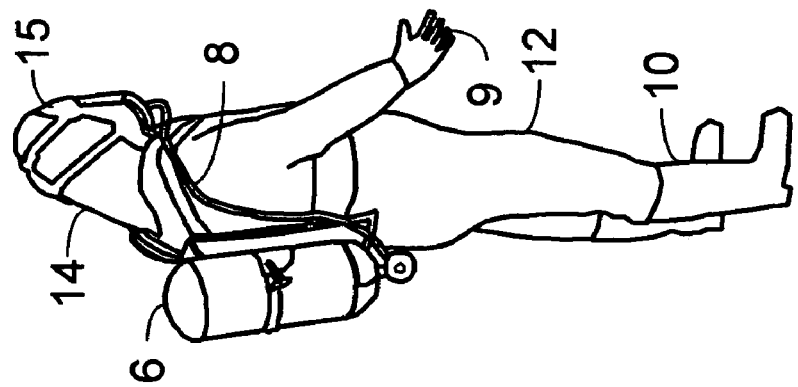
FIGS. 1A and 1B are illustrations of various types of protective suits found in the prior art.
Figure 1A:
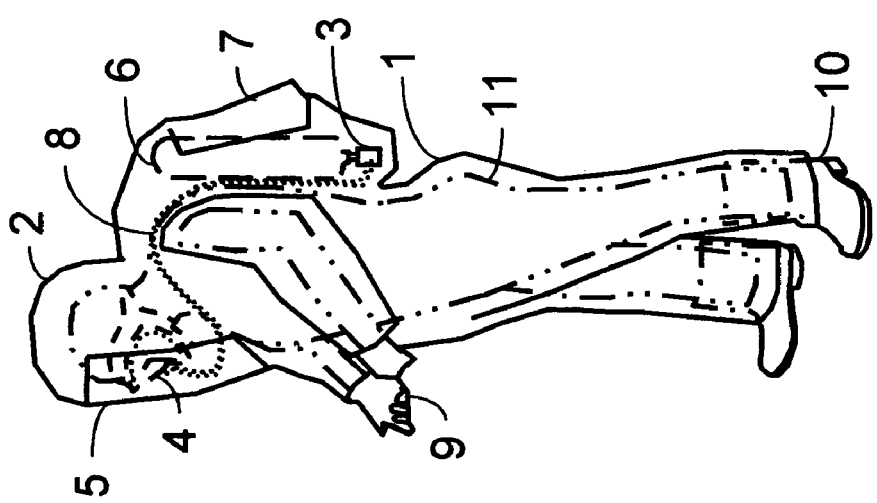
Figure 2:
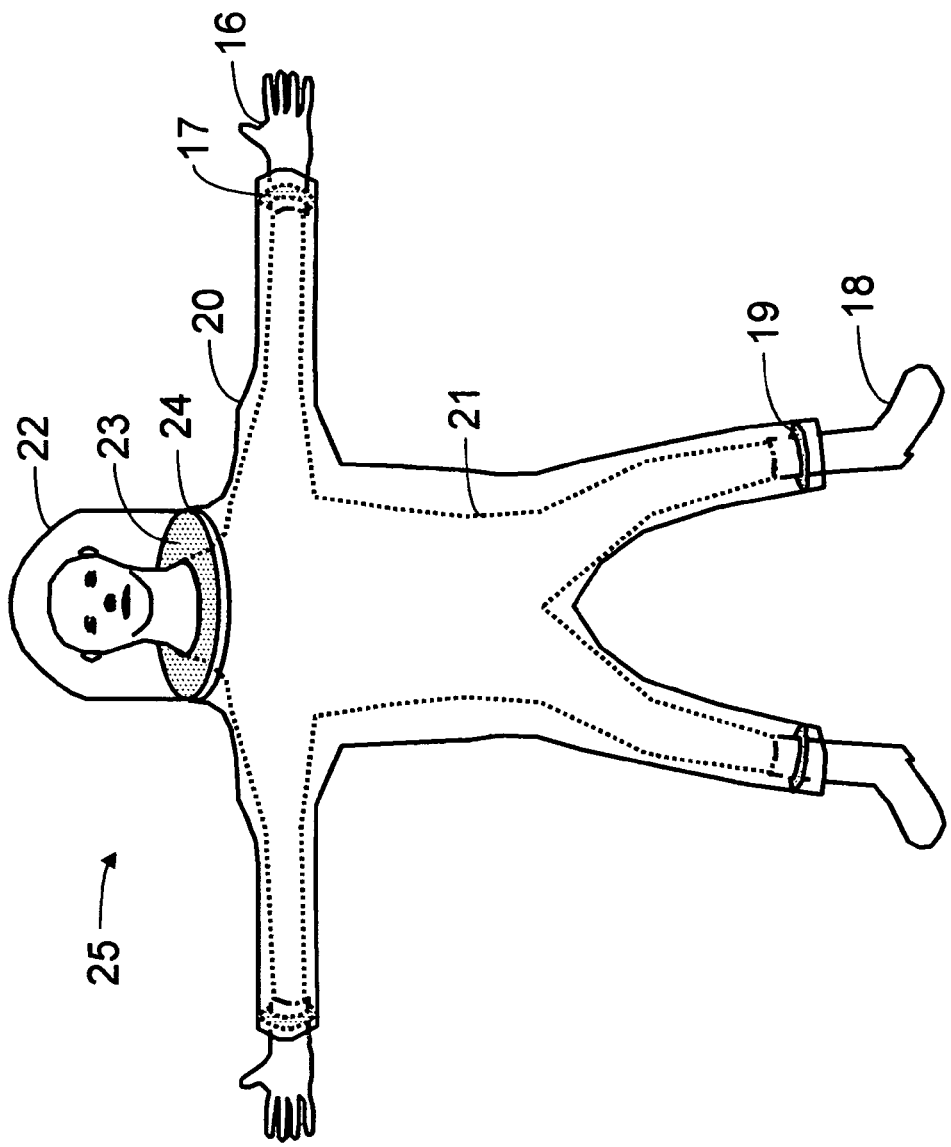
FIG. 2 is an illustration of another type of protective suit found in the prior art.

Currently, HAZMAT protective suits and protected breathing air supplies come in many different forms, some of which are illustrated in FIGS. 1A and 1B, and in FIG. 2. For severe or unknown environments, protective equipment generally includes a self contained breathing apparatus comprising an air tank 6 and pressure regulator 3, air mask 4, and connecting air hose 8, a fully enclosing suit 1, including gloves 9, boots 10, hood 2, and an expansion pouch 7 that also encloses the self contained breathing equipment as illustrated in FIG. 1A. For these dangerous and unknown environments, a responding individual typically dons an air mask 4 that covers a nose, mouth, and eyes of the individual and which is connected to tank 6 that provides oxygen in a suitable air mixture. The individual, who may also be wearing other clothing 11, then enters a fully enclosing suit 1 which is then sealed against the outside environment by use of zippers, elastic cuffs, tape, and other closure mechanisms. In some cases, gloves 9 and boots 10 are constructed as an integral part of a protective suit 1, while in other cases gloves and boots may be donned separately, with elastic cuffs (e.g., 17, 19 in FIG. 2) inside a suit 1, external lacing or straps, Velcro™ fasteners, special fittings, or other sealing or connecting devices, used to provide seals against external threats in the environment.

For some environments and situations, protective suits 12, such as illustrated in FIG. 1B, may include a close-fitting head cover 14 similar, for example, to that of a hooded sweat suit, the head cover being donned first. Then an air mask 15, an air supply 6 and air hose 8 are donned over the suit in a manner that provides a seal around a periphery of mask 15 over close-fitting head cover 14 so that a tight seal is provided for breathing air and so that no skin is exposed to an external environment.

Referring to FIG. 2, a suit 25 topologically similar to space suits used by astronauts may be employed for protection in a hazardous chemical or hazardous biological agent environment. Such suits are generally worn over an undergarment or other clothing 21. These suits make use of a helmet 22 or other enclosure for a wearer's head that seals against a rigid collar ring 24 around the neck region of body suit 20 so that body suit 20 and helmet 22 may be pressurized together relative to external air pressure. In this and other types of suits a neck dam 23 may be employed to protect against entry into body suit 20 of fluids or contaminants when a helmet 22 or similar head cover is removed. For example, a neck dam was used in space suits of early U.S. astronauts to prevent entry of water in case an astronaut in a space suit ended up in an ocean or other water without a helmet during post-reentry recovery operations. A neck dam typically is constructed of a relatively impervious material generally in a shape of a large washer with a hole in the center for a wearer's neck and typically attached on its outer periphery to the inside of a rigid collar ring, or to other portions of the suit near the ring. The neck dam may be made of a stretchable material, or may have one or more seams or zippers that can be opened temporarily, as to allow an individual to insert his or her head through a hole or opening in a center of the neck dam during a process of donning a suit 20. The opening in the center of a neck dam is then sealed against a wearer's neck by its elastic action, by use of laces, zippers, or drawstrings, or by use of Velcro™ or stretchable tape or adhesive tape to help prevent entry of undesired fluids or other contaminants into lower portions of a suit while a helmet is removed. Although originally developed to prevent entry of water or other contaminants into a suit having a rigid collar when a helmet thereof was removed, a version of a neck dam 23 as shown in FIG. 2 may be important in some embodiments and applications of the instant invention, as discussed later herein, to prevent or minimize flow of air between an interior of body section 20 and an interior of helmet 22. In this type of suit 25, wherein the wearer may not wear a separate gas mask, breathing air may be provided through connections in helmet 22 or through connections to suit 20 in a collar area just above neck dam 23 but below rigid collar 24 sealing and locking mechanism for helmet 22.

For reasons that will become clear after the following descriptions of how embodiments of the present invention may be used, it will be seen that it may be desirable to modify some protective suits of the present art, such as those similar to that illustrated in FIG. 2, to add or reinforce neck dams 23, elastic neck cuffs, drawstrings, or other features that will allow a body section 20 of a suit to be sealed against a neck of a wearer to prevent excessive loss, around a wearer's neck, of ozonated air pumped in a suit for purposes of decontamination, as explained below. Also, some suits may be modified to prevent mixture of ozonated air used to decontaminate an interior of a suit with de-ozonated air provided as breathing air to a wearer. It may also be desirable for some designs and applications of protective suits, such as those illustrated in FIGS. 1A and 1B, to add neck dams or similar sealable neck cuffs to these suits to minimize loss of ozonated air. However, for these type of suits, breathing air to a wearer is generally provided via a close-fitting face mask so risks of mixing breathing air with ozonated air used to decontaminate a suit is eliminated or minimized.

Some suit designs have been proposed (Grilliot et al, U.S. Pat. No. 5,572,991, issued Nov. 12, 1996) for interfacing a self contained breathing air supply with a suit so as to provide for circulation of exhaled or other air through channels or other air passageways between layers in a protective suit to act as a coolant, with a stated intention of reducing heat load on a suit occupant. However, designs contemplated by Grilliot generally employ air channels made within layers of suit materials and do not provide for decontamination of interior surfaces of a protective suit or of a wearer's clothing or skin.

It is generally desirable that breathing air provided through a mask 4, 14, hood or helmet 22 be at a slightly increased positive pressure with respect to external atmospheric pressure so that a generally outward flow of air at poor seals, small tears, or other potential leaks will prevent inflow of contaminants. However, some air mask designs rely on a tight seal around a wearer's face and one-way valves so that negative pressure created within such a mask during a wearer's inhalation can be used to draw air through a filter without a need for regulated pressurization (as with a self contained breathing apparatus) or powered pressurization (as with a powered air purifying respirator or similar device as discussed earlier).

Figure 3:
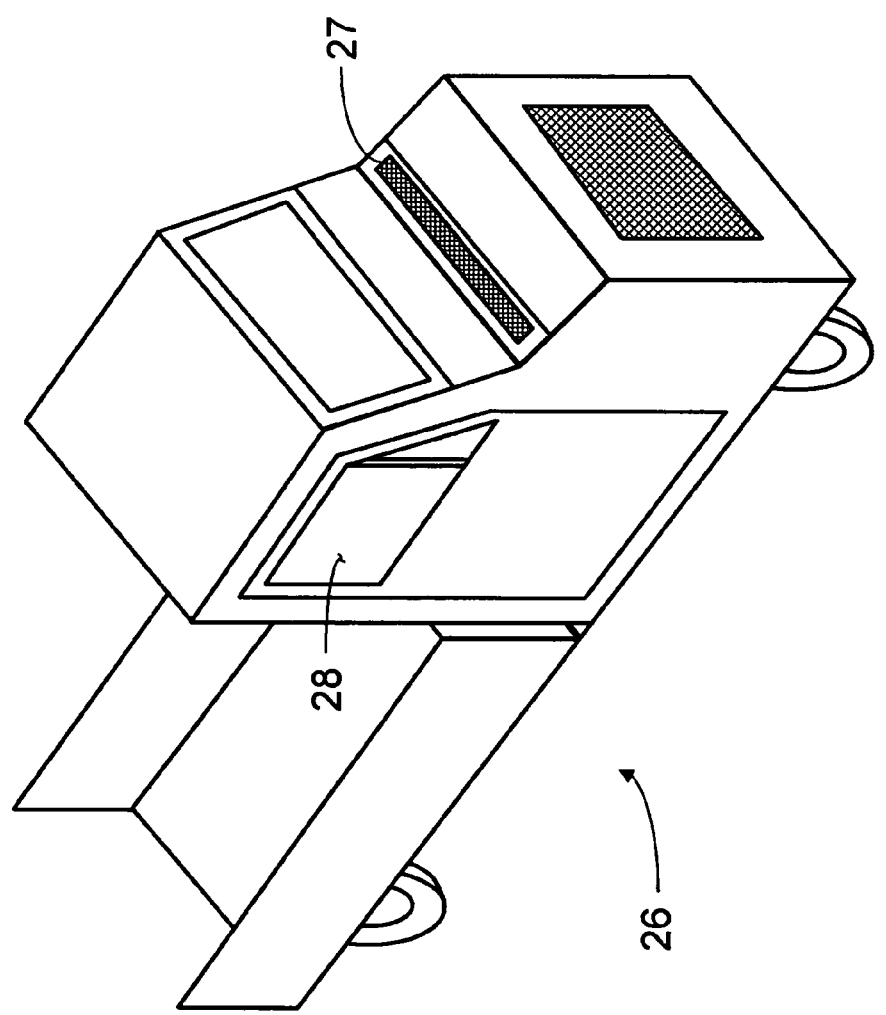
FIG. 3 is an illustration of a vehicle used to point out certain features found in the prior art.

As noted in the BACKGROUND, and referring now to FIG. 3, vehicles 26 such as trucks, cars, aircraft, train cars, and the like may be contaminated during a chemical or biological accident or attack, but may also be needed for protection from these or other inclement environments, or for transportation. It is thus desirable, and an object of some embodiments of the instant invention, to provide decontamination of passenger or other compartments of vehicles, and, in some embodiments, to also provide safe breathing air for occupants of such vehicles, even while an interior of a vehicle is being decontaminated. To support subsequent discussions of how some embodiments of the instant invention may be interfaced to and used with vehicles, some features common to many vehicles are noted in FIG. 3. These features typically include side windows 28 which may be opened by some amount and passenger compartment air intake vents 27 such as commonly found just below windshields of many automobiles or trucks. In some vehicles, these vents are located below rear portions of engine compartment hoods. Other features common to many vehicles but not illustrated explicitly in FIG. 3 include air circulation fans or blowers such as used with heaters or air conditioning systems and sources of power (generally 12 or 24 volt DC power) such as generally provided in a form of a cigarette lighter socket or other electrical plug or connection device. These features are of interest since some embodiments of the instant invention may be designed to operate in conjunction with, or obtain power from, such features. In some vehicles, it may be necessary to obtain power to operate an embodiment of the instant invention directly from a battery or by splicing into a power circuit within a vehicle. However, some embodiments of the instant invention may be operated from other power sources such as generators, fuel cells, solar cells, batteries, or commercial AC power.

Many embodiments of the present invention may be designed or adapted to interface with protective suits 1, 12, 25, vehicles 26, and other equipment already in present art. However, other embodiments may employ suits specially designed with additional features (e.g., flexible solar cells or panels, flexible plastic battery panels, special cuffs, neck dams, fittings, harnesses, or interior air ducts) used to support or optimize features, applications, and performance of embodiments of the instant invention.

Having shown some features of existing protective suits and vehicles that may be exploited in the practice of some applications of the instant invention, Applicant now describes principles and innovations that are employed in various embodiments of the instant invention.

As noted in the BACKGROUND, it has been established in prior art, and in prior disclosures by the Applicant that ultraviolet light, ozone, and ozonites may be used to kill or incapacitate various biological pathogens and to break down many hazardous or undesirable chemicals that are susceptible to oxidation or advanced oxidation processes (such chemicals are referred to in some literature as pyrogens). An ability of ozone and ozonites to provide germicidal action against many biological agents, and to break down many potentially contaminating chemical compounds, including many chemical warfare agents, subject to the strong oxidation potential of ozone and ozonites, including hydroxyl radicals, is well known in the art.

In order to provide for both decontamination of a protective suit or other enclosure while also providing safe breathing air for one or more occupants, some embodiments of the instant invention provide two basic air flow paths—one path containing ozonated air being used for decontamination, and another path containing de-ozonated air suitable for use as breathing air. As will be shown in various embodiments, these air paths may be interconnected sequentially in space, time, or both space and time, or the paths may be interconnected in a somewhat parallel fashion with some path segments being common to an ozonated path and a de-ozonated path. In various embodiments, either path may be implemented as a one pass open loop, a multi-pass closed loop, as a "leaky" open or closed loop, or some combinations thereof.

Figure 4:
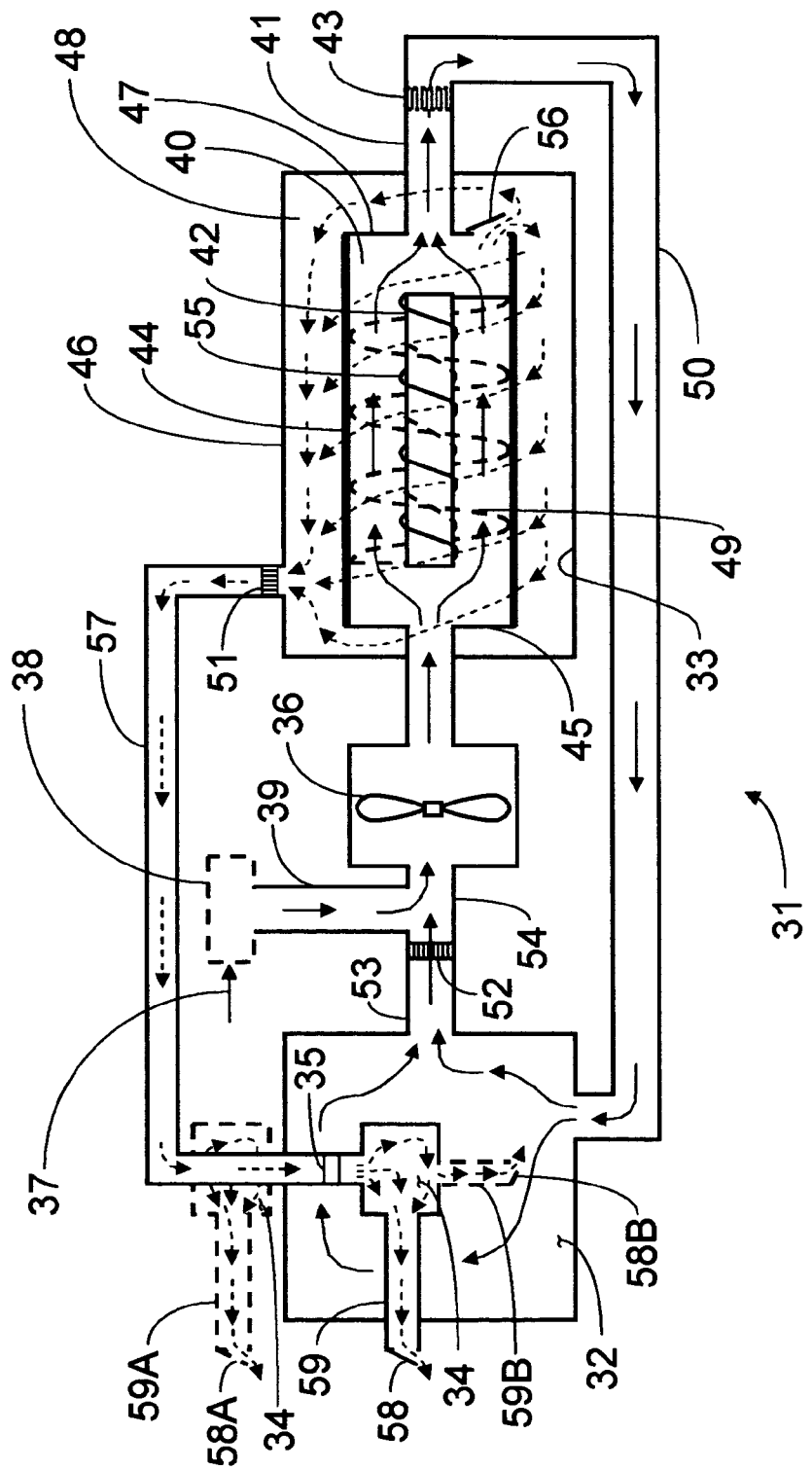
FIG. 4 is a partly schematic, partly diagrammatic illustration of features of an embodiment of the instant invention.

FIG. 4 schematically illustrates one potential embodiment, with optional variations, and is used to support the following discussion of principles of operation that may be employed in various embodiments of the instant invention. FIG. 4 with its options is representative of many embodiments that may be implemented employing concepts and innovations of the instant invention. FIG. 4 is illustrative of how some principles disclosed earlier, as well as new innovations, may be integrated in some embodiments of the instant invention to provide a capability to decontaminate an enclosed volume of chemical or biological agents, which may be occupied, while also providing decontaminated and de-ozonated breathing air to any occupants. FIG. 4 also illustrates an innovative way in which both ozone creation and destruction may be accomplished using a single mercury vapor ultraviolet lamp, and how further innovations may be added in some embodiments to support generation of visible or near-infrared light for illumination, using ultraviolet light that might otherwise be dissipated only as waste heat energy.

Still referring to FIG. 4, a contaminated or possibly contaminated volume 32 that needs to be decontaminated of chemical or biological agents may also be occupied by one or more humans or other animals that require a supply of breathable air within a generally more limited breathable air volume 34 within which contaminants as well as ozone have been reduced to safe levels for breathing.

One approach for decontaminating a volume 32 of chemical and biological agents is to use an ozone generator to generate ozone and ozonites in a volume of air and then move air containing ozone and ozonites into volume 32 to allow ozone and ozonites to react with and neutralize contaminants. Safe breathing air for humans and animals may be produced by extracting a portion of air in which contaminants have been reduced by use of ozone, ozonites, and ultraviolet light, and then using UV-C radiation to reduce ozone to safe levels for breathing (while also provide additional germicidal action), and providing de-ozonated air for breathing via air masks, breathing hoods or helmets, or other suitable apparatus. It should be noted here that, in general practice of the invention, an apparatus of a selected embodiment is connected via air hoses or other air passageways to either or both of a volume 32 to be decontaminated and a volume 34 in which breathable air is desired. For many applications of the instant invention, a combination of either or both of a volume 32 and a volume 34 with an apparatus representing a selected embodiment operate together to form an integrated system that may, in general, be viewed as having two basic air flow paths or circuits—a decontamination circuit, represented in FIG. 4 using solid line arrows to represent air flow, and a breathing air circuit, represented in FIG. 4 using dashed line arrows to represent air flow. A decontamination air flow path and a breathing air path may be implemented in different embodiments as an single pass open-loop path, a multiple pass generally closed-loop path, a "leaky" open or closed loop path, or some combination of paths. Paths for decontamination and for breathing air may be interconnected serially or sequentially, or may share some sections in a somewhat parallel or mixed flow sense. Selection of features revealed herein for a given embodiment should generally be governed by physical characteristics of a volume 32 to be decontaminated (i.e., whether a volume 32 is enclosed by a flexible boundary, such as a protective suit made of flexible materials, a rigid enclosure such as a box or sealed room, and whether an enclosure is leaky or airtight), and by the nature of the chemical or biological agents that may be encountered in a given application (e.g., whether an agent is extremely dangerous, requiring very high confidence in neutralization, or whether an agent is basically an irritant or nuisance, but not extremely dangerous, requiring reduction of concentration and effects but requiring less confidence in complete neutralization). Specifically, characteristics of a volume 32 to be decontaminated influence needs and positions for air movement or compression devices, such as fans, needs and positions for air-flow restrictors or pressure regulators, and similar features. Sufficient information is provided herein to allow practitioners skilled in relevant arts to make appropriate trade-offs and selection of the various features of the instant invention to tailor embodiments of the instant invention and realize benefits for various applications.

Referring again to FIG. 4, air used to generate ozone may be drawn from volume 32 to be decontaminated but may also be drawn from another source 37 of air containing oxygen. Source 37 may be ambient air generally surrounding a volume 32 to be contaminated (also referred to elsewhere herein as outside air) or, for some severe environments, source 37 may be breathable clean air containing oxygen, or concentrated oxygen, from a self contained breathing apparatus tank, powered breathing apparatus, facility air supply, or the like. For most applications involving enclosures that are not rigid (including most protective suits) or that are not completely air tight (including passenger compartments of most vehicles), air will be drawn from an external source into an ozone generator where ozone will be created within an air stream that will then be directed into a suit or other enclosure to be decontaminated. Exposure within an ozone generator to VUV radiation of air withdrawn from contaminated volume 32, or potentially contaminated air from an external source 37, will provide germicidal benefits against contaminating micro-organisms, and the combination of ozone and ozonites generated within a VUV exposure chamber will react with contaminating chemicals and micro-organisms to reduce or eliminate their harmful chemical or biological properties. In some embodiments, ozonated air from a suit or other enclosure is then recirculated through an ozone generator in order to enhance concentrations of ozone and increase decontamination capabilities. In order to provide breathing air for occupants, a portion of air that has been treated with ozone and with ultraviolet light may be withdrawn (e.g., via one-way valve 56 in FIG. 4) from an ozonated air stream and moved through a chamber (e.g., chamber 48 in FIG. 4) where it is exposed to UV-C radiation in order to break down ozone and to also provide further germicidal benefit to help make the air thus withdrawn safe to breathe.

Elements of an embodiment of the instant invention are represented schematically in FIG. 4. Some of the many possible variations and alternate embodiments are also shown. A principal embodiment illustrated in FIG. 4 employs innovations allowing use of a single ultraviolet lamp for both ozone creation and destruction. Other embodiments employing separate VUV and UV-C lamps are illustrated in subsequent figures. The embodiment and options illustrated in FIG. 4 include a VUV lamp 42, a VUV exposure chamber 40 generally surrounded and defined by walls 44 of glass, represented in FIG. 4 by thickened lines, a UV-C exposure chamber 48 between glass walls 44 and outer walls 46, and end caps or walls 45, 47 for VUV chamber 40. An opening which may include a spring-loaded valve 56, which may also be a one-way valve, permits flow of air from chamber 40 into chamber 48 when pressure differentials exceed spring-loading pressures on valve 56. A fan 36 or other air movement or compression device is provided, and various air passageways provide for flow of air between and among other elements of the instant invention, including, for example, air passageway 39 and optional filter or humidifier 38 that provides for optional filtering and humidification. A flow of air is provided from an outside source 37 into VUV exposure chamber 40 via air passageway 54, and air passageways 41, 50 provide for flow of ozonated air from VUV exposure chamber 40 back to contaminated volume 32 through air passageway 54. The fan 36 forces an ozonated air circulation flow between chamber 40 and volume 32 for re-exposure and re-circulation. An air passageway 57 provides for flow of de-ozonated air from a UV-C exposure chamber 48 to one or more breathing air volumes 34.

In some embodiments, as illustrated in FIG. 4, both creation and destruction of ozone may be accomplished by use of a single mercury vapor discharge lamp 42 having a containment tube made of quartz, which transmits VUV radiation in addition to UV-C radiation from the discharge plasma. This single VUV lamp 42 may be used in conjunction with one or more separate pieces of silicate glass 44 that serve as a chamber wall for a UV-C exposure chamber 48 and also as a filter to preferentially block transmission of VUV radiation while allowing passage of UV-C radiation into UV-C exposure chamber 48 separate from VUV exposure chamber 40 of an ozone generation and treatment unit. Glass 44 may be in a form of a cylinder of glass placed more or less concentrically around a VUV lamp 42, but may also be in other forms. Other materials, such as FEP plastic, or quartz with selected impurities added (hereinafter, "doped quartz"), which transmit UV-C radiation but attenuate VUV radiation, may be used in place of silicate glass 44 to provide selective transmission of UV-C radiation in this and similar applications described in this Application, VUV lamp 42 may also be a hybrid lamp including a coil 55 to enhance efficiency as disclosed previously in Applicant's U.S. Pat. No. 6,426,053, issued Jul. 30, 2002, and in Applicant's U.S. Pat. No. 6,951,633, issued Oct. 4, 2005. In operation, a portion of an ozonated air stream may be caused to exit VUV exposure chamber 40 and flow into UV-C exposure chamber 48 by pressure differences in air passageways entering or exiting VUV and UV-C exposure chambers, or by action of control valves added at appropriate points, illustrated later herein, to control and provide desired air flow paths for different modes of operation. When air containing ozone is passed through UV-C exposure chamber 48, ozone molecules in the air are broken down by UV-C radiation. An ability to control destruction as well as generation of ozone using a single VUV lamp may be beneficial in terms of reduction of cost, weight, or power in many applications of ozone, including some disclosures provided previously by Applicant, and will also be beneficial for some embodiments of the instant invention described herein.

Embodiments of the instant invention may include an air flow restriction device 52, which may be a spring-loaded one-way valve as illustrated later herein, or simply a restricted air passageway, and in some embodiments may also contain a carbon-dioxide scrubber or rebreather, positioned in air passageway 54 between a contaminated volume 32 and an air passageway 39 for admitting air from an external source 37 into a general air flow of the device as indicated by solid line arrows within the chambers and air passageways. Air flow restriction device 52 may be used to help create and maintain a positive pressure, relative to normal atmospheric pressure, within contaminated volume 32 and to also create a pressure drop, relative to an external air source 37, so that external air may be drawn into system 31 and prevented from entering a contaminated area 32 before flowing through a VUV exposure chamber 40. Use of an air flow restriction device 52 is more important in embodiments used in applications wherein contaminated volume 32 is within a non-rigid protective suit so that some degree of inflation may be maintained within the suit to provide enhanced air flow and to prevent such a suit from being drawn tight against the skin and other clothing of the wearer. Even in applications and embodiments wherein a contaminated volume 32 is a rigid volume such as a passenger compartment of a vehicle or a protective suit with ribs, stays, and other structure capable of maintaining its shape relatively independently of air pressure, it may be desirable to use an air flow restriction device 52 to maintain a positive pressure created within a contaminated volume to help prevent any influx of additional contaminants from outside air that may otherwise be drawn in through cracks, seams or other leaks. In other embodiments, for example, wherein a contaminated volume 32 is a rigid, well sealed volume, an air flow restriction device 52 may not be needed or desirable. In such an embodiment, air circulation may be maintained by a fan 36, the air circulation being driven around a primary loop comprising VUV chamber 40, an air movement device 36, and a contaminated volume, connected by suitable air passageways, with makeup air drawn from an external source 37 only as needed to replenish air exhausted from the breathing air circuit via respiration of occupants and expiration of breathing air from the system 31 via a breathing air exit passageway 59 and an exhaust port 58, which may be a one-way valve to prevent ingress of contaminants into breathing air via a breathing air exhaust port. In some embodiments, however, a one-way valve may be located adjacent to volume 34, with little or no additional exit passageway 59.

In some situations and embodiments, contaminated volume 32 may be an interior region of a protective HAZMAT suit or a passenger compartment of a vehicle. Breathable air volume 34 may be an air volume within a face mask, hood, helmet, or other device used to separate and isolate breathable air from possibly contaminated ambient air. Topologically, breathing air volume 34 may be located within a contaminated volume 32, as in an embodiment providing breathing air via flexible air hoses and face masks to occupants of a contaminated passenger compartment of a vehicle, or to an occupant of a protective suit such as those shown in FIG. 1A, 1B and FIG. 2. Alternatively, as shown by a dashed box in FIG. 4, a breathing air volume 34 may be located external to a contaminated volume 32, as in the case of air volume in a helmet of a protective suit such as illustrated in FIG. 2 that employs a neck dam to provide a seal to separate a breathable air volume in a helmet from a possibly contaminated volume in a body section of a suit. Air exhaled or otherwise exhausted from a breathing air volume 34 may be directed, generally via use of air passageway 59 and a one-way valve 58 to outside air, as illustrated by solid lines in FIG. 4, or may be directed by an air passageway 59B and one-way valve 58B back into and released within a contaminated volume 32, as illustrated by dashed lines, or in other portions of a decontamination air flow circuit to permit recovery and reuse, for example, of humidity in exhaled air. Depending upon whether a system comprising volume 32 or volume 34 and an embodiment of the instant invention is airtight or leaky, and oxygen replenishment provided by a source 37, an optional carbon-dioxide scrubber or rebreather may be implemented within some embodiments to absorb carbon dioxide and permit safe recovery and recirculation of oxygen from air exhaled by a human or animal being served by an embodiment of the instant invention. Where used, a carbon-dioxide scrubber or rebreather should generally be placed between a point where exhaled air is introduced into a decontamination air flow path and a VUV exposure chamber 40 employed in that path so that recovered humidity and oxygen are available to contribute to generation of ozone and ozonites with a VUV exposure chamber 40. For example, a carbon-dioxide scrubber or rebreather could be placed adjacent to an air-flow restrictor 52, or made to also serve the function of an airflow restrictor.

In order to increase transit path length and exposure duration for contaminants flowing through VUV exposure chamber 40 and also improve control of flow paths and enhance concentration levels of ozone and ozonites produced in air f lowing through chamber 40, which factors combine to increase confidence in destruction of airborne chemical and biological contaminants flowing through chamber 40, one or more baffles 49 may optionally be added within chamber 40 to generally increase the path length followed by air flowing through chamber 40. In general, baffles 49 should be relatively thin sheets of a material such as quartz, glass, or metal tolerant to exposure to VUV radiation, and exposure to ozone and ozonites, without substantial loss of key chemical or physical properties and without contributing undesirable compounds to air flowing through chamber 40 due to outgassing or chemical reactions, and without contributing significantly to loss of ozone due to reactions. Baffles may employ materials or coatings that are either reflective for VUV radiation or that serve as catalysts to promote creation of ozone or promote other desired reactions within VUV exposure chamber 40. In general, baffles 49 should also be designed so that their thin dimension is generally parallel to the long axis of VUV lamp 42 and their other dimensions are generally perpendicular to the long axis of VUV lamp 42 so that shadowing of air flowing through chamber 40 from ultraviolet light emitted by VUV lamp 42 is minimized. A helical shape, similar to a helix of an Archimedes screw or flutes on a drill bit, as illustrated for a baffle 49 in FIG. 4, is one shape that provides desirable characteristics for a baffle 49, although it should be apparent that many configurations of baffles may be used to create a longer and turbulent air path through chamber 40. The pitch, or number of turns per unit length, of a helical baffle 49 may be increased or decreased to increase or decrease, respectively, exposure durations for air flowing through chamber 40. Baffles may be made as an integral part of a shape of VUV tube 42, or may be made as one or more separate pieces that can be inserted into an exposure chamber 40. Baffles may also be designed to be integral and compatible with other features of a VUV lamp 42. For example, FIG. 4 illustrates how use of an additional coil winding 55 to enhance lamp efficiency, as disclosed in Applicant's U.S. Pat. No. 6,426,053, issued Jul. 30, 2002 and in Applicants U.S. Pat. No. 6,951,633, may be integrated with a helical baffle. Dimensions of exposure chamber 40 transverse to direction of air flow affect concentration of ozone produced in a given chamber since attenuation of VUV radiation by absorption in air is significant, leading to significant falloff in intensity of VUV radiation with distance in air from a VUV source. For example, around a cylindrical VUV lamp 42, appreciably higher concentrations of ozone will be produced in air parcels or flow immediately adjacent to VUV lamp 42 than in air parcels further removed (radially, in this example) from lamp 42. Falloff of VUV intensity is such that transverse dimensional differences of one-quarter inch to one inch can appreciably affect concentrations of ozone produced in a given embodiment of a VUV exposure chamber 40. Since higher concentrations of ozone generally provide higher confidence in destruction of contaminants flowing through exposure chamber 40, and in enclosed volumes 32 treated by ozonated air, smaller transverse dimensions of VUV exposure chamber 40 may be used in embodiments of the instant invention intended to be used with more hazardous biological and chemical contaminants. In some embodiments, baffles may separately or also be designed to promote turbulent, rather than laminar, air flow within chamber 40, particularly adjacent to VUV lamp 42, to enhance mixing of ozone, ozonites, and contaminants within air flowing through chamber 40, and to enhance direct exposure of all sides of particulates, including large organic molecules and pathogens, flowing through chamber 40 to ultraviolet radiation to enhance germicidal and other effects of ultraviolet radiation. For similar reasons, holes, ports, or nozzles used to introduce air into VUV exposure chamber 40 in various embodiments may also be designed to promote vortices and other turbulent flow in air streams flowing through VUV exposure chamber 40. Instead of baffles, air being exposed to VUV or UV-C radiation could be made to flow through a helical tube made of a material that transmits, respectively, VUV or UV-C radiation without undue attenuation. Quartz is a material commonly used where transmission of VUV radiation is a desired characteristic and could be used to form a helical tube around VUV lamp 42 for benefits noted above. However, difficulties and costs associated with forming quartz materials into complex shapes generally weigh against use of helical quartz tubes for air being exposed to VUV radiation. On the other hand, ordinary silicate glass or FEP or TFE plastic, which blocks VUV radiation but transmits UV-C radiation with little loss, may be formed into helical or other complex shapes with relative ease. Thus, for air being exposed to UV-C radiation for purposes of de-ozonation and germicidal benefits, a helical tube made of silicate glass or other material such as soft glass or FEP plastic that transmits UV-C radiation with little attenuation may be used to provide a helical flow path or other path that enhances exposure of air to UV-C. Although not explicitly illustrated in FIG. 4, it should be evident that an optional helical baffle or other baffle design, or a helical tube made of glass, FEP, or TFE (variants of Teflon™) as disclosed in Applicants U.S. patent application Ser. No. 10/611,146, filed Jul. 1, 2003, now abandoned, which is incorporated herein by reference, or similar device may also be used in conjunction with, or in place of, a UV-C exposure chamber 48 to increase control of air flow path, and enhance path length, through a UV-C exposure region. Use of such a baffle would improve control of, and confidence in, de-ozonation and germicidal processes that occur in a UV-C exposure chamber such as chamber 48 in FIG. 4. Since attenuation of UV-C radiation in glass and in air is much less severe than attenuation of VUV radiation, performance of a UV-C chamber used to eliminate ozone is less sensitive to transverse chamber dimensions than performance of VUV chambers used to produce ozone, so more flexibility exists in implementation of a UV-C chamber 48 or similar UV-C exposure region using, for example, a helical glass tube. One or more additional wraps or layers of a helical glass tube around a VUV or UV-C lamp may be used to further increase exposure path length if needed for some applications to decrease ozone concentrations to acceptable levels. Even if wrapped directly around or near VUV lamp 42, silicate glass or FEP or TFE plastic used in a helical glass tube will absorb VUV radiation and permit passage of UV-C, creating an efficient UV-C exposure chamber for air flowing through such a helical glass tube. Thus, in an embodiment such as illustrated in FIG. 4, use of an ozonated air exit port 56 and a glass wall 44 to create a UV-C exposure chamber 48 could be replaced with a helical glass tube wrapped concentrically around VUV lamp 42. A valve or port located at one end of a helical glass tube and similar in function and location in the ozonated air flow path to valve 56 could be used to draw air from exposure chamber 40 into the helical glass tube. Ozonated air thus introduced into and flowing within the helical glass tube will then be exposed to UV-C radiation from VUV lamp 42 while being shielded by the glass in the helical tube from exposure to VUV radiation, and thus provide de-ozonated breathable air to an air passageway 57.

Another innovation that may be incorporated into some embodiments of the instant invention is the use of glass or other transparent or translucent (for visible and near-infrared radiation) material as the outer wall 46 of chamber 48, and the addition of chemical elements or compounds, normally called phosphors, that can be excited by ultraviolet radiation and caused to emit light in visible or near-infrared portions of the electromagnetic spectrum. Using techniques and constructions similar to those disclosed in Applicant's U.S. Pat. No. 6,428,756, issued Aug. 6, 2002, phosphors 33 may be coated on a surface of, or mixed within the structure of, a glass or other material comprising outer wall 46, so that phosphors 33 may be excited by UV-C radiation present in chamber 48 and emit visible or near-IR light that travels through transparent or translucent outer wall 46 or other protective coatings or layers to provide illumination to support operations in an area where a protective suit or other enclosure 32 is being used. Normally, phosphors would be selected to provide visible light, but phosphors emitting light in a near-IR portion of the electromagnetic spectrum may be selected for embodiments intended for use during clandestine operations, such as military special forces operations. If phosphors are placed on an interior surface of outer wall 46, an additional coating or layer of glass or other material may be needed over phosphors 33, as illustrated later in FIGS. 13A and 13B, to prevent particulates from phosphors 33 from entering an air stream for breathing air, indicated by dashed air flow arrows in FIG. 4. A material used between a UV-C source 42 and phosphors to coat or protect and retain phosphors must be transmissive for UV-C radiation and should be tolerant of exposure to UV-C radiation without significant damage or harmful out-gassing. Phosphors may be placed on an outer surface of outer wall 46 in some embodiments if outer wall 46 transmits UV-C radiation with little attenuation, but such phosphors would likely still require a transparent (to visible or near-IR) protective coating to prevent abrasion damage to a layer of phosphors. For safety reasons, a preferred approach is to use a layer of phosphor materials thick enough to interact with and stop virtually all UV-C and VUV radiation, and provide a layer of glass or other material transparent to visible or near-IR wavelengths, but nearly opaque to UV-C and shorter wavelengths, outside (from the direction of the ultraviolet lamp 42) the layer of phosphors to prevent escape of UV-C or VUV radiation to an external environment where such radiation may cause eye damage or other undesirable effects.

Figure 4A:
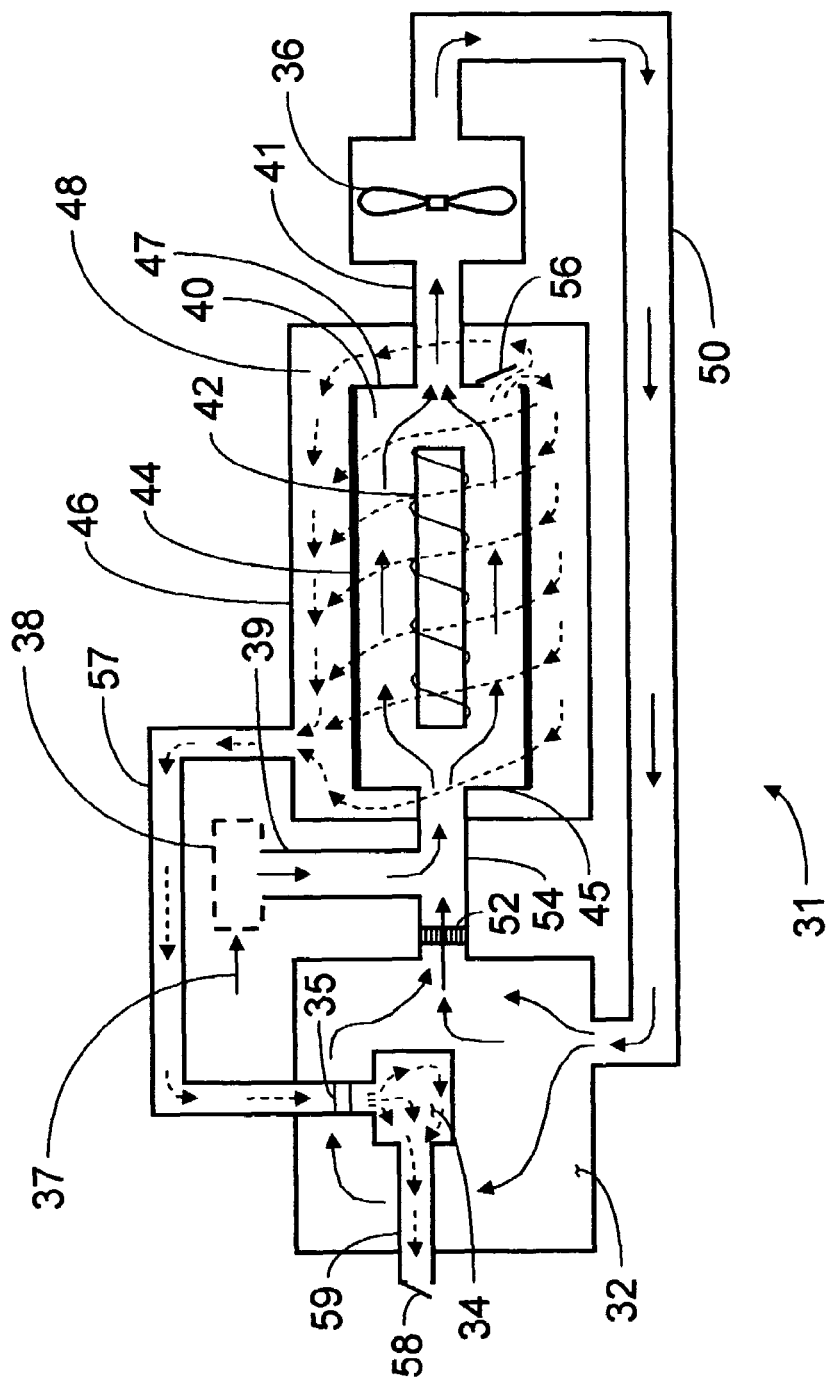
FIG. 4a is a partly schematic, partly diagrammatic illustration of features of an embodiment of the instant invention.

Applicant now calls attention to some other aspects of a principal embodiment illustrated in FIG. 4, and compares benefits and tradeoffs for the illustrated embodiment with alternative embodiments, such as illustrated in FIG. 4A and elsewhere herein, which may also be used with benefit for other applications and considerations. One important aspect in many embodiments is use and placement of air movement or compression devices, such as represented by a fan 36 in FIG. 4 and also in FIG. 4A. One significant difference between embodiments illustrated in FIG. 4 and FIG. 4A is placement of a fan or other air movement or air compression device relative to VUV exposure chamber 44, a port or valve 56 for withdrawal of ozonated air to be de-ozonated to provide breathing air, UV-C exposure chamber 48 (or similar UV-C exposure tube as discussed above), and other elements of an embodiment and volume 32 and volume 34. For an embodiment as illustrated in FIG. 4, an optional fan 36, or another type of air movement or air compression device, is placed before or upstream (in the sense of air flow direction) VUV exposure chamber 40, and downstream of an entry port and optional filter or humidifier 38 for a source 37 of air or purified oxygen. This placement of a fan 36 will result in a somewhat increased air pressure within VUV chamber 40 relative to other pressures within the ozonated air paths and de-ozonated (breathable) air paths explained earlier. Increased pressure within VUV exposure chamber 40 will generally increase efficiency for production of ozone and ozonites within chamber 40. Further increases in pressure within chamber 40 may be obtained by use of a compressor rather than a fan 36 in the location illustrated for a fan 36, along with optional air flow restrictors 51 and 43, which may also be implemented as pressure regulators, that help maintain higher pressure within chambers 40 and 48, while allowing reduced pressures in passageways 50 and 57, and in volume 32 and volume 34. Port 56, that allows flow of ozonated air from the ozonated air path into a UVC exposure chamber 48 or similar region to be de-ozonated to provide breathable air, may also be replaced with a pressure regulator to provide a different pressure in UV-C exposure chamber 48 than in VUV chamber 40. Placement of an air movement device at the location indicated by fan 36 in FIG. 4 will allow breathable air to be provided via air passageway 57 at a positive pressure with respect to supply 37, which will be at normal atmospheric pressure in many applications. As noted earlier, providing breathing air at a slight positive pressure with respect to atmospheric pressure will generally make breathing easier and also help prevent entry of contaminants through bad seals or other leaks.

FIG. 4A illustrates an alternative placement for fan 36, downstream of VUV chamber 40. In this position, fan 36 may somewhat reduce air pressure in chamber 40, which will reduce efficiency of ozone creation in chamber 40, and may create a slight negative pressure, with respect to atmospheric pressure, in chamber 40, chamber 48, and air passageway 57. Although a pressure regulator may be used instead of a simpler one-way valve 56, to keep pressure in chamber 48 and air passageway 57 closer to atmospheric, an embodiment as illustrated in FIG. 4A will likely result in a negative pressure, with respect to atmospheric pressure, within a mask, helmet, or other breathing air volume 32. Without an additional fan, for example in passageway 57, or passageway 54, to overcome the negative pressure created in chamber 40 in the configuration of FIG. 4A, a transient lower pressure created by inhalation, in conjunction with one-way valves 58, 35, may be required to pull de-ozonated, breathable air from chamber 40 through chamber 48 and passageway 57 into breathable air volume 32. This will likely require a close-fitting mask in order to avoid inward leakage of contaminated air during a wearer's inhalation cycle, and to extract breathable air from volumes 40 and 48. Although this situation is generally undesirable, there is an advantage, and such arrangement may be permissible for embodiments to be used with less dangerous contaminants. The advantage of a configuration as illustrated in FIG. 4A is that, for decontaminating a vehicle passenger compartment and some other enclosures, a fan may already be already present in the vehicle or associated with other enclosures and normally used to draw air into the vehicle passenger compartment or other enclosure for ventilation, heating, or cooling purposes. Such an existing fan in vehicles or other enclosures may also be used in place of a separate fan 36 to promote air flow through chambers 40 and 48. Such an embodiment and configuration may require use of special covers or other hardware, as illustrated and discussed later herein, to connect to and interface with a vehicle or other enclosure with little or no modification to the vehicle or other enclosure.

Another optional feature illustrated in FIG. 4 and in FIG. 4A involves possible use of a humidifier in conjunction with coarse filter 38. Adding humidity to air from source 37 before the air is introduced to chamber 40 provides two benefits. Having humidity in an air stream flowing through VUV exposure chamber 40 enhances production of some ozonites, particularly hydroxyl radicals, that are more reactive than ozone alone, and more effective in breaking down some contaminants. A second benefit is introduction and transfer of moisture into volume 32. Moisture, particularly humidity above about 94 percent relative humidity within a volume 32 to be decontaminated, promotes conversion of spores into actively growing forms of bacterial or fungal pathogens, which forms are generally more susceptible to damage and neutralization by ozone, ozonites, and ultraviolet light. In some embodiments, coarse filter 38 may include a media, such as a Seltzer pad, open cell foam, or other porous material kept moist, for example, by water from a reservoir. Alternatively, a pressure or ultrasonic atomizer, or other device for adding humidity to an air stream may be used, at least during early stages of operation. In applications and embodiments involving decontamination of protective suits, such as HAZMAT suits, moisture from perspiration of a wearer may contribute to humidity within a recirculated air stream which may help maintain suitable concentrations of moisture within exposure chamber 40 and within the suit to obtain the benefits of moisture noted above.

Having provided an overview of typical elements and their uses in various embodiments of the instant invention, Applicant now directs attention to other alternative embodiments, illustrated in a schematic fashion in FIG. 5A, FIG. 5B, FIG. 5C, and FIG. 5D, that may be used for different applications, and tradeoffs associated with use of, and placement of, various alternative and optional elements. In these figures, solid line arrows and dashed line arrows represent air flow paths and, generally, represent air flow passageways that may be implemented as tubes, pipes, hoses, or similar structures that contain and direct the flow of air.

FIG. 5A represents an embodiment that may be used in an application where only decontamination of a contaminated volume 70 is desired, without a need to also provide breathable air. Volume 70, for example, might be an unoccupied passenger compartment of a vehicle. In this example embodiment, outside air 60 that may itself contain airborne chemical or biological contaminants is drawn in by action of one or more fans 64, 68 through an optional filter or humidifier 62 that acts as a coarse filter to remove fibers and larger particulates from an intake air stream, and, in some embodiments, also adds humidity which, as noted earlier, may be used to contribute to formation of hydroxyl radicals or to promote activation of certain pathogens to render them more susceptible to destruction by ozone and ozonites. The intake air stream flows through an ozone generator 66 that may contain a corona discharge ozone generator in addition to, or instead of, an ozone generator that uses VUV radiation to create ozone. A corona discharge ozone generator may be used when a higher concentration of ozone is desired to promote destruction of certain chemical or biological contaminants, but, depending upon the characteristics of contaminants and of the volume 70 to be decontaminated, a tradeoff must be made regarding optional injection of humidity as noted above, since humidity in an air stream fed to a corona discharge ozone generator contributes to creation of nitrous oxides, which in turn may lead to creation of nitric acid when combined with additional moisture in a volume 70 being treated. However, where the volume under treatment is uninhabited, a relatively short-term exposure to nitric acid in the interior of a vehicle in combination with ozone may increase germicidal action. Ozonated air then flows, under influence of one or more fans 64, 68, from ozone generator 66 into contaminated volume 70 where ozone and ozonites in the air stream interact with and neutralize chemical and biological contaminants. For a generally closed loop implementation that may be desirable to promote higher concentrations of ozone and higher effectiveness against some contaminants, ozonated air from contaminated volume 70 may be recirculated back into ozone generator 66 where ozone concentrations are reinforced and contaminants carried in the air stream from volume 70 are subjected to stronger concentrations of ozone and, optionally, germicidal and other destructive irradiation by one or more ultraviolet lamps, within ozone generator 66. Optionally, if only a single pass open-loop implementation is desired, ozonated air may be intentionally released from volume 70 back into outside air 60 as indicated by dashed arrow 72. In many applications, where contaminated volume 70 is a vehicle passenger compartment or a protective suit, unintentional leakage of air from volume 70 into outside air 60 is likely, requiring introduction of additional outside air through optional filter/humidifier 62 and fan 64 as indicated at the beginning of this discussion. In addition, one of fans 64, 68 may be the vehicle fan, with a circulatory mode of the vehicle ventilation system set in a recirculation mode.

FIG. 5B illustrates an embodiment that may be used when only decontaminated breathing air 84 is desired, without a need for decontamination of a contaminated volume as in FIG. 5A. In an embodiment as shown in FIG. 5B, potentially contaminated outside air 66 is drawn through an optional coarse filter or humidifier 62 and flows into an ozone generator 66 under influence of an optional fan 64, or where a fan is omitted, under influence of a user's respiratory inhalation and exhalation pressures in conjunction with one-way valves 82, 86 which together act as an air pump. In ozone generator 66 contaminants in the intake air stream are subjected to destructive actions of high concentrations of ozone, ozonites, and monatomic oxygen, as well as exposure to VUV radiation, as described earlier herein. From ozone generator 66, ozonated air flows into an ozone destruction chamber 78 where UV-C radiation is used to reduce ozone concentrations to levels acceptable for breathing air, and also further subject any surviving contaminants to additional destructive actions of monatomic oxygen and UV-C radiation. From chamber 78, de-ozonated air may optionally be directed through a polishing filter 80, which may contain activated carbon, for removal of any residual contaminants before being directed through an optional one-way valve 82 into a breathing air chamber 84, which may be a face mask, helmet, or hood. From breathing air volume or chamber 84, air may be exhausted via optional one-way valve 86 into outside air 60, or may be recirculated to ozone generator 66 via an optional air flow restriction device 76, which may also be a carbon dioxide scrubber or rebreather, as noted earlier. One-way valves 82, 86 may not be needed in embodiments where optional fan 64 is used to maintain positive pressurization from fan 64 up through breathing air volume 84. However, one-way valve 86 will generally be desirable to insure no influx of contaminants during a user's inhalation portion of a respiratory cycle. Both one-way valve 82, 86 will generally be required in embodiments where a fan 64 or similar air movement device is not used. An integrated ultraviolet radiation exposure assembly, as disclosed later herein in FIGS. 18A, 18B, 18C, 19, and 20 and related descriptions, may be used to provide both ozone generation and ozone destruction capabilities in this and other embodiments shown herein.

FIG. 5C illustrates an embodiment that may be used when breathable air 84 is desired in addition to decontamination of a contaminated volume 70. In this embodiment, outside air 60 is drawn through optional filter or humidifier 62, as described earlier, and flows into ozone generator 66 under influence of one or more fans 64, 68. As noted earlier, ozone generator 66 may contain corona discharge elements in addition to, or instead of, one or more VUV lamps. Ozonated air flows from ozone generator 66 into contaminated volume 70 where decontamination reactions continue as noted earlier. In a preferred closed-loop flow for decontamination purposes, ozonated air from volume 70 flows through optional air flow restriction device 76 and is recirculated to ozone generator 66 where ozone concentrations are increased and additional decontamination reactions occur as noted earlier. An air flow restriction device 76 is normally desirable, as noted earlier, when contaminated volume 70 has flexible boundary walls, as in a protective suit, or when it is desired to maintain positive pressure within volume 70 and other elements to avoid uncontrolled inflow of contaminants. For some embodiments, it is desirable that air flow restrictor 76 be adjustable to provide control of pressurization within volume 70 and to balance unintentional leakage 74 and intake air flow from outside air 60 through optional filter or humidifier 62 and into ozone generator 66. As noted earlier for FIG. 5A, some embodiments may be implemented as a single pass for ozonated air, wherein ozonated air is not recirculated through ozone generator 66 but instead is exhausted from contaminated volume 70 back into outside air 60 as indicated by dashed arrow 72. Ozonated air to be de-ozonated and provided as breathing air may be allowed to flow from contaminated volume 70 through an ozone destruction chamber 78 where a UV-C lamp is used to reduce ozone concentrations to acceptable levels. De-ozonated air may then flow through optional polishing filter 80 and optional one-way valve 82 into breathing air volume 84. From breathing air volume 84, air may be exhausted back into outside air 60 through optional one-way valve 86 as indicated by solid arrow 90 if is it not desired to recirculate oxygen, humidity, or other resources in the breathing air, including air exhaled from a user. In cases where recirculation of breathing air is desired, air from breathing air volume 84 may be directed back into contaminated volume 70 where it is mixed with air flowing in a decontamination flow loop and thence recirculated through ozone generator 66 with other air flowing in a decontamination flow loop. Alternatively, breathing air may be recirculated directly into a path leading to ozone generator 66. Depending upon air flow losses, desired pressures, and other factors, an optional air flow restrictor 92, which may also be a carbon dioxide scrubber or rebreather, may be employed in either return path from breathing air volume 84 to either volume 70 or to ozone generator 66. As in embodiments described above in FIG. 5B, unintentional leakage from breathing air volume 88 to outside air 60 may also occur around face masks, hood, helmets, and the like, as indicated by dashed arrow 88, requiring introduction of additional make up air flow via optional filter or humidifier 62 and into ozone generator 66 as describer earlier.

FIG. 5D illustrates an alternate embodiment that may be used to provide breathing air 84 in addition to decontamination of contaminated volume 70. Elements and functions in this embodiment are essentially the same as described above for FIG. 5C, except that ozonated air to be de-ozonated and provided as breathing air is extracted from ozone generator 66 rather than from contaminated volume 70, as indicated by the solid arrow from ozone generator 66 to ozone destruction chamber 78. This embodiment provides a more direct path for purified air subjected to higher ozone concentrations and reduces likelihood that ozonated air being provided to ozone destruction chamber 78 may have become re-contaminated via mixing with contaminants in contaminated volume 70 before they have been neutralized. This embodiment may provide higher confidence in safety of breathing air for applications involving more dangerous contaminants.

Figure 6:
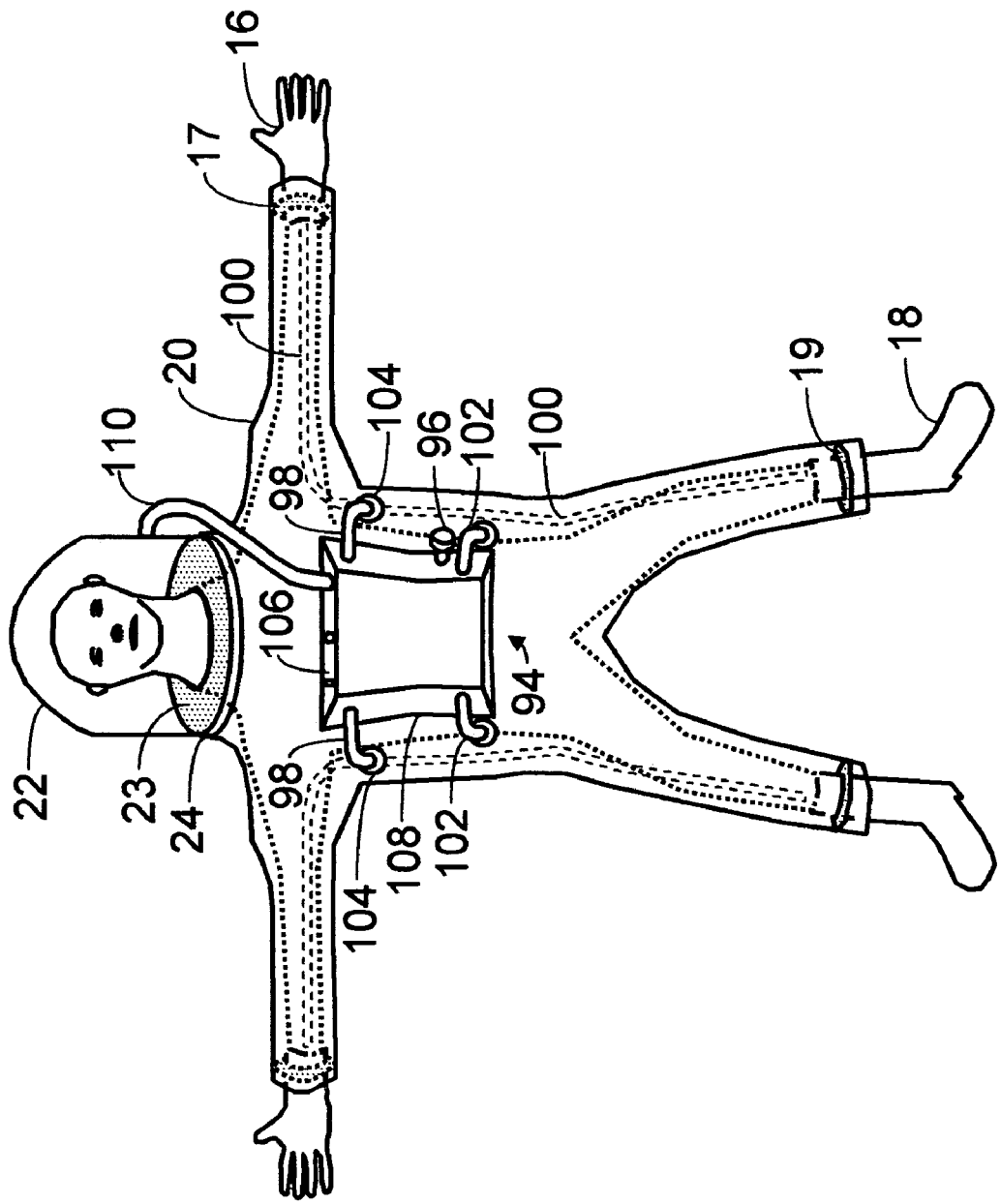
FIG. 6 is an illustration showing an overview of use of an embodiment of the instant invention with a protective suit.

An illustration of how an embodiment of the instant invention may be worn and used with a protective suit is provided in FIG. 6, and an overview of intended uses and functions follows. Although in some embodiments, such as illustrated in FIG. 5B, the instant invention may be used to simply decontaminate and purify air extracted from an ambient environment and provide breathable air to a user, key aspects of primary embodiments and applications of the instant invention provide for use of masks, face pieces, mouthpieces, neck dams, hoods, helmets, or other features to provide separation and a degree of isolation of a supply of de-ozonated breathable air provided to a wearer from ozonated air provided to or within a main body section of a protective suit while it is being worn. An ozone generation and treatment unit 94 is used to provide germicidal and air purification treatment of air drawn into unit 94 generally through at least a coarse filter (154, FIG. 7) from an ambient environment outside protective suit 25. In some embodiments and applications, an unit 94 of the instant invention may use air drawn or forced into unit 94 from a self contained breathing unit worn by a user or from some other source (e.g., air provided through a hose from a central air supply in a facility) to augment or replace use of air from an external ambient environment. Disinfected and ozonated air containing ozone and ozonites is then provided through one or more suitable fittings 104 to miniature air ducts or hoses 100 inside main body section 20 of protective suit 25 while it is being worn in order to provide germicidal, air purification, and decontamination capabilities of ozone and ozonites to the interior of body section 20 of suit 25, and to skin and clothing of a wearer. Since ozonated air injected into suit section 20 from unit 94 will generally have ozone concentrations higher than those deemed safe or comfortable for breathing air, features such as a separate breathing mask and hood (for protective suits similar to those illustrated in FIG. 1A and FIG. 1B) or a well-sealed neck dam (for protective suits employing a sealed helmet as illustrated in FIG. 2) are used so that air having a higher than permissible ozone concentration is not mixed directly with a wearer's breathing air. Ozonated air thus provided to suit section 20 is generally pumped through small flexible hoses or other miniature air ducts 100 to be released at extremities of a wearer's arms and legs but within the sealed volume of suit section 20 so as to thereby create a general flow of air within main body section 20 of protective suit 25 back to one or more exhaust ports 102 through which ozonated air is allowed to flow back into unit 94 for further treatment. The non-permeable nature of material from which protective suits are made, combined with use of sealing zippers, elastic cuffs, neck dams, or other methods of preventing or minimizing escape of air from protective suit 25, allow suit section 20 to be pressurized slightly above atmospheric pressure to promote flow of ozonated air within suit section 20 and, as noted earlier, to prevent intrusion of contaminants through small tears or other leaks.

In some situations and embodiments wherein a wearer is provided a separate, independent source of breathable air, further treatment within unit 94 may consist of additional generation of ozone and return of ozonated air with a higher concentration of ozone and ozonites to interior of suit section 20 in order to further boost concentration of ozone and ozonites inside suit section 20 and enhance germicidal and decontamination reactions within the interior of suit section 20. In other embodiments wherein treated air is to be provided to a wearer for breathing, at least a portion of ozonated air returned to unit 94 from suit section 20 is allowed to flow through a chamber wherein ozonated air is exposed to ultraviolet radiation having significant intensity at wavelengths near 254 nm (generally referred to as UV-C radiation in the literature and elsewhere herein), and minimal or no intensity at wavelengths near 185 nm (generally referred to as vacuum ultraviolet, or VUV radiation). Exposure of ozonated air to UV-C radiation will decompose ozone, provide further oxidation of contaminants and sterilization of biological agents, and reduce ozone concentrations to levels safe for breathing by a wearer. Eliminating or minimizing exposure, at this point in treatment, of previously ozonated air to radiation having any significant intensity at wavelengths near 185 nm prevents generation of additional ozone in an air stream which will be provided as breathable air to a wearer. In an embodiment of FIG. 6, after ozonated air from suit section 20 has been exposed to a suitable intensity of UV-C radiation in unit 94, concentrations of contaminants and ozone are sufficiently reduced so that the de-ozonated air is generally safe for breathing by a wearer, although for some applications and contaminant environments, it may be desirable to route the de-ozonated air through a polishing filter to eliminate any trace contaminants and by-products resulting from destruction of contaminants by ozone, ozonites, and ultraviolet light. De-ozonated air thus treated is provided as breathing air to a wearer though a hose 110 or other air conveyance to a mask, mouthpiece, face piece, helmet 22, hood, or other apparatus worn by a user for protection and for provision of breathing air. In some embodiments, air in which ozone has been largely depleted by exposure to UV-C radiation may be passed through an activated carbon filter used as a "polishing" filter for removal of residual contaminants and residual ozone. In some embodiments and operational modes and conditions, air expired by a user may be released to an external environment, generally through a one-way valve, or in other embodiments or operating modes and conditions, exhaled air may be returned to unit 94 for recirculation or for recovery of moisture, which can be used to enhance generation of hydroxyl radicals for use in decontamination, or other components of exhaled air. In the latter case, as noted earlier, it may be necessary to direct exhaled air through a carbon dioxide scrubber or rebreather so as to prevent accumulation of unacceptable levels of carbon dioxide.

The technique of circulating ozonated air through protective suit section 20 for use in decontaminating the interior of a suit and a wearer's skin and clothing, and extracting a portion of an ozonated air stream to be de-ozonated and provided as breathing air, may be implemented in either of at least two basic modes, or in some combination of these modes. Two basic modes which may be used include a cyclic flow mode and a continuous flow mode. Alternative embodiments that implement a cyclic flow mode and a continuous flow mode are illustrated in FIG. 7 and FIG. 8, respectively.

Figure 7:
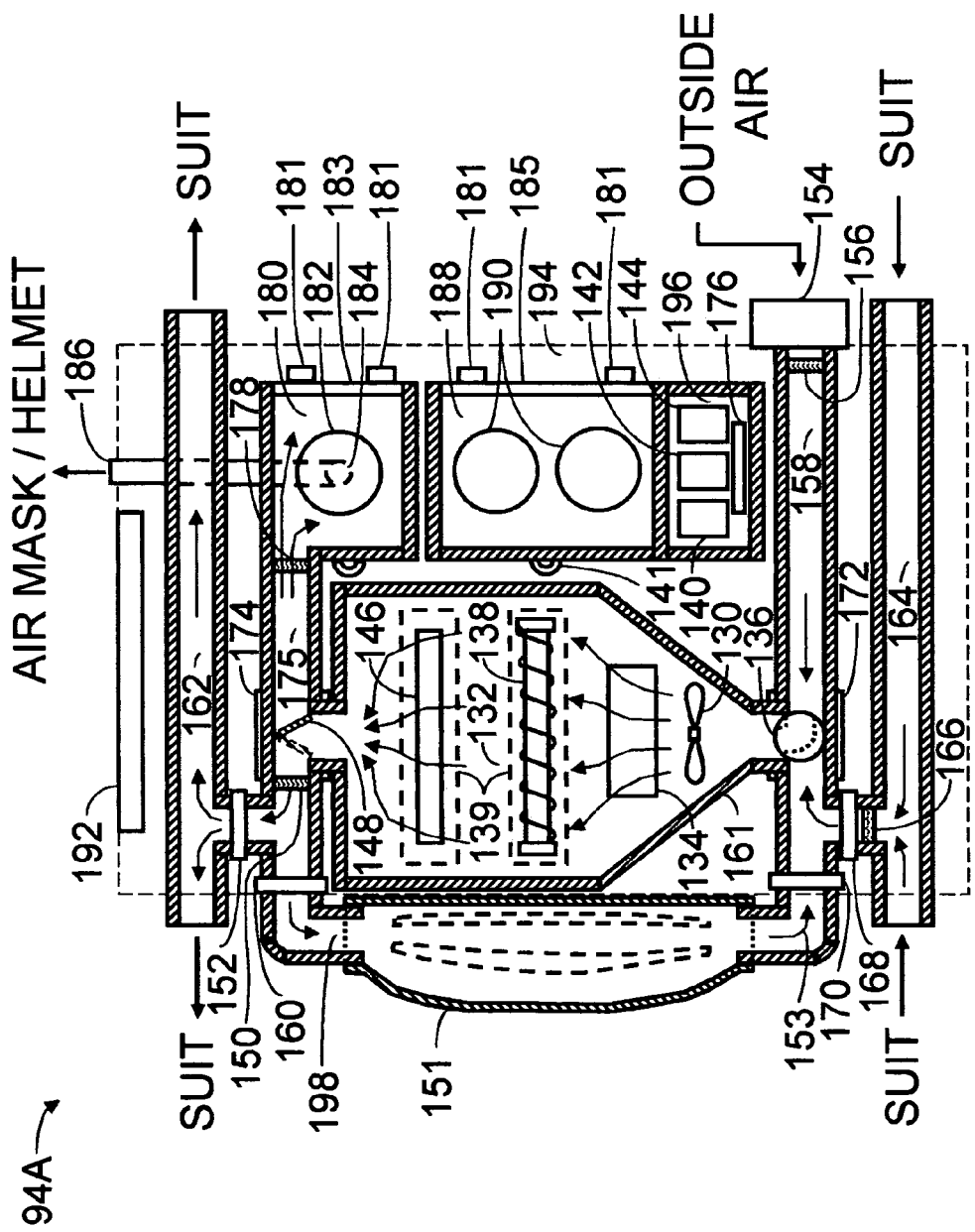
FIG. 7 is a representative interior diagrammatic view of an embodiment of an ozone generation and treatment unit of the instant invention that may be used as illustrated in FIG. 6.
Figure 8:
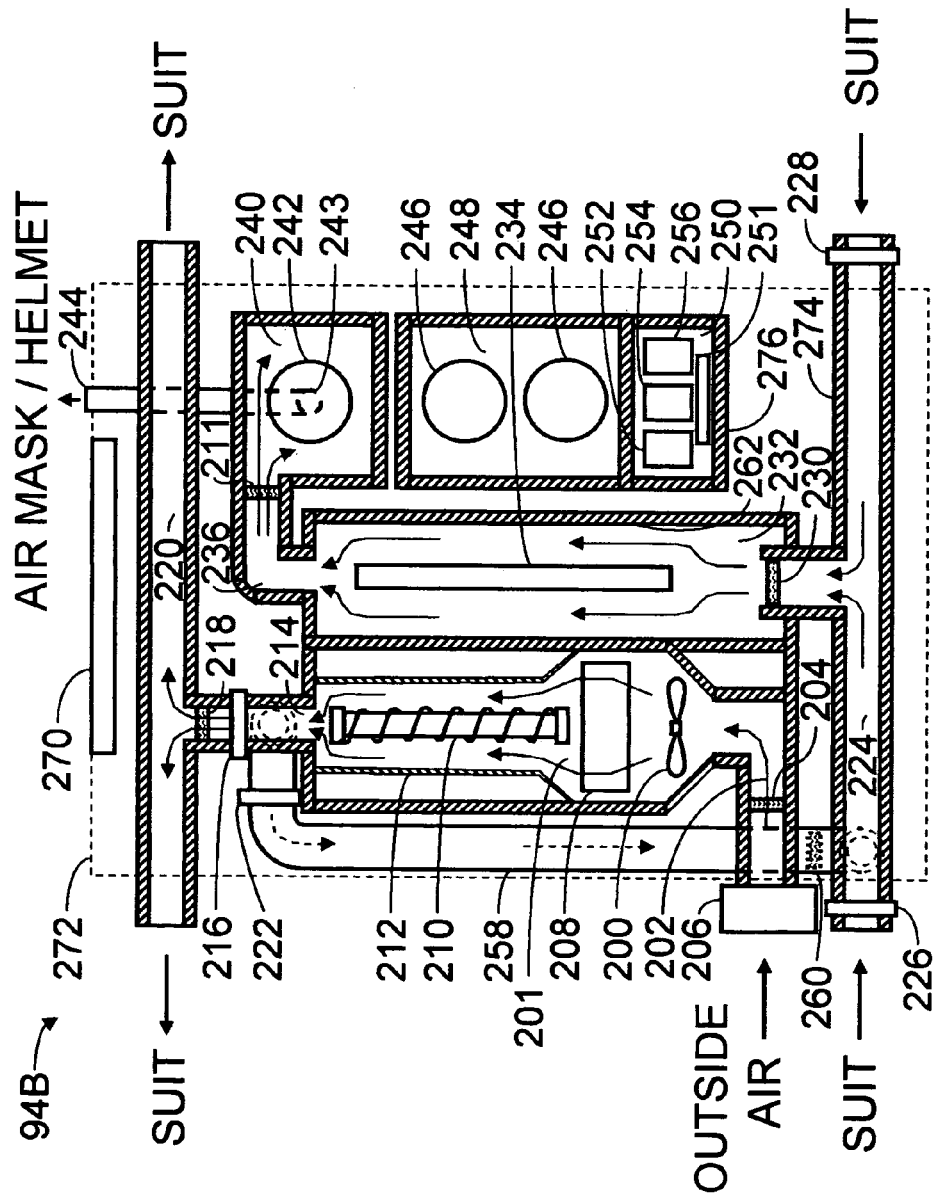
FIG. 8 is a representative interior diagrammatic view of an alternate embodiment of an ozone generation and treatment unit of the instant invention that may be used as illustrated in FIG. 6.

In a cyclic flow mode, using an embodiment such as illustrated in FIG. 7, which represents one alternative implementation (unit 94A) of an unit 94 as shown in FIG. 6, a cycle consists of an ozonation portion of a cycle and a de-ozonation portion of a cycle. During an ozonation portion of a cycle air is ozonated and provided to a volume to be decontaminated, such as an interior of a protective suit or a passenger compartment in a vehicle. During a de-ozonation portion of a cycle, ozonated air is withdrawn from the volume being decontaminated, or from another portion of a path of ozonated air, and de-ozonated and provided as breathing air to a wearer, occupant, or other user. Referring to FIG. 7, in an ozonation portion of a cycle, a fan 130 and valves 136, 148 controlled by valve controllers 172, 174, respectively, permit outside air to be drawn into an unit 94 through an optional coarse filter or humidifier 154 and air passageway 158, ozonated in chamber 132 using either or both of a corona discharge device 134 powered by high voltage transformer 140, or a VUV lamp 138, conventionally supported in chamber 132 and which may be partially surrounded by reflectors 139 and powered by ballast 142, and pumped through air passageway 162 into a protective suit, using appropriate fittings and interfaces (e.g., 104, FIG. 6; 300, FIG. 9A; 311, FIG. 9D), which preferably interface with miniature air passageways (100, FIG. 6) to route ozonated air to extremities of suit (20, FIG. 6). This portion of a cycle may continue for a generally brief period of time, perhaps only a few seconds, while air flow paths from protective suit section 20 back to chamber 132 of unit 94A are blocked off by valve 136. The duration of this portion of a cycle is governed, in part, by the volume of air that can be contained in an expanded suit or other contaminated volume that may be treated in this manner. Then, in a separate, de-ozonation, portion of a cycle, corona discharge device 134 and VUV lamp 138 are de-energized, UV-C lamp 146, conventionally supported in chamber 132 and which may be partially surrounded by reflector 139 and powered by ballast 144, is energized, and positions of valves 136 and 148 are changed to allow air to flow from suit 20, or other volume being decontaminated by ozonated air, through chamber 132 for de-ozonation, and ultimately provided as breathing air to a suit occupant, as explained in more detail below. In this de-ozonation portion of a cycle, valve 136 blocks air from an external environment and permits air to be drawn from protective suit (20, FIG. 6) through appropriate fittings (102, FIG. 6; 340, FIG. 11) and air passageway 164 and pumped back through chamber 132 over and around UV-C lamp 146 so that UV-C radiation depletes ozone in the air, which is then directed by repositioned valve 148 into air passageway 175 into chamber 180 and on through polishing filter 182 and a threadable or quick disconnect fitting 184 into another air passageway 186 which carries the now breathable air to an air mask or helmet where it may be used as breathing air by a suit occupant. Polishing filter may be an activated carbon filter, such as a 40 mm NATO thread M-95 filter cartridge available from approvedgasmask.com, or other types of filter tailored for particular contaminants or byproducts. Optional air flow restrictors or pressure regulators 156, 166, 160, 178 may be used in some embodiments to help maintain appropriate pressures in different segments of air flow paths and passageways. In this de-ozonation portion of a cycle, air from which ozone has been eliminated is then provided to a wearer, occupant, or other user for breathing air. After completion of a de-ozonation, or breathing, portion of a cycle, unit 94A then reverts back to a ozonation mode wherein UV-C lamp 146 is de-energized, VUV lamp 138 and optional corona discharge unit 134 are re-energized, positions of valves 136, 148 are changed, and unit 94A again draws in external air, ozonates the air with an optional combination of corona discharge and VUV unit, and pumps it into the protective suit. Spare polishing filter canisters 190 may be stored in a compartment 188 of unit 94. To allow for quick replacement of a depleted filter canister 182 by a spare canister 190, chamber 180 and compartment 188 may be are sealed for quick access by doors 182, 183, respectively, hinges 181, and latches 141 designed to allow quick access and operation by a wearer of a suit without removal of protective gloves 16. Optional valves 152, 160, 168, and 170, and air passageways 198, 153 provide a capability to block off air flow to and from a protective suit or other contaminated volume and direct air into an optional expandable chamber 151 which may be used to support a cyclic mode of operation and provide breathing air to a wearer during startup mode before a protective suit or sealed or adequately decontaminated, or in event of damage to a protective suit that precludes normal cyclic mode of operation. When used during a startup mode, for example, valves 152 and 168 may be partially opened during an ozonation cycle to allow flow of ozonated air into a suit and into expandable chamber 151, but valve 168 is kept closed during both ozonation and de-ozonation cycles until sufficient ozone concentrations have developed in a suit or other container, and suitable time has elapsed, to provide confidence that contaminant levels inside a suit or other contaminated volume have been reduced to levels safe for breathing. It may be necessary to provide an escape valve in fittings 102 to allow air to escape from a suit or other enclosure while valve 168 is closed during startup operations if normal leakage from a suit is not sufficient to permit continued introduction of ozonated air during ozonation cycles. Duration of an ozonation portion of a cycle may be adjusted relative to a deozonation portion of a cycle in order to maintain adequate suit inflation for wearer comfort and efficiency of air flow within a suit, and in order to make up for air losses due to leakage from a suit or other enclosure being decontaminated. In addition, valve 148 may be operated in a partially open or proportional position to allow division of air between passageways 175 and 162 during a de-ozonation portion of a cycle to allow some recirculation of air within a suit 20 if desired for some applications.

One or more circuit boards 176 used to implement controls and provide power to fan 130, high voltage transformer 140 and ballasts 142, 144, valve controllers 172, 174, user control panel 192, and sensors or other components of various embodiments may be located in compartment 196. Although not specifically illustrated, valves 152, 160, 168, 170 may be operated electrically under control of logic implemented in circuit board 176, or they may be operated manually under control of an operator. Power for operation of unit 94A may be provided via an external battery pack (e.g., worn on a user's belt) separately or in combination with other power sources (e.g., solar cell panels integrated in portions of a suit structure). Walls (e.g., 178) of air passageways should be made of a lightweight material tolerant of exposure to ozone and contaminants likely to be encountered. Walls of chamber 132 should be made of a material that is also tolerant of exposure to ultraviolet light. Other portions of structure of unit 94A should be made of generally lightweight materials capable of providing necessary structural strength and durability, and mounted on a backboard 194 or other support member with appropriate shape and padding for wearer comfort as will be evident to one skilled in applicable arts.

A cyclic mode of operation may tend to cause a protective suit to alternately inflate and partially deflate, which may be acceptable for many operational conditions, but may present problems in other operational conditions. For example, a protective suit may be uncomfortably drawn down against a wearer's body, which may also preclude adequate air flow within a suit, or additional contaminants may be drawn into a rigid or semi-rigid, but leaky, enclosure, such as a passenger compartment in a vehicle, during a de-ozonation portion of a cycle.

Another embodiment and mode of unit 94 operation that may avoid some problems associated with a cyclic mode of operation is a continuous flow mode. In a continuous flow mode, implemented in an alternate embodiment (94B) as illustrated in FIG. 8, external air is drawn through coarse filter or optional humidifier 206 by fan 200 into ozonation chamber 201 where it is ozonated by either, or a combination of, corona discharge unit 208 powered by high voltage transformer 252 or VUV lamp 210 conventionally support in chamber 201 and powered by ballast 254. Air thus ozonated flows into a protective suit 20 through air passageway 220 and appropriate ports (104, FIG. 6), fittings (300, FIG. 9A; 311, FIG. 9D), and miniature air ducts (100, FIG. 6; 330, FIG. 10B) as described elsewhere herein while one or more exhaust ports (102, FIG. 6) and fittings (340, FIG. 11) simultaneously allow ozonated air to be exhausted from suit 20 through air passageway 224 back into a separate chamber 232 within unit 94B wherein ozonated air is depleted of ozone by exposure to radiation from UV-C lamp 234 conventionally supported in chamber 232 and powered by ballast 256 and continues to flow as deozonated air through passageway 236 into filter chamber 240. Interior walls 262 of chamber 232 may be made of, or have attached a layer or coating of, material reflective for UV-C radiation to enhance efficiency of de-ozonation. Deozonated air then flows through optional polishing filter 242 through a threaded or quick disconnect filter connection 243 into a tube 244 that provides passage for deozonated and optionally filtered air on to an air mask, hood, helmet, or other apparatus used to provide protected breathing air to a wearer. Air flow restriction device 230, optional for some embodiments, is used to maintain an appropriate degree of positive pressure within a suit or other enclosure, to maintain appropriate inflation, where applicable, and outflow through leaks to prevent inflow of contaminants. Other optional air flow restriction devices 204, 218, 211 may be used to adjust pressures within different chambers and segments of air flow passageways as desired to achieve effects described earlier in conjunction with FIG. 4 and FIG. 4A. As noted earlier in the description of an embodiment shown in FIG. 7, spare filters 246 may also be located in a compartment 248 and may be made readily accessible for changing using compartment doors as described for FIG. 7. Transformer 252, ballasts 254, 256, and one or more electrical and electronic circuit boards 251 used to distribute power, control operation of components, and implement user control selections, made via user control panel 270, may be located in compartment 250. Power for operation of unit 94B may be provided via an external battery pack (e.g., worn on a user's belt) separately or in combination with other power source (e.g., solar cell panels integrated in portions of a suit structure). Selection of materials for unit 94B may follow the guideline provided earlier for unit 94A and elsewhere herein. To support a startup period, and to provide emergency breathing air in event of damage to protective suit 20 or other enclosure causing major loss of ozonated air, a suit bypass mode of operation is provided by air passageway 258 in conjunction with valves 216, 222, 226, and 228. A bypass mode is implemented by closing valves 216, 226, and 228, and opening valve 222 (which is closed during normal operations) so that air exiting chamber 201 into air passageway 214 is blocked from entering passageway 220 and instead routed through passageway 258 into passageway 224 where it continues to flow into deozonation chamber 232 and continues through other passageways and components as described earlier into a wearer's mask, helmet, hood, or other apparatus for providing breathing air to a user. During a startup period, valves 226 and 228 may be closed, and valves 216 and 222 may be partially opened to control and apportion flow of ozonated air into suit 20 as well as through bypass 258 to allow a period for ozonated air to decontaminate the interior of suit 20, or wearer's clothing or skin, before air from suit 20 is allowed to flow back through unit 94B for deozonation to be provided as breathing air to a user.

In some embodiments, a translucent cover containing phosphors for production of visible or near-infrared light may be provided over VUV or UV-C exposure chambers, rather than an opaque cover, to permit generation of visible light from ultraviolet light present within VUV and UV-C chambers.

Fittings and devices that may be useful in attaching an unit 94 of the instant invention to new or existing protective suits, and routing ozonated air within a suit, are illustrated in FIG. 9A, FIG. 9B, FIG. 9C, FIG. 9D, FIG. 10A, FIG. 10B, and FIG. 11. FIG. 9A is a top-down view of a fitting 300 that may be used to connect an air hose to a protective suit. FIG. 9B is a side-on view of fitting 300 showing a center tube 302 of fitting 300 inserted through a hole in suit fabric 310 where it may be sealably seated in or otherwise connected with another fitting (331, FIG. 9C) so that together fittings 300 and 311 comprise a bulkhead connector and provide a sealed passageway for air through fabric 310. FIG. 9D it is a top-down view of fitting 311 and FIG. 9C is a side-on view of fitting 311. Fittings 300 and 311 may be drawn together using screws and other fasteners through holes (306, FIG. 9A; 314, FIG. 9D) in their flange sections (301, FIG. 9A, FIG. 9B; 312, FIG. 9C, FIG. 9D) to provide sealing pressure against gasket 318, FIGS. 9C and O-ring 320, FIG. 9C. Alternatively, tube section 302 may contain male threads or other features designed to interface with female threads or other features in fitting 311 to provide for easier or faster connection of fittings 300 and 311. A raised shoulder 308, FIG. 9A or similar structure may be provided on fitting 300 to support retention of a hose or tubing on tube 302, or a quick disconnect device, may be used to support attachment of an air hose from an unit (94, FIG. 6) to fitting 300. Fitting 311 comprises a "T" fitting providing connection tubes 316 (FIG. 9D) for miniature air ducts and a transition for air flowing in through hole 304 (FIG. 9A) in tube 302 (FIG. 9B) into a mating hole in fitting 311. Shoulders or other features, including quick disconnects, may be used on connection tubes 316 to support attachment and retention of tubing or other type of miniature air ducts (100, FIG. 6; 330, FIG. 10B). Tubes 316 may have an elliptical or other generally flat shape to minimize intrusion into a body section 20 of a protective suit.

Referring to FIG. 10A and FIG. 10B, miniature air ducts (100, FIG. 6; 330, FIG. 10B) may be inserted within protective suit 20 to provide for transport to extremities of arms and legs of ozonated air that flows into suit 20 via fittings 300 and 311. Miniature air ducts 100 may be made of layers 332, 334 (FIG. 10A) or loops of semi-permeable or relatively impermeable fabric or other material, which layers may be attached together using stitching 338, FIG. 10B, glue, ultrasonic welding, or other joining techniques suitable to whatever material is used, with holes 337, FIG. 9B punched or otherwise added where exit of ozonated air is desired to promote a flow pattern within protective suit 20 that helps insure all areas are exposed to ozonated air to promote thorough decontamination. Alternatively, tubing made of a material compatible with ozone, and which preferably has a more or less flat cross-section, may be used as miniature air ducting. A layer of contact cement, adhesive such a found on carpet tape, or thermosetting adhesive such as found on iron-on repair tape may be stitched or adhesively attached to a side of a miniature air duct to allow a miniature air duct to be easily routed and affixed within a protective suit. Care must be taken to insure any such adhesive or thermal technique used to attach miniature air ducts within suits is compatible with and does not cause damage to suit material or the air ducts.

FIG. 11 illustrates one embodiment of a exhaust fitting 340 that may be used in conjunction with pipe, tubing, or hose 102 and a fitting similar to fitting 300 to provide a passageway for air to be exhausted from the interior of a protective suit 20 and back into unit 94, or simply to the exterior of a suit, without having a wearer's clothing, skin, or other material block a passageway entrance 343. Fitting 340 may be designed with a receptacle and other features similar to that of fitting 311, FIGS. 9C, 9D, to sealably mate through a hole in the fabric of a suit with a fitting similar to fitting 300, FIGS. 9A, 9B. Fitting 340 may be joined to its mating fitting via fasteners through holes 342 or via other techniques described above for fittings 300 and 311. Stiff wires 344, plastic legs, or a similar structure may be affixed to flange 341 and used to keep a wearer's clothing, skin, or other material pushed away from passageway entrance 343 so that air from within suit 20 may flow into a passageway to external air or back to unit 94.

FIG. 6 and the preceding discussions use as an example a suit such as illustrated in FIG. 2 to teach how an embodiment of the instant invention may be used for decontamination of an interior of a suit or other protective enclosure and also for providing breathing air. Some minor tailoring is needed for use of embodiments of the instant invention with suits of other types, such as illustrated in FIGS. 1A and 1B, or with other enclosures. When practiced with fully enclosing suits such as illustrated in FIG. 1A, a decision must be made whether to mount an ozone generation and treatment unit 94 within a protective enclosure of a suit 1, FIG. 1A, or external to a protective enclosure of the suit, as illustrated in FIG. 6. For use within the protective envelop of a suit, the shape and form of a unit 94 may be modified from that shown in FIG. 6 to a thinner form or shape that may be worn, for example, on a wearer's chest, waist, or back within the protective envelop of the suit. As noted earlier herein, for different applications and contaminating agents, unit 94 may be used in place of, or in addition to, a self-contained breathing apparatus. An embodiment of unit 94 may be shaped to fit within a pouch 7, FIG. 1A, together with or in place of a conventional self contained breathing apparatus, such as a Scott Air Pak™, which is normally enclosed within pouch 7. Alternative, a suit 1 may be modified or originally manufactured to include a separate pouch for enclosing an embodiment of unit 94. If an embodiment of unit 94 is mounted internal to a protective envelope of a suit, an opening through the envelop material of the suit may be needed to provide air to an enclosed embodiment of unit 94 for ozonation and to make up air lost through leaks or through exhalation. Such openings could be made using fittings similar to those described above, but with an air hose routed within a suit from the opening to a unit 94, or a fitting providing an opening could be attached directly to a unit 94 inside a suit. For such an embodiment, it would be desirable to provide a non-obtrusive, form fitting coarse filter at an external interface to prevent airborne fibers, insects, or larger particulates from being drawn into a unit 94. For this configuration, a breathing air hose could be routed within an enclosure of a suit from a unit 94 to a breathing air mask or similar apparatus for providing isolated and protected breathing air to a wearer. Similarly, ozonated air for decontamination may be provided via hose or via direct connection of a unit 94 to miniature air ducts such as described earlier herein.

Alternatively, an embodiment of unit 94 may be worn external to a protective envelop of a suit similar to a configuration illustrated in FIG. 6. In such a case, an additional penetration of suit fabric may be needed to route breathing air from a unit 94 to a breathing air mask or similar device worn by a wearer within a protective enclosure of a suit. In such a case, penetration of suit fabric for routing breathing air to a face mask or similar device may be made using bulkhead connector-type fittings similar to those described earlier in FIGS. 9A, 9B, 9C, and 9D.

For purposes of decontaminating skin or clothing of individuals exposed to contaminants, while also providing breathing air, for example before a contaminated person is admitted to a decontaminated or clean area of a hospital or other emergency care or residence facility, a contaminated individual may be placed in a fully enclosing suit similar to that of FIG. 1A, or, in an emergency, even in a body bag or other large plastic bag, but provided with a breathing mask or a hood, preferably constructed of clear plastic but which may also be constructed of another plastic bag, secured, for example, around an individual's neck. Depending upon the exposure risk of any contamination, particularly in an area where an individual is being decontaminated, an individual's head could be allowed to protrude from a bag enclosing their body, with a bag enclosing their body and clothing secured around the individual's neck with a drawstring, tape, or other measure that provides a nearly airtight seal. A hood made preferably of clear plastic or similar material could be place over their head, and breathing air could be provided via hose from an ozone generation and treatment unit placed nearby. Fittings similar to those described herein, but tailored with features that could support rapid attachment, especially in an emergency, to a suit, body bag, or other enclosure to be used to connect hoses from an ozone generation and treatment unit to such suit, bag, or other enclosure containing a contaminated individual for providing ozonated air for decontamination, and for extracting air for recirculation, decontamination, and increased ozonation in an ozone generation and treatment unit of the instant invention.

When an embodiment of a unit 94 is used with a suit similar to that illustrated in FIG. 1B, the implementation is similar to that described in conjunction with FIG. 6, except that breathing air is routed to a breathing air mask or facepiece rather than to a helmet. Additionally, a peripheral seal of a face mask 15 onto a hood 14 of a suit 12 should be made tight enough to prevent leakage and mixing of ozonated air from within a suit 12 and hood 14 into breathing air being provided through face mask 15.

Figure 12:
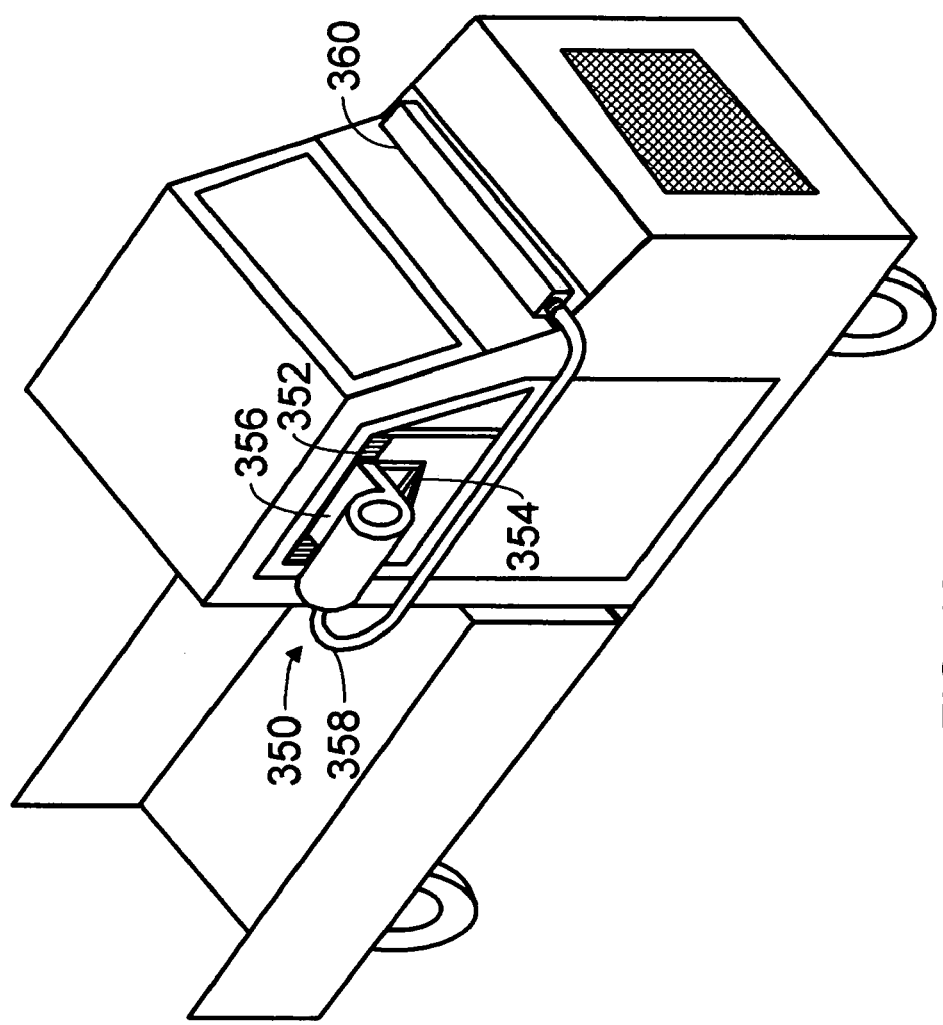
FIG. 12 is an illustration showing how components of an embodiment of the instant invention may be installed on a vehicle.

FIG. 12 illustrates one manner in which an embodiment of the instant invention may be attached to, and used to decontaminate, a passenger compartment of a vehicle 26. In this application, an embodiment of an ozone generation and treatment unit 350 constructed and functioning similar to that (unit 94) described earlier may be packaged into a configuration having an extension 356 of its structure designed to be inserted through a partially opened window (28, FIG. 3) of a passenger compartment, with a window edge against a bottom of the extension to clamp or seal the extension against the top window edge and upper inner edge of the window frame. Pullout panels 352, similar to those used with some home window air conditioners and ventilation fans, may be provided in some embodiments to aid in providing a weather and air flow seal in any space between structural extension 356 and frames of a vehicle window. Where necessary, a unit 350 may be supported via additional support structure 354. A hose 358 may be used to convey ozonated air from unit 350 to a vent hood 360 designed to sealably fit over an intake air vent (27, FIG. 3) of a vehicle (26, FIG. 3). Extension 356 includes an air passageway for removing air from the vehicle passenger compartment and routing the air through a chamber where it is ozonated, similar to the manner in which air is routed from a protective suit, as described earlier. Extension 356 also includes an air passageway which conveys de-ozonated air for breathing from unit 350 to one or more air hose connections on an end of extension 356 that extends into a passenger compartment of vehicle 26. User controls may also be provided on an end of extension 356. A cord with an electrical plug designed to plug into a cigarette lighter socket, or other type of power outlet available in a particular vehicle, or to an external power source where the vehicle is decontaminated while stationary, may also be extended from an interior end of extension 356 and used to provide power to unit 350. In one embodiment, occupants of vehicle 26 may wear air masks that cover their nose, mouth, and eyes, these masks connected via air hoses to connections on extension 356 that provide de-ozonated breathing air to occupants. In a similar manner as described above for embodiments of FIG. 7 and FIG. 8, air is drawn from either or both of external air and air contained within the passenger compartment of vehicle 26 into unit 350 where the air is ozonated. All or a portion of thus ozonated air is conveyed via hose 358 through vent hood 360 to be drawn or forced into the passenger compartment to provide decontamination benefits to the vehicle passenger air intake passageways as well as to the interior of the passenger compartment and to the clothing and skin of occupants. Air movement may be provided by a fan or blower that is already part of a vehicle's air conditioning or heating system, or by a fan contained within unit 350, or by a combination thereof, subject to considerations discussed in conjunction with FIG. 4 and FIG. 4A. Features and controls similar to those discussed earlier may be used to balance and control pressures and flow of ozonated air for decontamination within the vehicle and pressure and flow of air provided as breathing air to occupants. With appropriate design of vent hood 360, support of air hose or other passageway 358, and unit 350 for compatibility with particular vehicles, decontamination and protection may be provided by embodiments of the instant invention while a vehicle is parked or while it is being driven.

FIG. 13A and FIG. 13B together illustrate additional techniques by which a single VUV lamp may be used to provide both ozonation and de-ozonation functions. FIG. 13A and FIG. 13B also provide further detail on features that may be incorporated into various embodiments of the instant invention to also provide light in visible or near-IR portions of the electromagnetic spectrum for use in illuminating a user's path, work area, or similar application. In FIG. 13A, a reversible fan 370, which may have a reversible direction of rotation, or an ability to reverse the pitch of its blades, so as to change the direction in which air is propelled by the fan, is operated in a direction that pulls air through chambers 71 and 75 past VUV lamp 372 and past one-way door 376, which opens on spring-loaded hinge 377. Air flowing through chamber 375 is exposed to both VUV and UV-C radiation from VUV lamp 372. Air flowing through chamber 371 is exposed only to UV-C radiation which is transmitted through wall 374, which may be silicate glass or another UV-C transmissive but VUV blocking material such as FEP, TFE, or doped quartz, as disclosed earlier herein, that forms a boundary between chamber 375 and chamber 371. VUV radiation from VUV lamp 372 is strongly attenuated in wall 374. Since VUV radiation is more strongly absorbed than UV-C radiation by air flowing through chamber 375, more ozone is created than is destroyed in air flowing through chamber 375. If air flowing through chamber 371 contains ozone, UV-C radiation transmitted into chamber 371 through wall 374 will interact with and break bonds between oxygen atoms in ozone molecules, causing ozone molecules to break apart, typically into a diatomic oxygen molecule and a single oxygen atom. Single oxygen atoms are highly reactive and will rapidly interact with other chemical molecules in the air stream that can be oxidized, including molecules in biological pathogens, or will combine with another oxygen atom to generally form diatomic oxygen molecules. (Similar reactions also occur in chamber 375, but these reactions are dominated by breakdown of oxygen atoms by VUV radiation in chamber 375.) UV-C radiation in both chambers, as well as VUV radiation in chamber 375, also provide germicidal benefit against pathogens in air flowing through the respective chambers. In FIG. 13A, air flowing past fan 370 may be directed into a suit or other volume to be decontaminated, but ozone concentrations in mixed air flowing out of both chambers is diluted with respect to ozone concentrations in air flowing directly out of chamber 375 past open door 376. To obtain de-ozonated air for breathing or for other purposes, and referring to FIG. 13B, fan 370 may be reversed by either reversing its direction of rotation or the pitch of its blades, causing air to flow through chamber 371 in an opposite direction from that in FIG. 13A. In this mode, one-way door covering an end of chamber 375 is closed by air flowing in a reverse direction, so that no air flows through chamber 375. Air moved by fan 370 flows only though chamber 371, where it is exposed to UV-C, but not VUV, radiation, leading to destruction of ozone that may have been added in air when it was flowing in the direction indicated in FIG. 13A. The de-ozonated air may then be used for breathing air.

Features that may be added in some embodiments to provide visible or near-IR light are also illustrated in FIG. 13A and FIG. 13B. In a typical embodiment capable of emitting visible light, glass or another material transparent to visible light is used for an outer wall 385 of chamber 371. A layer of phosphors 386, such as commonly found in fluorescent lamps, that have an ability to absorb ultraviolet radiation and emit other, longer wavelengths of generally visible light, may be added to a surface, preferably an inner surface from a viewpoint of lamp 372, of chamber wall 385. Phosphors may be selected to be stimulated by UV-C radiation and emit fluorescently in visible or near-IR portions of the spectrum. Some phosphors may be toxic or otherwise harmful, and may also be soft and subject to flaking off in an air stream, so it will generally be desirable to add another thin layer 387 of glass or a coating on an inner surface (as viewed from lamp 372) of layer 386 of phosphors to prevent contamination by phosphor material of air flowing through chamber 371, and to prevent loss of phosphors. Glass or coating 387 may be selected to transmit UV-C radiation and be tolerant of exposure to UV-C radiation without damage. To provide efficiency and vision safety for ultraviolet radiation, layer 386 of phosphor material should generally be sufficiently thick to interact with and intercept virtually all UV-C radiation and any VUV radiation impinging on phosphor layer 386 from chamber 371. If desired, for example to support clandestine activities of special forces or police special weapons and tactics teams, phosphors may optionally be selected to absorb UV-C radiation and emit more energy in near-infrared wavelengths detectable by night vision or near-infrared imaging equipment used by such special forces and such teams to allow individuals thereof to see in the dark. Near-infrared radiation is also scattered less by particles in smoke and droplets in fog and may also thus provide better visibility, in conjunction with appropriate night vision or other imaging equipment, in smoke and fog than would be provided by visible light. A filter 381 that attenuates visible light but transmits near-infrared light may optionally be added to filter out visible light that might otherwise reveal presence of a wearer to the naked eye of an adversarial observer, or that might be scattered from smoke and fog and interfere with visibility in the near-infrared. Such a filter may be made, for example, of a material similar to that used in photographic filters that block visible light but transmit near-infrared radiation. Likewise, light produced by phosphors may be focussed generally in front of an individual by a lens, such as a Fresnel lens. In an alternate embodiment, a layer of phosphors may be added to an outside surface of a glass wall 385 and then covered with a layer of plastic or other coating transparent to visible light that also provides abrasion protection for phosphors and breakage protection for glass 385.

Figure 14C:
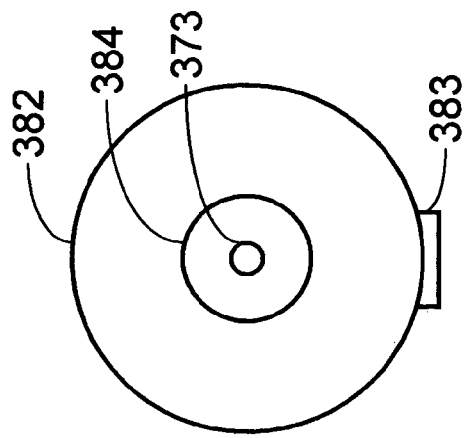
FIGS. 14A and 14B are diagrammatic views showing how ozone production capability could be further enhanced over that of apparatus show in FIGS. 13A and 13B while preserving ozone destruction capability.
Figure 14A:
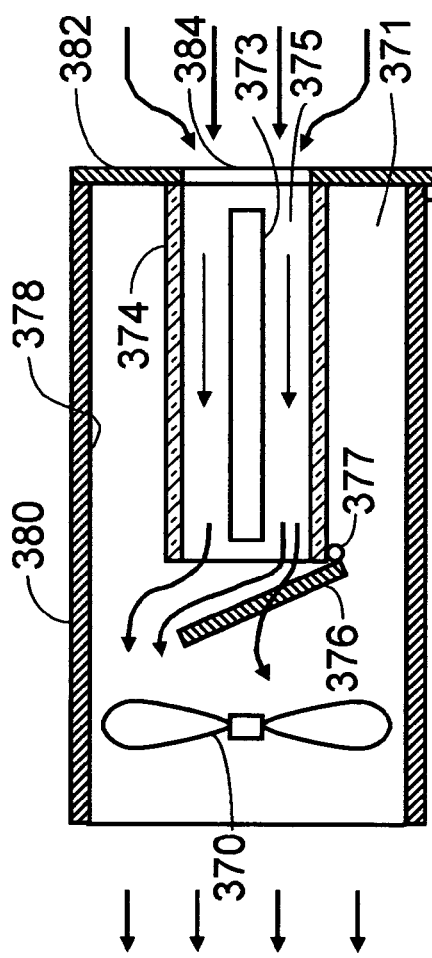
Figure 14B:
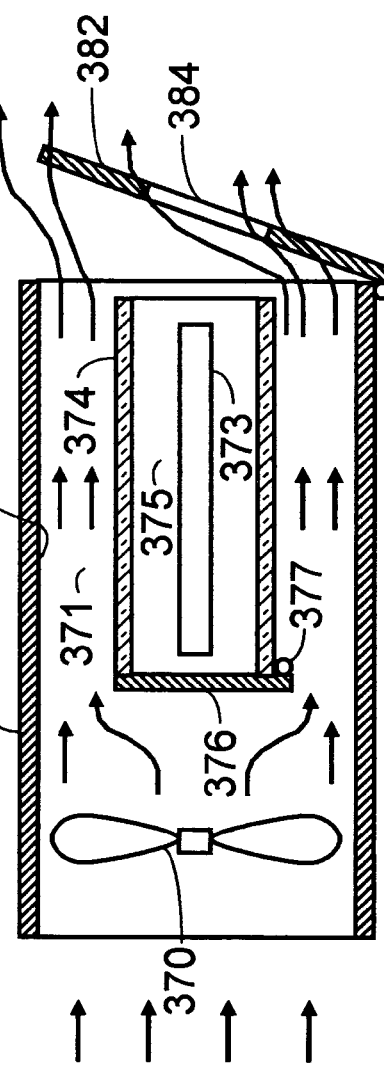

FIG. 14A, FIG. 14B, and FIG. 14C illustrate another alternative embodiment wherein another one-way door 382 containing a hole 384 over the end of chamber 375 and pivoted on hinge 383 is added to the basic embodiment of FIG. 13A. When reversible fan 370 is operated in a direction that pulls air through chamber 375 in a direction as indicated by flow arrows in chamber 375, one-way door 382 is pulled closed, preventing flow of air through chamber 371. This results in increased air flow and generation of ozone within chamber 375, further increasing concentrations of ozone provided to a volume in which air flowing past fan from chamber 375 is directed. When fan 370 or pitch of the blades of the fan is reversed, direction of air flow through chamber 371 is reversed, causing one-way door 382 to open and one-way door 376, pivoted on hinge 377, to close, with a result that, in this mode, ozone in air extracted from a volume by fan 370 and directed through chamber 371 is destroyed by UV-C radiation coming through glass wall 374 from VUV lamp 373. The de-ozonated air may then be directed via suitable valves and air passageways to a mask, helmet, hood, or other apparatus used to supply breathing air to a human or animal. Other features arbitrarily changed for example in this embodiment, but not related to addition of door 382, include use of a chamber wall 380 opaque to ultraviolet radiation, having an optional reflective surface 378, and use of a hybrid lamp 372 shown in FIG. 13A and FIG. 13B.

FIG. 15A, FIG. 15B, and FIG. 15C illustrate one of many embodiments that may be used for one-way valves and air flow restriction devices mentioned earlier in descriptions of various embodiments and modes of operation of the instant invention. FIG. 15A provides an end-on view of a one-way air valve 390 comprising an outer shoulder 394, an outer spoke ring 392, spokes 396 supporting a center hub 398 which in turn provides support for a pin or threaded screw 400, which, in turn, supports valve door 402. As illustrated in a side-on view of one-way valve 390 shown in FIG. 15B, valve door 402 may move from its illustrated open position to an alternated position 404 when direction of air flowing through a passageway in which valve 390 is mounted is reversed, thereby blocking air flow in the reverse direction. One or more springs 406 with different spring properties may be added on screw 400 above (as illustrated), below (not illustrated), or to either side of valve door 402. Selection of spring properties, and adjustment of spring tension by use of screw 400, which may have an extended length 407 through hub 398, will allow adjustment of valve 390 so that it does not open until a certain pressure is applied, or does not close until a certain pressure is applied, thus providing an ability to control passage of air through various air passageways of embodiments of the instant invention.

FIG. 16A, FIG. 16B, and FIG. 16C show how an alternative one-way valve similar to a reed valve of a 2-stroke engine may be constructed to be used in place of one-way door 382 (FIG. 14A) and other similar applications. A rigid disk 410 made of metal, plastic, or other material has a large center hole that may be placed over an end of chamber 375 (FIG. 14A) and other holes 412 through which air can flow. A disk 416 made of a relatively thin piece of metal, plastic, or other material (ozone resistant where necessary) having about the flexibility of a playing card or an index card may have generally rectangular sections 418 punched through or otherwise formed so that sections 418 are cut through disk 416 on three sides but remain hingeably connected on a fourth side so that each section 418 can act as a flap or door, opening and closing on its hinged side 420 under influence of pressure differences or other forces acting on disk 416 and sections 418. A hole 422 in the center of disk 416 matches hole 414 in center of disk 410. When disk 416 is stacked on top of disk 410 so that door sections 418 in disk 416 line up over holes 412 in disk 410, the resulting apparatus will function as a one-way valve or air flow restrictor when used to surround chamber 375 in FIG. 14A or in similar applications. Extension of this basic approach may be easily made for other applications where one-way valves or air flow restrictors are needed in various embodiments of the instant invention. Stiffness of material and size and number of holes can be varied to control amount of air flow restriction created in different embodiments of this one-way valve.

Figure 17A:
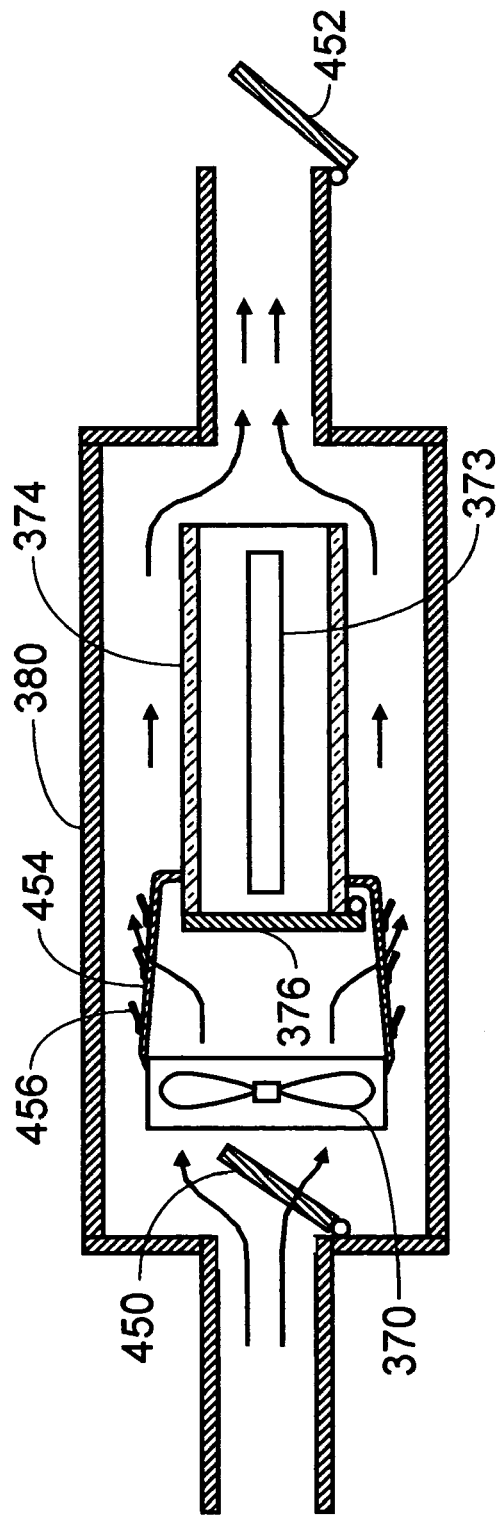
FIGS. 17A and 17B are illustrations showing how ozone concentrations may be further enhanced using an apparatus similar to that of FIGS. 14A and 14B.
Figure 17B:
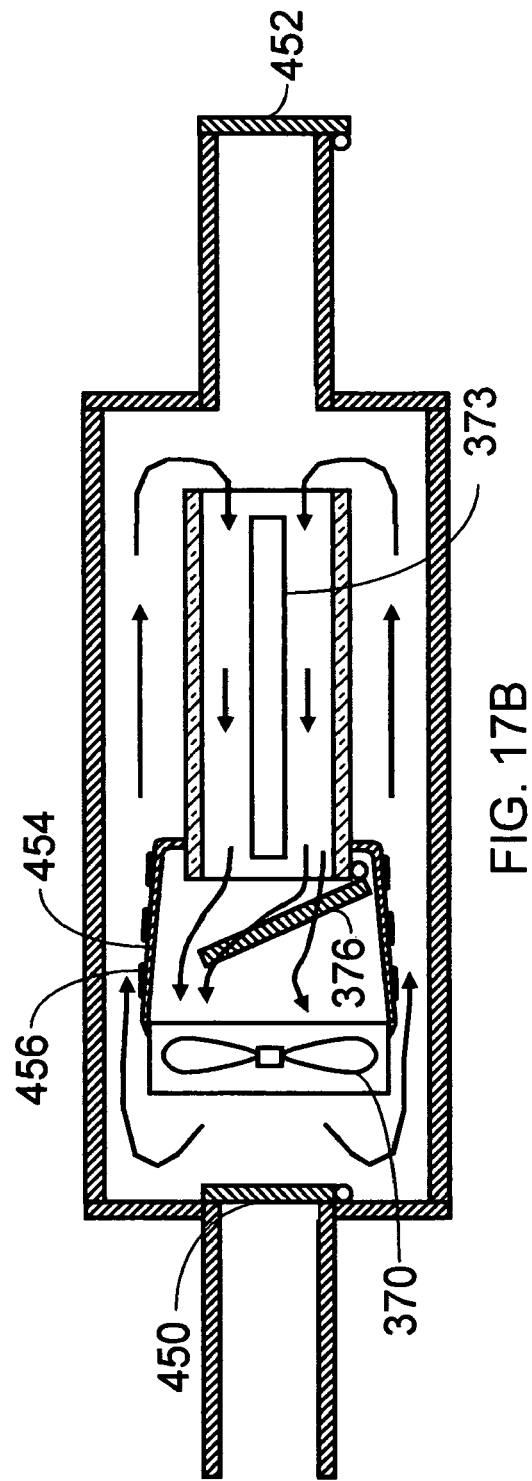

FIGS. 17A and 17B illustrate how a single ultraviolet lamp 373 can be used in conjunction with a reversible fan 370 (or optionally a fan with reversible pitch blades), glass cylinder 374, and one-way valves 450, 376, 452, 456 to achieve concentration of ozone in a parcel of air. One-way valves 456 may be flapper valves constructed over holes in a conic section 454 in a manner similar to that shown in FIGS. 16A, 16B, and 16C. One-way valve 452 is optional depending upon the volume of the enclosed chamber and the rigidity of enclosure walls 380. When reversible fan 370 is run in one direction, air, which may already contain some ozone, enters an enclosure indicated by flow arrows in FIG. 17A and circulates between glass cylinder 374 and enclosure walls 380 where it is exposed to UV-C radiation but not to VUV radiation, exiting then through one-way valve 452. When reversible fan 370 is subsequently run in a reverse direction, one-way valves 456 in conic section 454 close, forcing air to flow between ultraviolet lamp 373 and glass cylinder 374 where air is exposed to VUV radiation, resulting in creation of additional ozone. Although some ozone is destroyed by UV-C exposure in the air path indicated in FIG. 17B, a net effect is increased concentration of ozone until some saturation level is reached. Thus, this reverse mode may be allowed to continue for a short period to allow a buildup of ozone, after which fan 370 may be reversed again, reverting to an air flow path as indicated in FIG. 17A, exhausting air with concentrated ozone through one-way valve 452, and bringing in another parcel of air in which ozone may be concentrated in a subsequent portion of a cycle. Alternatively, fan 370 may continue to be operated to create an air flow direction as indicated in FIG. 17A, resulting in continued destruction of ozone in air passed through the assembly shown in FIG. 17A.

FIGS. 18A, 18B, and 18C illustrate aspects of an embodiment of an integrated ozone generation and destruction tube and, optionally, a source of visible or near-infrared fluorescent light, based on principles taught earlier herein. Various embodiments of this tube could be used in conjunction with broader system embodiments as were shown earlier herein and in earlier disclosures of air purification devices by Applicant; however, some features of this assembly are particularly important for applications involving decontamination of air and items from dangerous biological and chemical agents and purification of air for breathing. These features include techniques for increasing exposure duration and exposure intensity of air flowing through VUV and UV-C exposure chambers to increase lethality against biological agents and increased effectiveness against chemical agents.

Referring to FIG. 18A, in this embodiment, air to be ozonated enters ultraviolet radiation exposure assembly 600 through opening 601 and into entrance chamber 604 from which it flows into VUV exposure chamber 612 through openings 608 in inner end cap 610 that provides conventional support and electrical connections 605, 607 for VUV lamp 614. Inner end caps 610, 628 may be made of a generally solid disk with holes 608, 629 as illustrated in FIG. 18C, or may be made in a hub and spoke form similar to that illustrated for one-way valve 390 in FIG. 15A or similar to hub and blade spokes in circular vents found on outdoor charcoal barbeque grills. Electrical contacts 607 may be designed and positioned so as to make for easier installation and changeout of ultraviolet radiation exposure assembly 600 in higher level assemblies to provide ozone for decontamination or to provide de-ozonated air for breathing. As explained earlier herein, air flowing through VUV exposure chamber 612 is exposed to a combination of VUV and UV-C radiation, leading to creation of ozone and ozonites in the air stream as well as destruction of chemical and biological contaminants via exposure to VUV and UV-C radiation as well as normal and advanced oxidation reactions with ozone and ozonites. To help insure destruction of chemical or biological contaminants, baffles, such as helical baffle 620, or other air routing structures are used to force air flowing through VUV exposure chamber 612 to follow a longer path through exposure chamber than simply flowing the length of tube 614. Helical baffle 620 may be similar in form and cross section to that of a helical spring, such as a Slinky™ toy spring, but should preferably have thinned edges or edges coated with a material that will help provide an air-tight seal between inner edges of baffle 620 and outer surface of ultraviolet lamp 614 and between outer edges of baffle 620 and inner surfaces of cylinder 615. A helical baffle made of a conductive material, including metals and conductive plastics, may also be used as an electromagnetic coil to help constrict plasma within ultraviolet lamp 614 as described above. Alternate embodiments may use baffles or air passageways, on an interior surface 613 of outer cylinder 615, or on an insert placed between ultraviolet lamp tube 614 and interior walls of cylinder 615 to increase path length that air must follow through chamber 612, and thus increase exposure duration of air and contaminants flowing through integrated tube assembly 600. Such baffles or air passageways are preferably made of glass or another material that will tolerate exposure to VUV radiation. Examples of other alternatives to use of a helical path include passageways implemented to cause air to flow in a zig-zag path back and forth multiple times in directions transverse to the axis of lamp tube 614 while also flowing the length of tube 614, or passageways implemented to cause air to flow back and forth along the length of tube 614 before exiting VUV exposure chamber 612 through holes placed similarly to holes 626 or holes 629. Additional path length helps insure that the combination of the total integrated flux of VUV and UV-C radiation, as well as exposure duration to an advanced oxidation environment existing within VUV exposure chamber 612, is sufficient to cause a desired level of lethality of biological pathogens and breakdown and oxidation of chemical contaminants. Lethality and effectiveness against various contaminants vs overall air flow may be controlled by varying the pitch of a helical insert or by other techniques for varying path length.

FIGS. 18B and 18C provide further illustration of how holes 626 and 629 may be placed in cylinder 615 to provide exit paths for ozonated air from VUV chamber 612. Referring back to FIG. 18A, where only ozonated air is needed for use in decontaminating a volume, ozonated air from VUV chamber 612 may be routed through holes 629 to exit end cap 634 through a hole 632 from which ozonated air may be routed to an enclosure for decontamination of contents. Ultraviolet radiation exposure assembly 600 may also be used to provide decontaminated breathing air through opening 640. Where breathing air is needed, ozonated and sterilized air from VUV chamber 612 may be routed through holes 626, preferably positioned in an end of tube assembly 600 opposite to opening 640, into UV-C exposure chamber 618 which may be another helical volume defined by helical ridges 616 formed around cylinder 615, and by an outer cylinder 622. Air flowing in a helical path from holes 626 is exposed to UV-C radiation passing through cylinder 615 from ultraviolet lamp 614 before exiting from chamber 618 through exit hole 640. Openings 601, 632, and 640 may be incorporated into special fittings, such as quick-disconnect fittings, if desired to accommodate installation or replacement of tube assembly 600 into a higher level assembly with less effort. If it is not desired to use excess UV-C radiation escaping from chamber 618 through cylinder 622 to created visible or near-IR light by driving phosphors integrated into another cylinder or plastic coating 624, then a reflective coating 613 may be added to a surface of cylinder 622 to reflect UV-C radiation back into chamber 618, thereby increasing efficiency of de-ozonation processes within chamber 618. Outer end caps 602, 634 may be permanently attached to their respective inner end caps 610, 628, or outer and inner end caps may be joined by threads or other fastening techniques that permit disassembly. Either or both inner end caps 610, 628 may be attached to cylinder 615 by use of threads 609 or similar devices that permit an end-cap to be easily removed for replacement of ultraviolet lamp 614 or baffle 620 or for cleaning or servicing of other parts. Alternately, either or both end cap assemblies may be permanently attached to cylinder 615 and other parts, especially if overall tube assembly 600 is intended to be a non-repairable or disposable item.

To enable enhanced efficiency in production of ozone, wall thickness and other features of tube assembly 600 may be designed to permit operation of exposure chambers at pressures up to several times atmospheric pressure. Operation at higher pressures will result in increased absorption of ultraviolet radiation per unit path length in air within VUV exposure chamber 612, resulting in greater efficiency in production of ozone, and will also result in greater absorption per unit path length of UV-C radiation by ozone molecules in UV-C exposure chamber, which also increases efficiency in use of UV-C radiation in destruction of ozone.

The structure and operation of ultraviolet radiation exposure assembly 650 illustrated in FIG. 19 is similar to that of assembly 600 illustrated in FIGS. 18A, 18B, and 18C, except that helical ridged glass cylinder 615 and baffle 620 are replaced with a single helically corrugated baffle 623 made of a material that transmits UV-C radiation but blocks VUV radiation. Corrugated baffle 623 may be made of silicate glass, but glass may be difficult to form in an appropriate shape. Alternative UV-C transmissive materials that may be more easily formed into a desired shape include FEP and TFE plastics, which are alternative forms of a plastic material similar to Teflon™. Some of these alternative materials are available in heat-shrinkable tubes that could be heat shrunk over a helical corrugated core form treated with a mold release agent or another lubricant so that corrugated baffle 623 thus formed could be unscrewed from a core form after a baffle and form have cooled. In this embodiment, air introduced through holes 608 flows into a helical VUV exposure chamber 612 formed by a wall of corrugated baffle 623 and a wall of ultraviolet lamp 614. Air is forced by corrugated baffle 623 to flow around ultraviolet lamp 614 in a helical path which increases path length and exposure duration of air to VUV radiation, increasing lethality and destruction of biological pathogens and chemical contaminants in air flowing through chamber 612, and also increasing production of ozone and ozonites. Air thus ozonated, sterilized, and purified may then exit assembly through holes 629 and opening 632 to be used in decontaminating a protective suit or other contaminated volume. Alternatively, or in addition, air that has been decontaminated and ozonated by flowing through VUV chamber 612 may be caused to flow through holes 626 in walls of corrugated baffle 623 and into a different helical chamber 618 formed by outer walls of corrugated baffle 623 and inner wall 613 of cylinder 622 and used as a UV-C exposure chamber 618. Air flowing through UV-C exposure chamber 618 from entrance holes 626 to exit opening 640 is exposed to UV-C radiation flowing through baffle 623 leading to de-ozonation and additional sterilization of this air before it is discharged through opening 640 for use as breathing air. Dimensions and materials of helical corrugated baffle 623 should be selected to provide an air-tight seal between respective edges of baffle 623 and ultraviolet lamp 614 and cylinder 622.

FIG. 20 illustrates another embodiment 660 of an ultraviolet radiation exposure assembly similar to embodiment 650 illustrated in FIG. 19 except that baffle 623 in FIG. 19 is replaced with a triangular baffle 627 and dimensions and outer structure are modified to accommodate addition of optional phosphors and filter material for generation of visible or near-IR radiation. Triangular baffle 627 has helical ridges with each ridge having a generally triangular shape similar to a cross-sectional shape of standard threads on a bolt. Triangular baffle 627 may be made of silicate glass, FEP or TFE plastic, or other materials that transmit UV-C radiation but block transmission of VUV radiation. In this embodiment, a helical VUV exposure chamber 612 is formed by inner walls of triangular baffle 627 and outer wall of ultraviolet lamp 614. A separate helical UV-C exposure chamber is formed by outer walls of triangular baffle 627 and inner walls of cylinder 622. As in embodiments described above, air to be decontaminated and ozonated enters VUV exposure chamber 612 through opening 601 in outer end cap 602 and through holes 608 in inner end cap 610. Decontaminated and ozonated air may be caused by external pressures to flow from VUV chamber 612 through holes 629 and opening 632 from which it may be routed to a contaminated volume as indicated in FIGS. 4 and 4A and in other embodiments and applications taught herein. Decontaminated and ozonated air may also flow through holes 626 into helical UV-C chamber 618 for de-ozonation and additional decontamination and sterilization by UV-C radiation transmitted through triangular baffle 627 from ultraviolet lamp 614 before exiting through opening 640 as air suitable for breathing. An optional wire or small diameter coil spring, similar to drive springs found on movie projectors, approximately one-eighth inch in diameter, may be used to form a helical winding 621 around the valley portions of triangular baffle 627 to provide either or both of two functions. Optional helical winding 621 may be used to help keep valley portions of triangular winding 627 compressed against ultraviolet lamp 614 to help form an air tight seal and provide confidence that air flowing through VUV chamber 612 to be ozonated and decontaminated cannot bypass the intended helical path designed to insure adequate lethality and effectiveness. Optional helical winding 621 may also be electrically connected as disclosed in Applicant's U.S. Pat. No. 6,426,053, issued Jul. 30, 2002, or in Applicant's U.S. Pat. No. 6,951,633, issued Oct. 4, 2005, and used as an electromagnetic winding to enhance efficiency of ultraviolet lamp 614.

FIG. 5B and FIGS. 18A, 19, and 20 may be used together to illustrate how any of several separate embodiments of ultraviolet radiation exposure assembly 600, 650, or 660, as illustrated in FIGS. 18A, 19, and 20, could be used, with opening 632 sealed or blocked by a valve, cap, plug, or other device, in simple system embodiments of the instant invention intended only to provide decontaminated and de-ozonated breathing air to a mask or other volume 84 (reference FIG. 5B) where no need exists to provide ozonated air (through opening 632) for use, external to an embodiment of ultraviolet radiation exposure assembly 600, 650, or 660, in separate decontamination of volumes or items. Referring to FIG. 5B, in a system embodiment intended only for providing decontaminated and de-ozonated air for breathing, implementation of an ozone generator 66 and an ozone destruction device 78 may be accomplished by use of a single ultraviolet radiation exposure assembly 600, 650, or 660 with opening 632 sealed or blocked. VUV chamber 612 in assembly 600, 650, or 660 provides ozone generation and decontamination of air, while UV-C chamber 618 provides ozone destruction (and further decontamination of air). Breathable air volume 84 may be a face mask having a peripheral seal over a wearer's nose or mouth or both nose and mouth, and preferably also over a wearer's eyes, which seal is sufficiently tight to function in a manner similar to that of a flapper valve and prevent entrance of outside air during a wearer's inhalation cycle, but which seal permits escape of air during a wearer's exhalation cycle. Thus, in FIG. 5B, in addition to containing a breathing air volume 84, such a mask could also function, in effect, as a one-way flapper valve permitting flow, as indicated by arrow 72, from mask volume 84 to outside air 60 during a wearer's respiratory exhalation, but preventing flow from outside air 60 into mask air volume 84 during a wearer's inhalation portion of a respiratory cycle. Thus, in a simple system embodiment of FIG. 5B, assembly 600, 650, or 660 may be used together with an air mask or face mask as described above, with a one-way valve 82 located between face mask volume 84 and assembly 600, 650, or 660, which provides functions of ozone generation 66 and ozone destruction 78, to provide breathable air. In this simple embodiment, opening 640 of an assembly 600, 650, or 660 conventionally powered by a battery and suitable ballast for energizing ultraviolet lamp 612, and with opening 632 blocked or sealed, may be attached directly, or indirectly via air hose or other passageway, through a one-way valve 82, to a face mask that sufficiently seals over a wearer's nose, mouth, and preferably eyes to prevent entrance of outside air 60 during an inhalation portion of a wearer's respiratory cycle. One-way valve 82 is oriented and positioned to permit flow only in a direction from assembly 600, 650, or 660 into the face mask. During inhalation, possibly contaminated air is drawn by a wearer's respiration through opening 601 into and through VUV and UV-C chambers 612, 618, respectively, of assembly 600, 650, or 660, where the air is first decontaminated with ozone, ozonites, and ultraviolet radiation, and then air is de-ozonated and further sterilized by UV-C radiation before being provided through one-way valve 82 to mask volume 84 for breathing. During exhalation, one-way valve 82 prevents flow of exhaled air from mask volume 84 back through assembly 600, 650, or 660 and exhaled air is permitted by design and fit of the air mask to escape via a peripheral seal of a mask, which thus acts as a one-way valve for escape of air from a mask. For a simple embodiment where illumination of surroundings with visible or near-infrared light is desired, an assembly 600, 650, or 660 containing optional phosphors, as disclosed earlier herein, could be used. In such an embodiment, particularly a lightweight implementation using FEP or TFE plastic instead of glass to provide selective transmission of UV-C radiation, assembly 650 or 660 could be mounted on top of a face mask, similar to a miner's lamp, to provide both illumination and breathing air to a wearer. If an embodiment of an ultraviolet radiation exposure assembly tailored to providing breathing air only (i.e, no separate output of ozonated air), then an opening or passage between VUV and UV-C chamber, similar to that provided by holes 626, could be provided, and inner and outer end-caps may be modified to eliminate opening 632 and reduce production costs of an assembly thus tailored or customized for such an application.

Any of the embodiments of ultraviolet radiation exposure assembly illustrated in FIGS. 18A, 19, and 20, or similar embodiments, may also be used in a mode that provides only de-ozonation of air without intentional generation of ozone. This de-ozonation only mode can be accomplished by using valves, screw-on caps, or other techniques to prevent flow of air backwards (to the direction illustration by flow arrows in chamber 604 in FIGS. 18A, 19, 20) through opening 601, and then introducing air to be de-ozonated (and further sterilized) into opening 632 so that air flows in reverse (to direction indicated by air flow arrows in FIGS. 18A, 19, 20) through chamber 630 and through holes 629 into an end of VUV exposure chamber 612 nearest chamber 630. When prevented from flowing in reverse through an entire length of VUV chamber 612 by blockage of air flow, as noted just above, through opening 601, air entering VUV chamber 612 through holes 629 will be forced to flow through holes 626 into UV-C chamber 618, where the air will then flow through the length of UV-C chamber 618, being exposed to ozone destroying effects of UV-C radiation as described earlier, before thus de-ozonated air exits through opening 640. The safety of such air for breathing will depend upon the decontamination and sterilization of the air before it is introduced into opening 632 in this "reverse" mode for de-ozonation. Use of this mode may be augmented by optional addition of one-way valves in opening 601 or holes 608, or via addition of a insert containing a one-way valve into VUV exposure chamber 612 near, but just to the left, in FIGS. 18A, 19, 20, of holes 626. For most applications, such an insert would not be required, but an insert with a one-way valve in this position would prevent any backflow or mixing of air to be de-ozonated into portions of VUV chamber 612 where ozone would be generated. An ultraviolet radiation exposure assembly thus configured and used could support an efficient and compact implementation of a cyclic mode implementation of an ozone generation and treatment unit 94A as described in FIG. 7.

In yet another embodiment, air passage holes 626 between VUV chamber 612 and UV-C chamber 618, as illustrated in FIGS. 18A, 19, and 20, could be blocked or sealed by a controllable valve or other seal, or not provided at all, and a separate, additional opening into UV-C chamber 618, similar to opening 640 could be constructed at an end of ultraviolet radiation exposure assemblies 600, 650, 660 opposite to illustrated opening 640. This additional opening into UV-C chamber 618 could then be used to allow direct introduction into UV-C chamber 618 of air to be de-ozonated without requiring that such air be routed first "in reverse" through opening 632 and holes 629, as described in an embodiment discussed in the preceding paragraph. An embodiment of ultraviolet radiation exposure assembly, similar to embodiments illustrated in FIGS. 18A, 19, and 20, but with openings on both ends of UV-C exposure chamber 618, and air passage holes 626 blocked or sealed, would support simultaneous but independent flow of air being ozonated (in VUV chamber 612) and air being de-ozonated (in UV-C chamber 618) and could thus be used to support efficient and compact implementation of an embodiment of a continuous flow mode of an ozone generation and treatment unit similar to that depicted in FIG. 8.

In yet other alternative embodiments, holes 626 between VUV chamber 612 and UV-C chamber 618 could be sealed, one or more lengthwise channels could be provided along an outer surface in an end of glass cylinder 615 of FIG. 18A closest to inner end cap 628, with such channels providing air passageway between UV-C chamber 618 and holes similar to holes 629, and other features of inner and outer caps 628, 634, respectively, could be modified to provide a second opening similar to opening 632, and provide separate, independent air passageways through outer and inner end caps 634, 628, respectively, for independent access through end caps 634, 628 to VUV chamber 612 and to UV-C chamber 618. These modifications would provide another embodiment in which UV-C chamber 618 could be used independently of VUV chamber 612 to support various system level embodiments of the instant invention.

For embodiments of the instant invention such as illustrated in FIG. 5B that may be intended to provide only a sufficient quantity of air for breathing, but not necessarily sufficient air to accommodate losses of ozonated air that may occur in providing decontamination of a suit or other contaminated volume, the dimensions of an embodiment of an ultraviolet radiation exposure assembly may be approximately 20 to 25 cm long by 6 to 12 cm diameter and a volume of a VUV chamber 612 of an ultraviolet radiation exposure assembly similar to those illustrated in FIGS. 18A, 19, and 20 may range typically from about 0.25 liters to about 2 liters; however, the concentrations of ozone, and intensity and exposure durations of contaminants to ozone and to ultraviolet radiation, will vary according to type of contaminant, level of confidence required that specific contaminants are eliminated, susceptibility of specific contaminants to ozone, ozonites, and ultraviolet radiation, operating pressures, types of polishing filters used, and other variables. Lethality and effectiveness of specific embodiments may be controlled by variation of exposure path length, exposure duration, use of humidity or other compounds, and other measures as disclosed herein.

Figure 21:
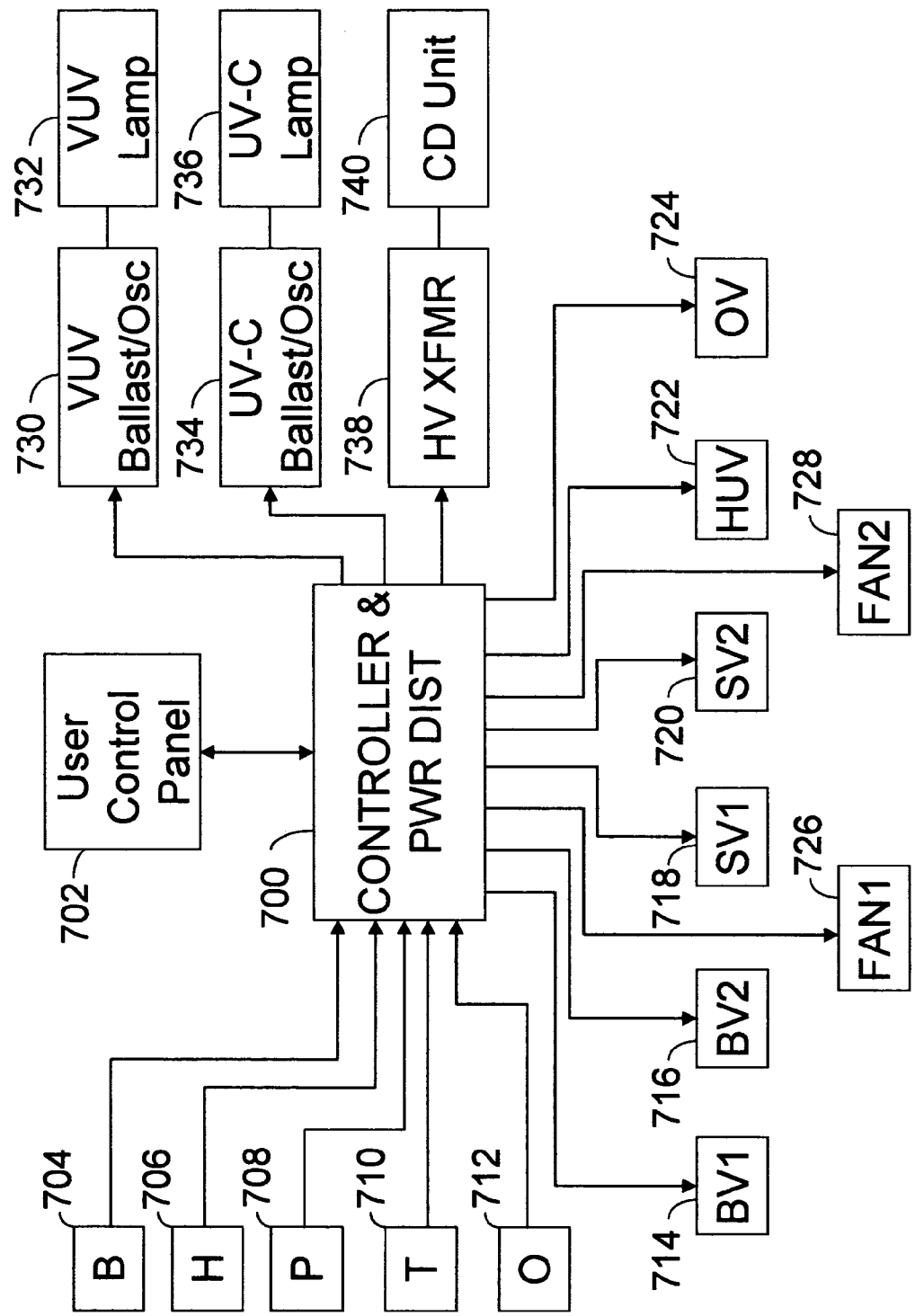
FIG. 21 is a schematic block diagram illustrating features of an embodiment of a control system that may be used with various embodiments of the instant invention.

FIG. 21 illustrates features of a control system that may be used with various embodiments of the instant invention. A user control panel 702 containing devices such as switches, pushbuttons, or touch panels, for user input, and preferably which devices can be operated by an individual wearing protective gloves, is connected to a controller 700 that implements control functions and controls distribution of power to components of an embodiment of the instant invention as needed to support various modes of operation. User control panel 702 may also include indicator lights, meters, or other devices for providing information on unit operation, or environmental conditions, to a user. User control panel 702 may also contain a capability to recognize and respond to voice command, or may simply contain a microphone, and a speaker or other devices for generating informational and warning sounds, and controller 700 may host a capability for recognizing and responding to voice signals transmitted by wire or by other media to controller 700 from a microphone in control panel 700 or elsewhere on an embodiment of the instant invention. In order to implement effective and efficient control of various actions and processes, and controller 700 may receive information from one or more of various sensors 704, 706, 708, 710, 712. For example, a sensor 704 may be used to monitor a respiratory rate of an individual being provided breathing air by an embodiment of the instant invention. Sensor 704 may sensor pressure within a mask being worn by an individual, or within a hose or chamber communicating with such a mask. Alternatively, a sensor 704 may simply be a microswitch in a one-way valve in such a mask that, as an example, presents an open connection during an inhalation portion of a wearer's respiratory cycle and a closed connection during an exhalation portion of a wearer's respiratory cycle. For cyclic mode embodiments such as described in association with FIG. 7 herein, or for other embodiments, control logic within controller 700 may then use these open and closed states to monitor a respiratory rate and estimate respiratory phasing of an individual being provided breathing air by a unit of the instant invention so that control commands may be issued to key components, such as control valves 718, 720 or fans 726, 728, that control air and modify air flow through a unit based on anticipation of a change from inhalation to exhalation, rather than having to wait, for example, and respond to pressure changes during each portion of a respiratory cycle, to change valve positions. A humidity sensor 706 may monitor humidity levels within an enclosure being decontaminated, or in air returned to a unit from an enclosure being decontaminated, to determine, for example, whether additional water should be added to a humidification filter by a humidity control valve 722, or alternately, whether air returning from a protective suit should be vented to outside air rather than being returned to prevent excess moisture buildup in a decontamination system or a volume being treated. For units employing pressurized ozonation chambers, a pressure sensor 708 located in a chamber or communicating air passageway may be used to provide pressure information to a controller 700 which may then increase or decrease speed of a fan 726, 728 or compressor, or change a setting of a control valve, to maintain a desired operating pressure in a component of a unit or system of the instant invention. A temperature sensor 710 may be used to monitor operating temperature in an exposure chamber or other location in the instant invention and provide temperature information to a controller 700 which may use such information to modify speed of a fan 726, 728 or duty cycle of a component, e.g., VUV lamp 732 or UV-C lamp 736 to maintain a desired temperature, or controller 700 may issue a warning tone via user control panel 702 and may also shut down a lamp ballast 730, 734 or other component causing an excess temperature. An oxygen concentration sensor 712 may be used to monitor oxygen concentration within a face mask or other location in a unit and provide information to a controller 700 which may use information on oxygen concentration to control a valve 724 on a tank of a self-contained breathing apparatus to allow more oxygen into a suit or other enclosure or air passageway to insure adequate levels for breathing or for production of ozone. In some embodiments, a carbon dioxide sensor or an ozone sensor could be used instead of, or in addition to, an oxygen sensor to monitor a concentration of carbon dioxide or ozone and issue a warning, e.g., via audible signal or flashing light on control panel, or initiate corrective actions such as changing a valve setting to increase venting of air containing excess carbon dioxide to outside air. In some embodiments, such as described in association with FIG. 7 and FIG. 8, controller 700 controls settings of bypass valves 714, 716 to help insure safe breathing air is provided in a bypass route to a wearer while ozonated air is initially being provided to a suit or other enclosure being decontaminated. Controller 700 may then change settings of bypass valves 714, 716, and suit valves 718, 720 controlling flow of ozonated air to a suit or other enclosure, and flow of return air from a suit back into a ozone generation and treatment unit of the instant invention. During startup operation, or at other times as required by operating conditions and user inputs, controller 700 may energize a high-voltage power supply 738 for a corona discharge unit 740 in order to boost concentration of ozone for initial decontamination or to provide a shock treatment to a volume being decontaminated. Depending upon operating mode and other parameters selected by a user via control panel 702, controller 700 also controls power and operating conditions for VUV lamp 732 and UV-C lamp 736 via their respective ballasts 730 and 734.

In yet another innovation that may be used to enhance efficiency of ozone production, or ozone destruction, and increased battery life for embodiments and applications involving operation of an ozone generation and treatment unit or an ultraviolet radiation and exposure assembly on battery power or on other limited power sources (e.g., solar panels, fuel cells), an oscillator capable of providing frequencies in a range typically from 20 kiloHertz to 40 kiloHertz is operated in conjunction with either or both of ballasts 730, 734, respectively, for VUV lamp 732 and UV-C lamp 736 and controller 700 controls a duty cycle for either or both of VUV lamp 732 and UV-C lamp 736 so that either or both lamps 732, 736 may be operated in a pulsed mode. Controller 700 may be able to separately control pulse durations and pulse repetition rates for either or both lamps. Since saturation levels for ozone concentrations in an immediate vicinity of a VUV lamp may be reached relatively quickly, or, stated another way, since unit ozone production for unit VUV radiation output from a lamp decreases rapidly after a lamp is turned on for a given air volume or air parcel surrounding a VUV lamp, most efficient, in terms of input electrical power, production of ozone occurs immediately after a lamp is turned on. Short pulse operation of a mercury vapor VUV lamp also limits output of UV-C radiation from such a lamp. Since, after a pulse of VUV radiation, leading to breakdown and disassociation of diatomic oxygen molecules, a short time is required for monatomic oxygen atoms to re-associate with other oxygen molecules and form ozone molecules, use of a mercury vapor lamp in short pulses generates ozone due to VUV output, but reduces destruction of ozone due to UV-C output, compared to steady state operation of a mercury vapor lamp. Thus, operation of a mercury vapor ultraviolet lamp (e.g., with purified quartz tube) in short pulses permits generation of higher ozone concentrations with less power compared to continuous mode operation of a mercury vapor ultraviolet lamp.

During discharge of a mercury vapor lamp, electrons flow from electrodes on one end of a lamp to electrodes on an opposite end of a lamp, thereby creating a plasma discharge and ultraviolet radiation due to collision of energetic electrons with atoms of vaporized mercury. Lamps which use heated electrodes and special coatings of materials such a barium that ionize easily and create a cloud of electrons around a heated electrode permit operation of a discharge lamp at lower levels of end-to-end voltage than lamps which have only cold (i.e., unheated) electrodes with no special coatings to promote generation of free electrons that may be used to initiate a plasma discharge. It is desirable to operate lamps having warm electrodes with special coatings using alternating end-to-end discharge voltages since, during each discharge in a given direction, a portion of coating material is transported from one electrode to another. If a lamp having warm electrodes is operated consistently with discharges in only one direction, coatings will be depleted on one end with a result that normal operating voltage for such a lamp will no longer initiate a discharge. Conversely, a higher voltage would be required to initiate a discharge in a lamp with thus depleted electrode coatings. Since it is desirable to operate lamps, especially those used in applications anticipated herein, using as low an operating voltages as low as practical, damage to electrode coatings must be avoided. If a lamp is operated in pulsed mode, to achieve the efficiency benefit described above, without attention to balancing directions of discharge, there is a risk of depleting electrode coatings on one end, leading to lamp failure. Thus, another innovation in the instant invention is the use of a relatively high frequency oscillator operating at a frequency of 20 kHz to 40 kHz, in conjunction with ballasts for VUV or UV-C lamps, to provide alternating end-to-end discharge voltages that change directions at frequencies of 20 kHz to 40 kHz. These operating frequencies are much higher than 60 Hz frequency at which most warm cathode mercury vapor discharge lamps are operated, including standard fluorescent lamps. If a discharge lamp, operating from a ballast and power supply providing only standard 50 to 60 Hz AC power, is operated with pulses shorter than $1/30^{th}$ to $120^{th}$ of a second, there is a risk of coating depletion on an electrode due to unbalanced end-to-end discharge direction, but when higher frequencies of 20 kHz to 40 kHz are used to drive discharge voltages, average discharge direction remains balanced, increasing overall reliability of a discharge tube.

A combination, then, of use of short duration pulses of a mercury vapor discharge lamp to preferentially create ozone in bursts with VUV radiation and reduce destruction of ozone by UV-C radiation, together with adequate air flow to move air through a VUV exposure chamber and provide adequate mixing and changing of air parcels immediately adjacent to a VUV discharge tube, and use of relatively high frequency discharge voltages, results in increased efficiency and reliability for ozone production. Care must be taken in balancing pulse duration and pulse repetition interval with air flow rates through ultraviolet radiation exposure assemblies and oxygen generation and treatment units of the instant invention to insure adequate exposure and lethality and destruction of any dangerous biological or chemical agents in air flowing through such exposure chambers.

Having disclosed my invention and the manner of its use, it should be apparent that incidental changes may be made thereto that fairly fall within the scope of the following appended claims, wherein I claim:

1. A system for providing decontaminated air for breathing comprising:

a closed volume of air, an ozone generator coupled to receive a first flow of said air from said closed volume of air, said ozone generator configured to provide ozone to said first flow of said air and further coupled to provide an ozonated said first flow of said air back to said closed volume of air, providing a reservoir of ozonated said air, an ozone destroyer coupled to receive a portion of said ozonated first flow of air, and provide a second flow of air substantially free of ozone, and a breathing enclosure configured to be sealably fitted to at least a nose and mouth of a user and coupled to provide said second flow of air substantially free of ozone to the user.

2. A system as set forth in claim 1 wherein said closed volume of air further comprises a generally airtight suit for enclosing a body of the user.

3. A system as set forth in claim 2 wherein said ozone generator further comprises an ultraviolet ozone-producing lamp in a radiation exposure chamber for receiving said first flow of air.

4. A system as set forth in claim 3 wherein said ozone destroyer further comprises a selective ultraviolet light filter around at least a portion of said ultraviolet lamp, said selective ultraviolet light filter passing only wavelengths from said ultraviolet lamp that destroy said ozone, and an air passageway around an exterior of said selective ultraviolet light filter that passes said second flow of air substantially free of ozone.

5. A system as set forth in claim 3 wherein said ultraviolet lamp is configured for producing wavelengths of ultraviolet light that destroy said ozone.

6. A system as set forth in claim 3 wherein said ozone generator further comprises a second ultraviolet lamp that generates wavelengths that develop ozone, said second ultraviolet lamp mounted in a radiation exposure chamber receiving said flow of air substantially free of ozone.

7. A system as set forth in claim 2 further comprising airflow apparatus for receiving outside air and coupled to said ozone generator for providing ozonated exterior air to an interior of said generally airtight suit to slightly pressurize said generally airtight suit so that if said generally airtight suit develops leakage ozonated air will flow out of said generally airtight suit, preventing contaminated external air from entering said generally airtight suit.

8. A system as set forth in claim 7 further comprising an airflow router that routes outside air through said ozone generator to replenish said reservoir of ozonated air.

9. A system as set forth in claim 2 further comprising a first airflow router wherein during inhalation by the user, said airflow router routes said flow of ozonated air through said ozone destroyer to provide said second flow of air substantially free of ozone for breathing by the user.

10. A system as set forth in claim 9 wherein during exhalation by the user, a second airflow router unidirectionally vents exhaled air to an exterior of said generally airtight suit.

11. A system as set forth in claim 9 wherein during exhalation of air by the user, a second airflow router unidirectionally provides air into said closed volume of air.

12. A system as set forth in claim 11 further comprising a carbon dioxide scrubber in said first flow of air to said ozone generator, and during inhalation by a user, said first airflow router draws ozonated air through said carbon dioxide scrubber from said closed volume of air and removes carbon dioxide from inhaled said air.

13. A system as set forth in claim 1 wherein said ozone generator is a corona discharge ozone generator for creating ozone in said first flow of air.

14. A system as set forth in claim 1 wherein said breathing enclosure further comprises an enclosure separate from said closed volume of air, said breathing enclosure for being sealably fitted about a head of the user.

15. A system as set forth in claim 14 wherein said-breathing enclosure is a flexible hood for sealably enclosing the head of the user, and coupled to receive said second flow of air substantially free of ozone.

16. A system as set forth in claim 15 further comprising a breathing tube for unidirectionally venting exhaled air to an outside of said flexible hood.

17. A system as set forth in claim 1 wherein said closed volume of air is a passenger compartment of a vehicle.

18. A system as set forth in claim 17 wherein said breathing enclosure is a mask for sealably fitting about a nose and mouth of the user.

19. A system as set forth in claim 1 wherein said ozone generator and said ozone destroyer further comprise:

a generally light-tight housing having a plurality of discrete air passageways, a source of ultraviolet radiation in said housing, said source of ultraviolet radiation emitting wavelengths including at least 185 nm ultraviolet radiation and 254 nm ultraviolet radiation, a selective ultraviolet radiation filter that strongly attenuates said 185 nm ultraviolet radiation while passing said 254 nm ultraviolet radiation, said selective ultraviolet radiation filter surrounding said source of ultraviolet radiation and configured to cooperate with said air passageways in said housing to create at least one extended in length 185 nm ultraviolet radiation exposure chamber and at least one extended in length 254 nm ultraviolet radiation chamber.

20. A system as set forth in claim 19 wherein said selective ultraviolet radiation filter is of a convoluted shape.

21. A system as set forth in claim 20 wherein said source of ultraviolet radiation is a cylindrical ultraviolet lamp and said filter is a glass cylinder having an inner diameter sufficient to enclose said cylindrical ultraviolet lamp and provide a common wall for an inner said 185 nm ultraviolet radiation exposure chamber and an outer said 254 nm ultraviolet radiation chamber, said inner chamber and said outer chamber surrounding said cylindrical ultraviolet lamp.

22. A system as set forth in claim 21 wherein said glass cylinder further comprises helical airflow-directing ridges on an outer surface of said glass cylinder, said helical airflow-directing ridges forming said 254 nm ultraviolet radiation exposure chamber.

23. A system as set forth in claim 21 wherein said convoluted shape forming said 185 nm ultraviolet radiation exposure chamber further comprises a helical structure positioned between an outer cylindrical surface of said ultraviolet lamp and an inner surface of said glass cylinder.

24. A system as set forth in claim 23 wherein said helical structure is electrically conductive and coupled to an electrical potential, for increasing efficiency of said ultraviolet lamp.

25. A system as set forth in claim 20 wherein said selective ultraviolet radiation filter of said convoluted shape further comprises a plastic material that passes said 254 nm ultraviolet radiation.

26. A system as set forth in claim 19 wherein said housing is generally cylindrical, with one end of said housing removable for cleaning and replacement of components.

* * * * *